(12) United States Patent
Mabire et al.

(10) Patent No.: US 7,855,207 B2
(45) Date of Patent: *Dec. 21, 2010

(54) 6-ALKENYL AND 6-PHENYLALKYL SUBSTITUTED 2-QUINOLINONES AND 2-QUINOXALINONES AS POLY(ADPRIBOSE) POLYMERASE INHIBITORS

(75) Inventors: Dominique Jean-Pierre Mabire, La Ferté Macé (FR); Jérôme Emile Georges Guillemont, Ande (FR); Jacobus Alphonsus Josephus Van Dun, Kasterlee (BE); Maria Victorina Francisca Somers, Vosselaar (BE); Walter Boudewijn Leopold Wouters, Kapellen (BE)

(73) Assignee: Janssen Pharmaceutica, NV, Beerse (BE)

(*) Notice: Subject to any disclaimer, the term of this patent is extended or adjusted under 35 U.S.C. 154(b) by 222 days.

This patent is subject to a terminal disclaimer.

(21) Appl. No.: 10/595,891

(22) PCT Filed: Nov. 18, 2004

(86) PCT No.: PCT/EP2004/013163

§ 371 (c)(1),
(2), (4) Date: May 18, 2006

(87) PCT Pub. No.: WO2005/054201

PCT Pub. Date: Jun. 16, 2005

(65) Prior Publication Data

US 2007/0072842 A1      Mar. 29, 2007

(30) Foreign Application Priority Data

Nov. 20, 2003 (WO) .................. PCT/EP03/13028
Dec. 5, 2003 (EP) .................. 03078860

(51) Int. Cl.
*A61K 31/498* (2006.01)
(52) U.S. Cl. .................. 514/249; 544/354; 546/157
(58) Field of Classification Search .................. 544/354; 546/157
See application file for complete search history.

(56) References Cited

U.S. PATENT DOCUMENTS 5,028,606 A * 7/1991 Venet et al. .................. 514/249

5,177,075 A     1/1993 Suto et al.

FOREIGN PATENT DOCUMENTS

| EP | 0371564 B1 | 6/1990 |
| WO | WO 02/36599 A1 | 5/2002 |
| WO | WO 2004/043950 | * 5/2004 |

OTHER PUBLICATIONS

Ali et al., Synthesis and Antimicrobial Activities of Some Novel Quinoxalinone Derivatives, 2000, Molecules, 5, 864-873.*
Pailer et al., Synthesis of quinoxalone derivatives, 1962, Monatshefte fuer Chemie,93, 1005-1018.*
Borisy et al. Systematic discovery of multicomponent therapeutics. 2003, Proceedings of the National Academy of Sciences of the United States of America, 100, 7977-7982.*
Li et al., "PARP Inhibitors", *IDrugs*, 2001, pp. 804-812, vol. 4, No. 7, Current Drugs Ltd., GB.
Weltin et al., "Effect of 6(5-Phenanthridinone, an Inhibitor of Poly(ADP-ribose) Polymerase, on Cultured Tumor Cells", *Oncology Research*, 1994, pp. 399-403, vol. 6, No. 9, El Sevier Ltd., USA.
PCT Intl. Search Report, PCT/EP2004/013163,Apr. 20, 2005.

* cited by examiner

*Primary Examiner*—James O Wilson
*Assistant Examiner*—Brian McDowell

(57) ABSTRACT

The present invention provides compounds of formula (I) and compounds of formula (VII-a) as well as pharmaceutical compositions comprising said compounds and their use as PARP inhibitors

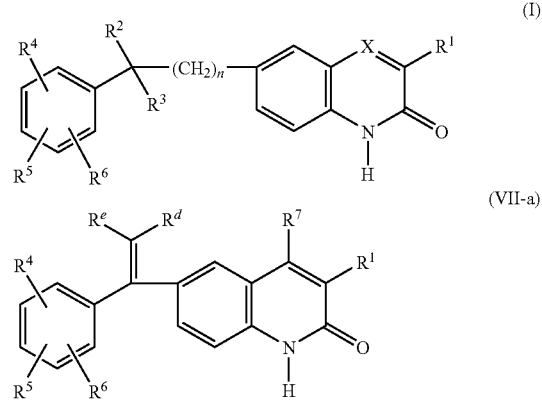

wherein n, $R^1$, $R^2$, $R^3$, $R^4$, $R^5$, $R^6$, $R^7$, $R^e$, $R^d$ and X have defined meanings.

5 Claims, No Drawings

6-ALKENYL AND 6-PHENYLALKYL SUBSTITUTED 2-QUINOLINONES AND 2-QUINOXALINONES AS POLY(ADPRIBOSE) POLYMERASE INHIBITORS

CROSS REFERENCE TO RELATED APPLICATIONS

This application is the national stage of PCT Application No. Application No. PCT/EP2004/013163, filed Nov. 18, 2004, which application claims priority from PCT Patent Application No. PCT/EP03/13028, filed Nov. 20, 2003 and EPO Patent Application No. 03078860.8, filed Dec. 5, 2003.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-ribose) polymerase-1 (PARP-1) is a member of the PARP enzyme family consisting of PARP-1 and several recently identified novel poly(ADP-ribosylating) enzymes. PARP is also referred to as poly(adenosine 5'-diphospho-ribose) polymerase or PARS (poly (ADP-ribose) synthetase).

PARP-1 is a major nuclear protein of 116 kDa consisting of three domains: the N-terminal DNA binding domain containing two zinc fingers, the automodification domain and the C-terminal catalytic domain. It is present in almost all eukaryotes. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{2+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold.

Among the many functions attributed to PARP, and especially PARP-1, is its major role in facilitating DNA repair by ADP-ribosylation and therefore co-ordinating a number of DNA repair proteins. As a result of PARP activation, $NAD^+$ levels significantly decline. Extensive PARP activation leads to severe depletion of $NAD^+$ in cells suffering from massive DNA damage. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^-$ depletion due to poly(ADP-ribose) turnover. Thus, PARP or PARG inhibition is expected to preserve the cellular energy level thereby potentiating the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues.

PARP is activated by damaged DNA fragments and, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of $NAD^-$ regenerated, $NAD^+$ is depleted by massive PARP activation, in the efforts to re-synthesize $NAD^+$, ATP may also become depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency. The potential role of PARP inhibitors in treating neurodegenerative diseases and head trauma has thus been recognized even if the exact mechanism of action has not yet been elucidated.

Similarly, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%) These results make it reasonable to assume that PARP inhibitors could salvage previously ischaemic heart or reperfusion injury of skeletal muscle tissue.

PARP activation can also be used as a measure of damage following neurotoxic insults resulting from exposure to any of the following inducers like glutamate (via NMDA receptor stimulation), reactive oxygen intermediates, amyloid β-protein, N-methyl-4-phenyl-1,2,3,6-tetrahydropyridine (MPTP) or its active metabolite N-methyl-4 phenylpyridine ($MPP^+$), which participate in pathological conditions such as stroke, Alzheimer's disease and Parkinson's disease. Other studies have continued to explore the role of PARP activation in cerebellar granule cells in vitro and in MPTP neurotoxicity. Excessive neural exposure to glutamate, which serves as the predominate central nervous system neurotransmitter and acts upon the N-methyl D-aspartate (NMDA) receptors and other subtype receptors, most often occurs as a result of stroke or other neurodegenerative processes. Oxygen deprived neurons release glutamate in great quantities during ischaemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{21}$ and Na into the cells and $K^1$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities. The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro.

Another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs.

Evidence also exists that PARP inhibitors are useful for treating inflammatory bowel disorders, such as colitis. Specifically, colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon.

Further evidence suggests that PARP inhibitors are useful for treating arthritis. Further, PARP inhibitors appear to be useful for treating diabetes. PARP inhibitors have been shown to be useful for treating endotoxic shock or septic shock.

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence disease; and to alter gene expression of senescent cells.

It is also known that PARP inhibitors, such as 3-amino benzamide, affect overall DNA repair in response, for example, to hydrogen peroxide or ionizing radiation.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

PARP inhibitors have been used to treat cancer. In addition, U.S. Pat. No. 5,177,075 discusses several isoquinolines used for enhancing the lethal effects of ionizing radiation or chemotherapeutic agents on tumor cells. Weltin et al., "Effect of 6(5-Phenanthridinone, an Inhibitor of Poly(ADP-ribose) Polymerase, on Cultured Tumor Cells", Oncol. Res., 6:9, 399-403 (1994), discusses the inhibition of PARP activity, reduced proliferation of tumor cells, and a marked synergistic effect when tumor cells are co-treated with an alkylating drug.

A recent comprehensive review of the state of the art has been published by Li and Zhang in IDrugs 2001, 4(7): 804-812.

There continues to be a need for effective and potent PARP inhibitors, and more particularly PARP-1 inhibitors which produce minimal side effects. The present invention provides compounds, compositions for, and methods of, inhibiting PARP activity for treating cancer and/or preventing cellular, tissue and/or organ damage resulting from cell damage or death due to, for example, necrosis or apoptosis. The compounds and compositions of the present invention are especially useful in enhancing the effectiveness of chemotherapy and radiotherapy where a primary effect of the treatment is that of causing DNA damage in the targeted cells.

BACKGROUND PRIOR ART

EP 371564, published on Jun. 6, 1990, discloses (1H-azol-1-ylmethyl) substituted quinoline, quinazoline or quinoxaline derivatives. The described compounds suppress the plasma elimination of retinoic acids. More in particular the compounds 6-[(1H-imidazol-1-yl)(4-methoxyphenyl)methyl]-3-methyl-2(1H)-quinoxalinone (compound No. 128 of the present application), 3-ethyl-6-(1H-imidazol-1-ylphenylmethyl)-2(1H)-quinoxalinone (compound No. 127 of the present application) and 6-[(4-chlorophenyl)-1H-imidazol-1-ylmethyl]-3-methyl-2(1H)-quinoxalinone (compound No. 146 of the present application) are disclosed.

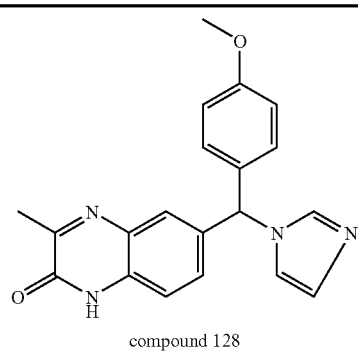

compound 128

-continued

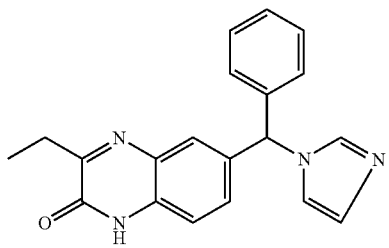

compound 127

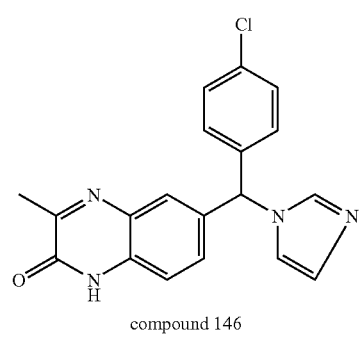

compound 146

DESCRIPTION OF THE INVENTION

This invention concerns compounds of formula (I)

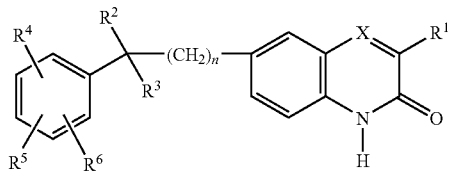

(I)

the N-oxide forms, the addition salts and the stereo-chemically isomeric forms thereof,
wherein
n is 0, 1 or 2;
X is N or $CR^7$, wherein $R^7$ is hydrogen or taken together with $R^1$ may form a bivalent radical of formula —CH=CH—CH=CH—;
$R^1$ is $C_{1-6}$alkyl or thiophenyl;
$R^2$ is hydrogen, hydroxy, $C_{1-6}$alkyl, $C_{3-6}$alkynyl or taken together with $R^3$ may form =O;
$R^3$ is a radical selected from —(CH$_2$)$_s$—NR$^8$R$^9$ (a-1), —O—H (a-2), —O—R$^{10}$ (a-3), —S—R$^{11}$ (a-4), or —C≡N (a-5), wherein
s is 0, 1, 2 or 3;
$R^8$, $R^{10}$ and $R^{11}$ are each independently selected from —CHO, $C_{1-6}$alkyl, hydroxy$C_{1-6}$alkyl, $C_{1-6}$alkylcarbonyl, amino, $C_{1-6}$alkylamino, di($C_{1-6}$alkyl)amino$C_{1-6}$alkyl, $C_{1-6}$alkyloxycarbonyl, $C_{1-6}$alkylcarbonylamino$C_{1-6}$alkyl, piperidinyl$C_{1-6}$alkylaminocarbonyl, piperidinyl, piperidinyl$C_{1-6}$alkyl, piperidinyl$C_{1-6}$alkylaminocarbonyl, $C_{1-6}$alkyloxy, thiophenyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl; and
$R^9$ is hydrogen or $C_{1-6}$alkyl;
or $R^3$ is a group of formula —(CH$_2$)$_t$—Z (b-1), wherein
t is 0, 1, 2 or 3;
—Z is a heterocyclic ring system selected from

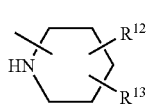 (c-1)

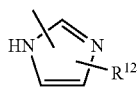 (c-2)

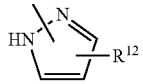 (c-3)

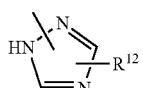 (c-4)

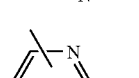 (c-5)

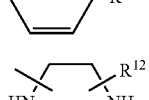 (c-6)

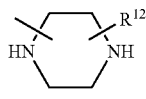 (c-6)

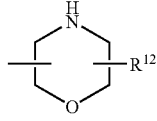 (c-7)

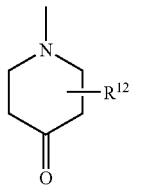 (c-8)

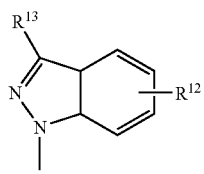 (c-9)

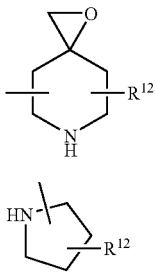

(c-10)

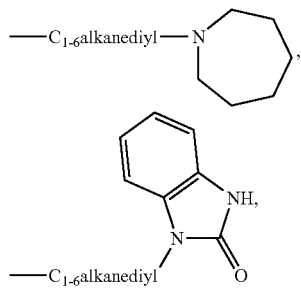

(c-11)

wherein R$^{12}$ is hydrogen, halo, C$_{1-6}$alkyl, aminocarbonyl, amino, hydroxy, aryl, —C$_{1-6}$alkanediyl—N⟨ring⟩

—C$_{1-6}$alkanediyl—⟨benzimidazolone⟩

C$_{1-6}$alkylaminoC$_{1-6}$alkyloxy, C$_{1-6}$alkyloxyC$_{1-6}$alkyl, C$_{1-6}$alkyloxyC$_{1-6}$alkylamino, arylC$_{1-6}$alkyl, di(phenylC$_{2-6}$alkenyl), piperidinyl, piperidinylC$_{1-6}$alkyl, C$_{3-10}$cycloalkyl, C$_{3-10}$cycloalkylC$_{1-6}$alkyl, aryloxy(hydroxy)C$_{1-6}$alkyl, haloindazolyl, arylC$_{1-6}$alkyl, arylC$_{2-6}$alkenyl, arylC$_{1-6}$alkylamino, morpholino, C$_{1-6}$alkylimidazolyl, or pyridinylC$_{1-6}$alkylamino;

R$^{13}$ is hydrogen, piperidinyl or aryl;

R$^4$, R$^5$ and R$^6$ are each independently selected from hydrogen, halo, trihalomethyl, trihalomethoxy, C$_{1-6}$alkyl, C$_{1-6}$alkyloxy, amino, aminoC$_{1-6}$alkyl, di(C$_{1-6}$alkyl)amino, di(C$_{1-6}$alkyl)aminoC$_{1-6}$alkyloxy or C$_{1-6}$alkyloxycarbonyl, or C$_{1-6}$alkyl substituted with 1, 2 or 3 substituents independently selected from hydroxy, C$_{1-6}$alkyloxy, or aminoC$_{1-6}$alkyloxy; or when R$^5$ and R$^6$ are on adjacent positions they may taken together form a bivalent radical of formula —O—CH$_2$—O— (d-1), —O—(CH$_2$)$_2$—O— (d-2), —CH=CH—CH=CH— (d-3), or —NH—C(O)—NR$^{14}$=CH— (d-4), wherein R$^{14}$ is C$_{1-6}$alkyl;

aryl is phenyl, phenyl substituted with halo, C$_{1-6}$alkyl or C$_{1-6}$alkyloxy;

with the proviso that when n is 0, X is N, R$^1$ is C$_{1-6}$alkyl, R$^2$ is hydrogen, R$^3$ is a group of formula (b-1), t is 0, Z is the heterocyclic ring system (c-2) wherein said heterocyclic ring system Z is attached to the rest of the molecule with a nitrogen atom, and R$^{12}$ is hydrogen or C$_{1-6}$alkyl; then at least one of the substituents R$^4$, R$^5$ or R$^6$ is other than hydrogen, halo, C$_{1-6}$alkyloxy and trihalomethyl.

Whenever the heterocyclic ring system Z contains a —CH$_2$—, —CH=, or —NH— moiety the substituents R$^{12}$ and R$^{13}$ or the rest of the molecule can be attached to the carbon or nitrogen atom in which case one or both hydrogen atoms are replaced.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; C$_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; C$_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihalomethyl defines methyl containing three identical or different halo substituents for example trifluoromethyl; C$_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; C$_{3-6}$alkynyl defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; C$_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and solvates and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Whenever used hereinafter, the term "compounds of formula (I)" is meant to include also the N-oxide forms, the pharmaceutically acceptable acid or base addition salts and all stereoisomeric forms.

The compounds described in EP 371564 suppress the plasma elimination of retinoic acids. 6-[(1H-imidazol-1-yl)(4-methoxyphenyl)methyl]-3-methyl-2(1H)-quinoxalinone (compound No. 128 of the present application), 3-ethyl-6-(1H-imidazol-1-ylphenylmethyl)-2(1H)-quinoxalinone (compound No. 127 of the present application) and 6-[(4-chlorophenyl)-1H-imidazol-1-ylmethyl]-3-methyl-2(1H)-quinoxalinone (compound No. 146 of the present application) have been disclosed in EP 371564. Unexpectedly, it has been found that the compounds of the present invention show PARP inhibitory activity.

A first group of interesting compounds consists of those compounds of formula (I) wherein one or more of the following restrictions apply:
a) $R^1$ is $C_{1-6}$alkyl;
b) $R^3$ is a radical selected from (a-1), (a-2), (a-3) or (a-5) or is a group of formula (b-1);
c) s is 0, 1 or 2;
d) $R^8$ and $R^{10}$ are each independently selected from —CHO, $C_{1-6}$alkyl, hydroxy$C_{1-6}$alkyl, di($C_{1-6}$alkyl)amino$C_{1-6}$alkyl, $C_{1-6}$alkylcarbonylamino$C_{1-6}$alkyl, piperidinyl$C_{1-6}$alkyl, piperidinyl$C_{1-6}$alkylaminocarbonyl, $C_{1-6}$alkyloxy, thiophenyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl;
e) t is 0 or 2;
f) Z is a heterocyclic ring system selected from (c-1), (c-2), (c-4), (c-6), (c-8), (c-9), or (c-11);
g) $R^{12}$ is hydrogen, $C_{1-6}$alkyl, aminocarbonyl,

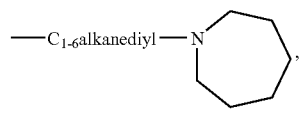

$C_{1-6}$alkyloxy$C_{1-6}$alkylamino, di(phenyl$C_{2-6}$alkenyl), piperidinyl$C_{1-6}$alkyl, $C_{3-10}$cycloalkyl, $C_{3-10}$cycloalkyl$C_{1-6}$alkyl, haloindazolyl, or aryl$C_{2-6}$alkenyl;
h) $R^4$, $R^5$ and $R^6$ are each independently selected from hydrogen, halo, trihalomethyl, trihalomethoxy, $C_{1-6}$alkyl, $C_{1-6}$alkyloxy, di($C_{1-6}$alkyl)amino, di($C_{1-6}$alkyl)amino$C_{1-6}$alkyloxy or $C_{1-6}$alkyloxycarbonyl; and
i) when $R^5$ and $R^6$ are on adjacent positions they may taken together form a bivalent radical of formula (d-1) or (d-2).

A second group of interesting compounds consists of those compounds of formula (I) wherein one or more of the following restrictions apply:
a) n is 0;
b) X is $CR^7$, wherein $R^7$ is hydrogen or taken together with $R^1$ may form a bivalent radical of formula —CH=CH—CH=CH—;
c) $R^1$ is $C_{1-6}$alkyl;
d) $R^2$ is hydrogen;
e) $R^3$ is a radical selected from (a-1), (a-2) or (a-3) or is a group of formula (b-1);
f) s is 0 or 2;
g) $R^8$ and $R^{10}$ are each independently selected from —CHO, $C_{1-6}$alkyl, di($C_{1-6}$alkyl)amino$C_{1-6}$alkyl, piperidinyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl;
h) t is 0 or 2;
i) Z is a heterocyclic ring system selected from (c-1), (c-2) or (c-6);
j) $R^{12}$ is hydrogen,

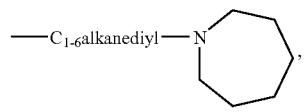

$C_{1-6}$alkyloxy$C_{1-6}$alkylamino, or piperidinyl$C_{1-6}$alkyl;

k) $R^{13}$ is hydrogen or aryl;
l) $R^4$, $R^5$ and $R^6$ are each independently selected from hydrogen or trihalomethyl; and
m) when $R^5$ and $R^6$ are on adjacent positions they may taken together form a bivalent radical of formula (d-1) or (d-2).

A third group of interesting compounds consists of those compounds of formula (I), the first group of interesting compounds or the second group of interesting compounds wherein Z is a heterocyclic ring system other than the heterocyclic ring system of formula (c-2) or (c-4).

A group of preferred compounds consists of those compounds of formula (I) wherein $R^1$ is $C_{1-6}$alkyl; $R^3$ is a radical selected from (a-1), (a-2), (a-3) or (a-5) or is a group of formula (b-1); s is 0, 1 or 2; $R^8$ and $R^{10}$ are each independently selected from —CHO, $C_{1-6}$alkyl, hydroxy$C_{1-6}$alkyl, di($C_{1-6}$alkyl)amino$C_{1-6}$alkyl, $C_{1-6}$alkylcarbonylamino$C_{1-6}$alkyl, piperidinyl$C_{1-6}$alkyl, piperidinyl$C_{1-6}$alkylaminocarbonyl, $C_{1-6}$alkyloxy, thiophenyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl; t is 0 or 2; Z is a heterocyclic ring system selected from (c-1), (c-2), (c-4), (c-6), (c-8), (c-9), or (c-11); $R^{12}$ is hydrogen, $C_{1-6}$alkyl, aminocarbonyl,

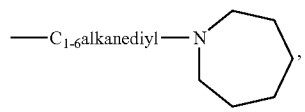

$C_{1-6}$alkyloxy$C_{1-6}$alkylamino, di(phenyl$C_{2-6}$alkenyl), piperidinyl$C_{1-6}$alkyl, $C_{3-10}$cycloalkyl, $C_{3-10}$cycloalkyl$C_{1-6}$alkyl, haloindazolyl, or aryl$C_{2-6}$alkenyl; $R^4$, $R^5$ and $R^6$ are each independently selected from hydrogen, halo, trihalomethyl, trihalomethoxy, $C_{1-6}$alkyl, $C_{1-6}$alkyloxy, di($C_{1-6}$alkyl)amino, di($C_{1-6}$alkyl)amino$C_{1-6}$alkyloxy or $C_{1-6}$alkyloxycarbonyl; and when $R^5$ and $R^6$ are on adjacent positions they may taken together form a bivalent radical of formula (d-1) or (d-2).

A further group of preferred compounds consists of those compounds of formula (I) wherein n is 0; X is $CR^7$, wherein $R^7$ is hydrogen or taken together with $R^1$ may form a bivalent radical of formula —CH=CH—CH=CH—; $R^1$ is $C_{1-6}$alkyl; $R^2$ is hydrogen; $R^3$ is a radical selected from (a-1), (a-2) or (a-3) or is a group of formula (b-1); s is 0 or 2; $R^8$ and $R^{10}$ are each independently selected from —CHO, $C_{1-6}$alkyl, di($C_{1-6}$alkyl)amino$C_{1-6}$alkyl, piperidinyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl; t is 0 or 2; Z is a heterocyclic ring system selected from (c-1), (c-2) or (c-6); $R^{12}$ is hydrogen,

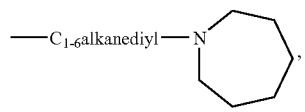

$C_{1-6}$alkyloxy$C_{1-6}$alkylamino, or piperidinyl$C_{1-6}$alkyl; $R^{13}$ is hydrogen or aryl; $R^4$, $R^5$ and $R^6$ are each independently selected from hydrogen or trihalomethyl; and when $R^5$ and $R^6$ are on adjacent positions they may taken together form a bivalent radical of formula (d-1) or (d-2).

An even further group of preferred compounds consists of those compounds of formula (I), the group of preferred compounds or the further group of preferred compounds wherein Z is a heterocyclic ring system other than the heterocyclic ring system of formula (c-2) or (c-4).

A group of more preferred compounds consists of those compounds of formula (I) wherein n is 0; X is CH; $R^1$ is $C_{1-6}$alkyl; $R^2$ is hydrogen; $R^3$ is a group of formula (b-1); t is 2; Z is a heterocyclic ring system selected from (c-1); $R^{12}$ is hydrogen; $R^{13}$ is hydrogen; and $R^5$ and $R^6$ are on adjacent positions and taken together form a bivalent radical of formula (d-2).

The most preferred compounds are compounds No 16, compound No 144, and compound No. 145.

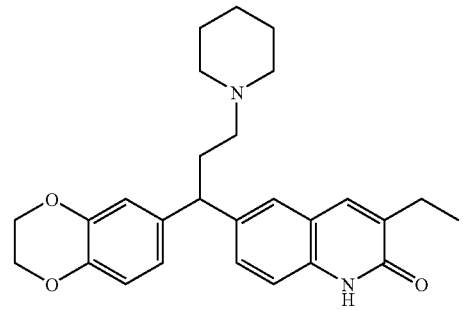

compound 16

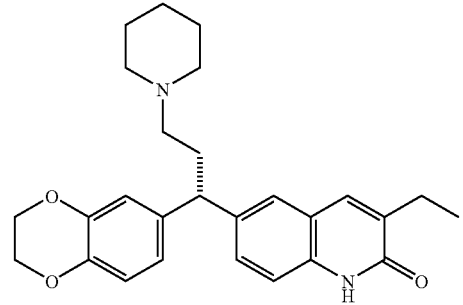

Compound 144

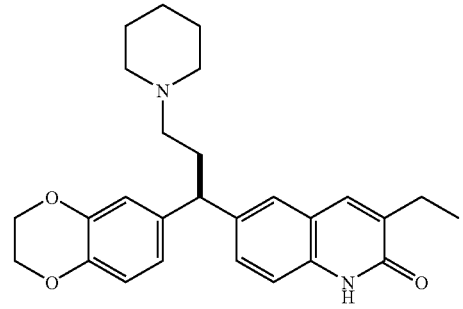

Compound 145

The compounds of formula (I) can be prepared according to the general methods described in EP 371564.

A number of such preparation methods will be described hereinafter in more detail. Other methods for obtaining final compounds of formula (I) are described in the examples.

Compounds of formula (I) wherein $R^2$ is hydrogen and $R^3$ is —$NR^9$—CHO wherein and $R^9$ is hydrogen or methyl, herein referred to as compounds of formula (I-b), can be prepared starting from compounds of formula (I), wherein $R^2$ taken together with $R^3$ forms =O, herein referred to as compounds of formula (I-a), in the presence of formamide or methylformamide, here indicated as intermediates of formula (II), and formic acid.

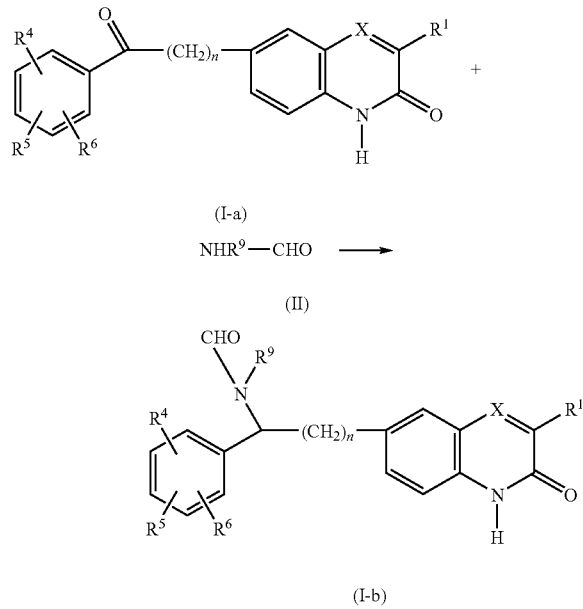

(I-a)

NHR$^9$—CHO →

(II)

(I-b)

Compounds of formula (I), wherein $R^3$ is hydroxy, herein referred to as compounds of formula (I-c), can be prepared by converting the keton moiety of compounds of formula (I-a) into an hydroxy group, with an appropriate reductant, e.g., sodium borohydride in a suitable solvent, e.g. methanol and tetrahydrofuran.

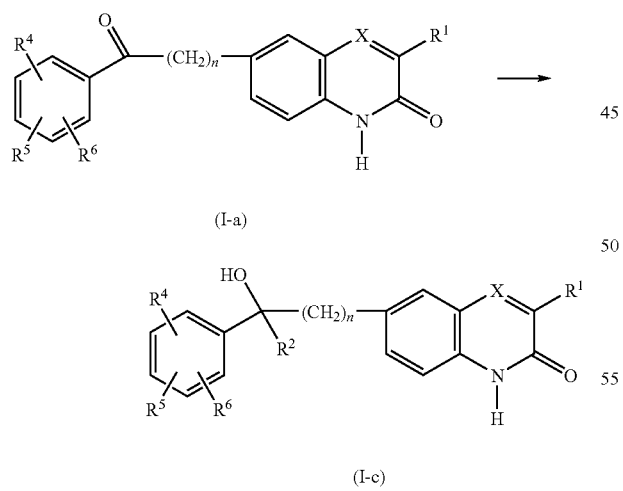

(I-a)

(I-c)

Compounds of formula (I-a) can be prepared by converting compounds of formula (I-c), wherein $R^2$ is hydrogen, herein referred to as compounds of formula (I-c-1), in the presence of a suitable oxidant such as chromium trioxide and an acid such as sulfuric acid, in a suitable solvent such as 2-propanone.

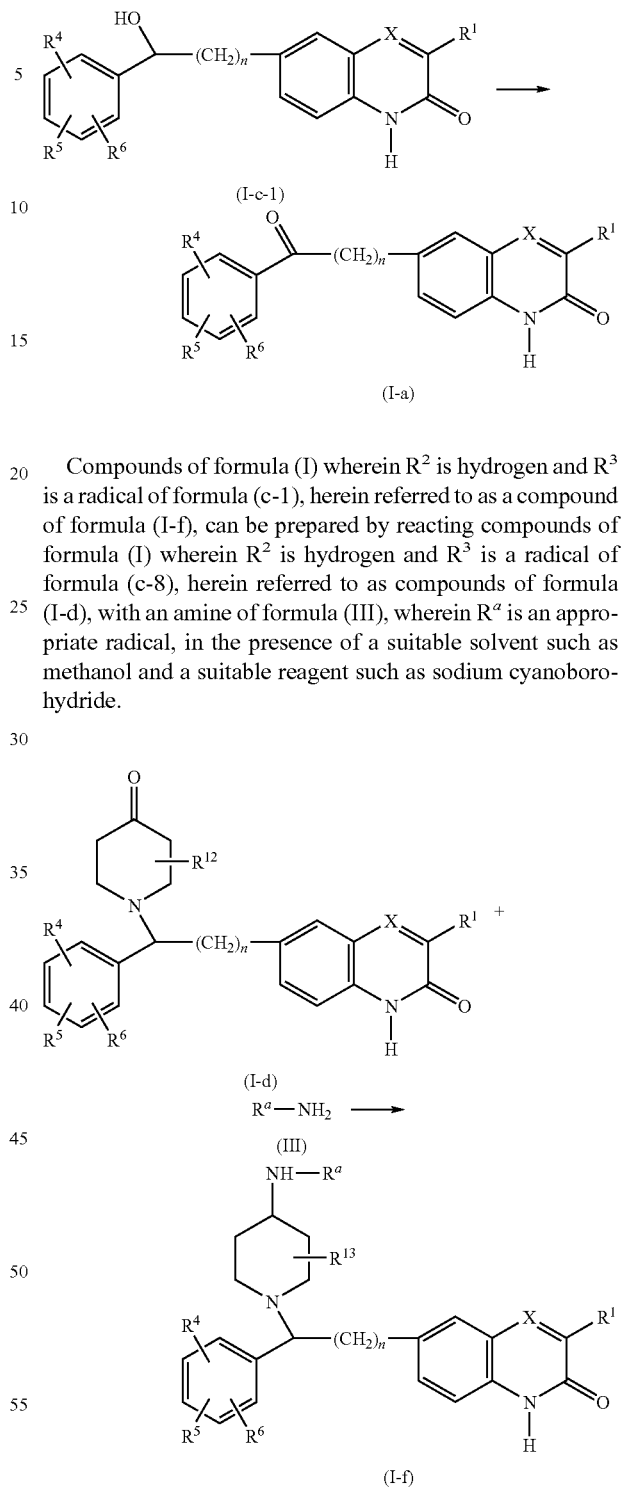

(I-c-1)

(I-a)

Compounds of formula (I) wherein $R^2$ is hydrogen and $R^3$ is a radical of formula (c-1), herein referred to as a compound of formula (I-f), can be prepared by reacting compounds of formula (I) wherein $R^2$ is hydrogen and $R^3$ is a radical of formula (c-8), herein referred to as compounds of formula (I-d), with an amine of formula (III), wherein $R^a$ is an appropriate radical, in the presence of a suitable solvent such as methanol and a suitable reagent such as sodium cyanoborohydride.

(I-d)

$R^a$—NH$_2$ →

(III)

(I-f)

Intermediates of formula (IV), wherein W is an appropriate leaving group such as, for example, chloro, bromo, methanesulfonyloxy or benzenesulfonyloxy can be prepared from compounds of formula (I-c-1) by treating said compounds with a suitable reagent e.g. methanesulfonyloxy chloride or benzenesulfonyloxy chloride, or a halogenating reagent such as e.g. POCl$_3$ or SOCl$_2$.

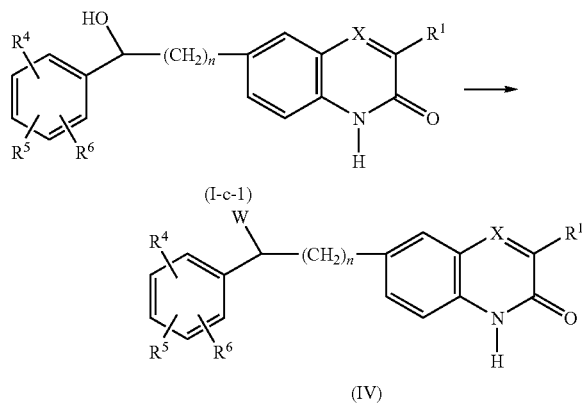

Compounds of formula (I), defined as compounds of formula (I) wherein $R^b$ is as defined in $R^8$ and $R^c$ is as defined in $R^9$, or $R^b$ and $R^c$ taken together with the nitrogen to which they are attached, form an appropriate heterocyclic ring system as defined in Z, herein referred to as compounds of formula (I-h), can be prepared by reacting an intermediate of formula (IV) with an intermediate of formula (V). The reaction can be performed in a reaction-inert solvent such as dimethylformamide or acetonitrile, and optionally in the presence of a suitable base such as, for example, sodium carbonate, potassium carbonate or thriethylamine.

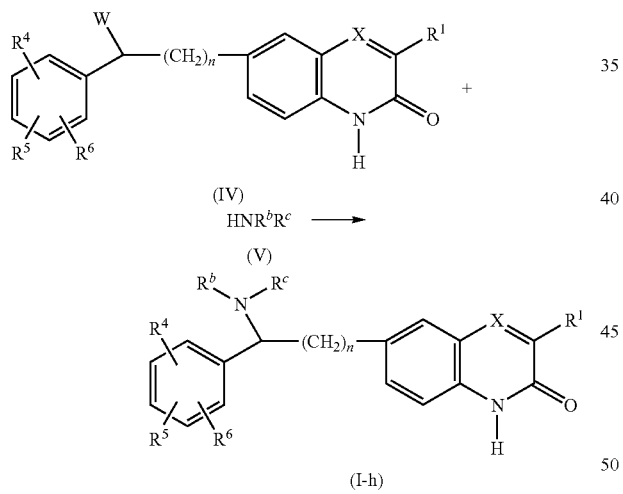

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

Hence, compounds of formula (I), (I-a), (I-a-1), (I-b), (I-c), (I-c-1), (I-d), (I-e), (I-f), (I-h), (I-i) and (I-j) can optionally be the subject of one or more of the following conversions in any desired order:

(i) converting a compound of formula (I) into a different compound of formula (I);

(ii) converting a compound of formula (I) into the corresponding acceptable salt or N-oxide thereof, (iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

Intermediates of formula (VII), wherein $R^d$ and $R^e$ are appropriate radicals or taken together with the carbon to which they are attached, form an appropriate heterocyclic ring system as defined in Z, can be prepared by hydrolysing intermediates of formula (VI), wherein $R^3$ is a group of formula (b-1) or a radical of formula (a-1) wherein s is other than 0, herein referred to as $R^g$, according to art-known methods, such as stirring the intermediate (VI) in an aqueous acid solution in the presence of a reaction inert solvent, e.g. tetrahydrofuran. An appropriate acid is for instance hydrochloric acid.

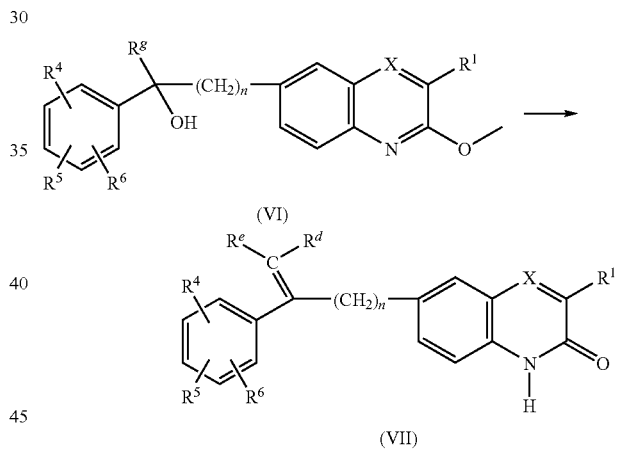

Compounds of formula (I) wherein $R^2$ is hydrogen and $R^g$ is as defined above, herein referred to as compounds of formula (I-i), can be prepared starting from intermediates of formula (VII), by a selective hydrogenation of said intermediate with an appropriate reducing agent such as, for example with a noble catalyst, such as platinum-on-charcoal, palladium-on-charcoal and the like and an appropriate reductant such as hydrogen in a suitable solvent such as methanol.

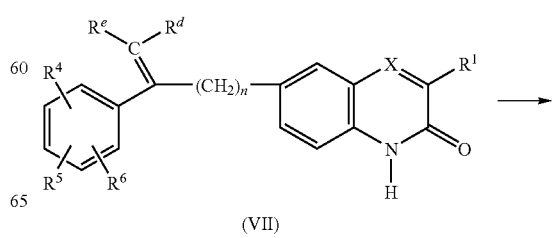

-continued

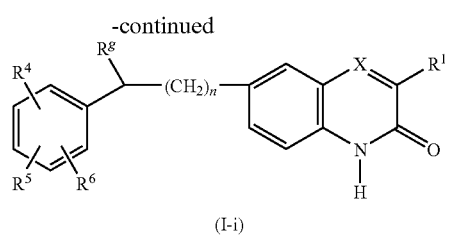

(I-i)

Compounds of formula (I) can be prepared by hydrolysing intermediates of formula (VIII), according to art-known methods, by submitting the intermediates of formula (VIII) to appropriate reagents, such as, tinchloride, acetic acid and hydrochloric acid, in the presence of a reaction inert solvent, e.g. tetrahydrofuran.

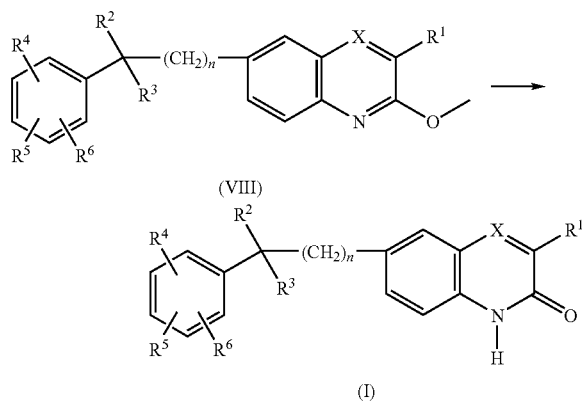

Compounds of formula (I) can be prepared starting from N-oxides of formula (IX) by converting the intermediates of formula (IX) in the presence of a suitable reagent such as sodium carbonate or acetic anhydride and when appropriate in a solvent such as dichloromethane.

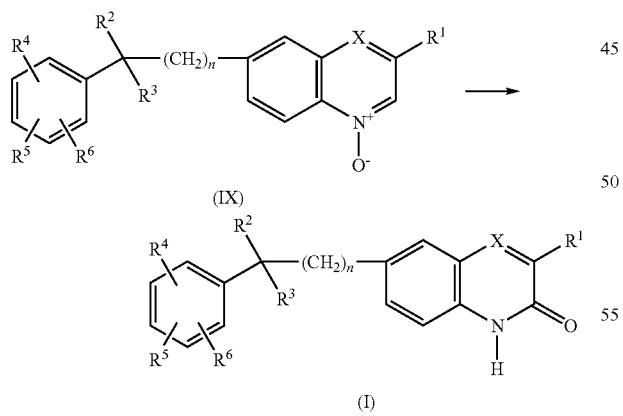

The compounds of formula (I) wherein X is CH herein referred to as compounds of formula (I-j), may also be obtained by cyclizing an intermediate of formula (X). The cyclization reaction of intermediates of formula (X) may be conducted according to art-known cyclizing procedures. Preferably the reaction is carried out in the presence of a suitable Lewis Acid, e.g. aluminum chloride either neat or in a suitable solvent such as, for example, an aromatic hydrocarbon, e.g. benzene, chlorobenzene, methylbenzene and the like; halogenated hydrocarbons, e.g. trichloromethane, tetrachloromethane and the like; an ether, e.g. tetrahydrofuran, 1,4-dioxane and the like; or mixtures of such solvents. Somewhat elevated temperatures, preferably between 70°-100° C., and stirring may enhance the rate of the reaction.

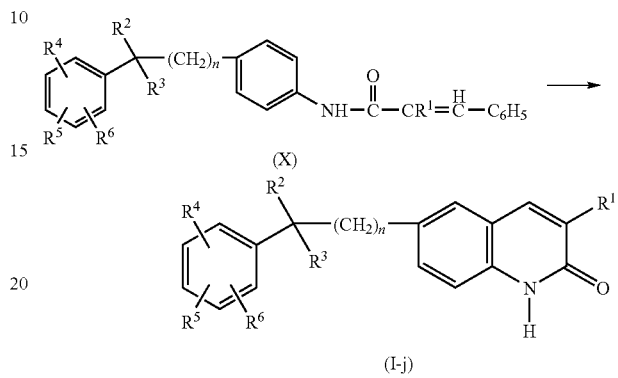

The compounds of formula (I), wherein X is N and $R^2$ taken together with $R^3$ forms =O, herein referred to as compounds of formula (I-a-1) may be obtained by condensing an appropriate ortho-benzenediamine of formula (XI) with an ester of formula (XII) wherein $R^h$ is $C_{1-6}$alkyl. The condensation of the substituted ortho-diamine of formula (XI) and the ester of formula (XII) can be carried out in the presence of a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like. Somewhat elevated temperatures may be appropriate to enhance the rate of the reaction and in some cases the reaction may even be carried out at the reflux temperature of the reaction mixture. The water which is liberated during the condensation may be removed from the mixture by azeotropical distillation, distillation and the like methods.

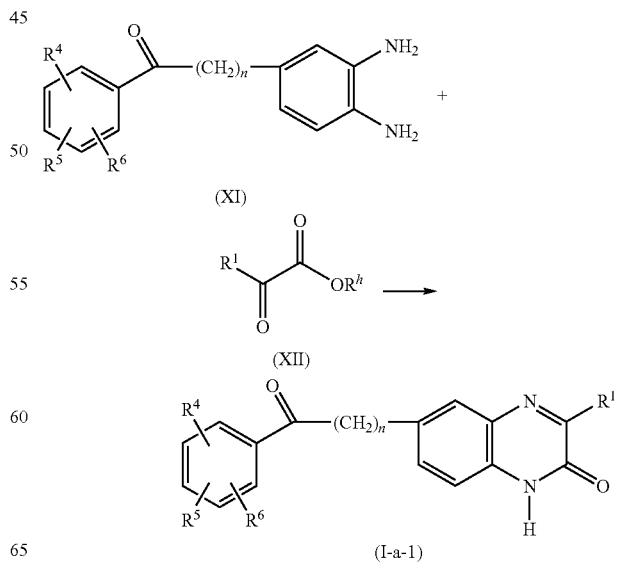

Intermediates of formula (XI) can be prepared by a nitro to amine reduction reaction starting with an intermediate of formula (XIII) in the presence of a metal catalyst such as Raney Nickel and an appropriate reductant such as hydrogen in a suitable solvent such as methanol.

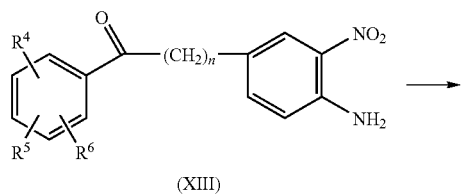

(XIII)

→

(XI)

Intermediates of formula (XIII) can be prepared by hydrolysing intermediates of formula (XIV), according to art-known methods, such as stirring the intermediate (XIV) in an aqueous acid solution in the presence of a reaction inert solvent, e.g. tetrahydrofuran. An appropriate acid is for instance hydrochloric acid.

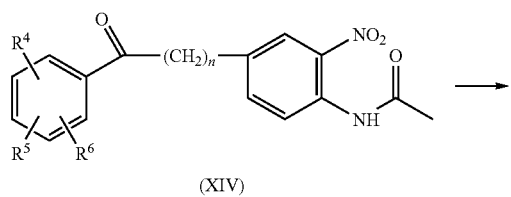

(XIV)

→

(XIII)

Intermediates of formula (X) can conveniently be prepared by reacting an aniline of formula (XV) with a halide of formula (XVI) in the presence of a base such as pyridine in a suitable solvent such as dichloromethane.

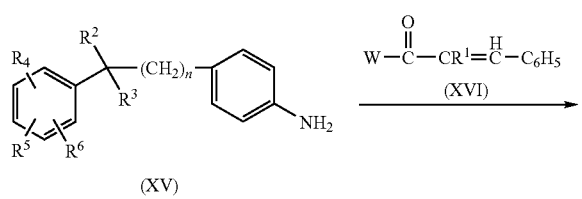

(XV)

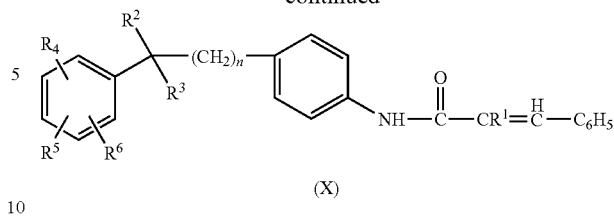

(X)

Intermediates of formula (VIII) wherein $R^2$ is hydrogen or hydroxy and when $R^2$ is hydrogen then $R^3$ is hydroxy herein referred to as intermediates of formula (VIII-a) can be prepared by treating an intermediate of formula (XVII), wherein W is halo, with an organolithium reagent such as, e.g. n-butyllithium in a reaction inert solvent, e.g. tetrahydrofuran, and subsequently reacting said intermediate with an intermediate of formula (XVIII) wherein $R^i$ is hydrogen or a radical as defined in $R^3$.

(XVII)        (XVIII)

(VIII-a)

The present invention also relates to a compound of formula (VII), wherein n is 0, X is $CR^7$ and $R^e$ and $R^d$ have the meanings as defined below, herein referred to as compounds of formula (VII-a)

(VII-a)

the N-oxide forms, the addition salts and the stereo-chemically isomeric forms thereof,
wherein
$R^1$, $R^4$, $R^5$, $R^6$, $R^7$ and aryl are as defined for the compounds of formula (I);
$R^e$ is hydrogen or taken together with $R^d$ may form a bivalent radical of formula —$(CH_2)_2$—$NR^{15}$—$(CH_2)_2$—  (e-1), or —$CH_2$—$NR^{16}$—$(CH_2)_3$—  (e-2), wherein $R^{15}$ and $R^{16}$ are each independently selected from hydrogen, $C_{1-6}$alkyl,

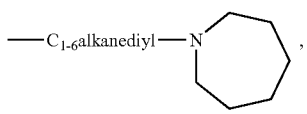

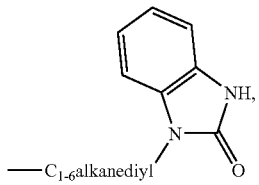

$C_{1-6}$alkyloxy$C_{1-6}$alkyl, piperidinyl$C_{1-6}$alkyl, $C_{3-10}$cycloalkyl$C_{1-6}$alkyl, aryloxy(hydroxy)$C_{1-6}$alkyl, aryl$C_{1-6}$alkyl, or aryl$C_{2-6}$alkenyl; or $R^d$ is di($C_{1-6}$alkyl)amino$C_{1-6}$alkyl or piperidinyl$C_{1-6}$alkyl.

A first group of interesting compounds of formula (VII-a) consists of those compounds of formula (VII-a) wherein one or more of the following restrictions apply:

a) $R^1$ is $C_{1-6}$alkyl;
b) $R^{15}$ and $R^{16}$ are each independently selected from hydrogen, $C_{1-6}$alkyl,

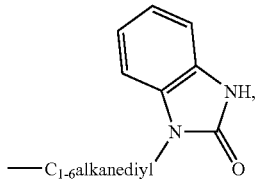

aryloxy(hydroxy)$C_{1-6}$alkyl, aryl$C_{1-6}$alkyl, or aryl$C_{2-6}$alkenyl;

c) $R^4$, $R^5$ and $R^6$ are each independently selected from hydrogen or halo;
d) when $R^5$ and $R^6$ are on adjacent positions they may taken together form a bivalent radical of formula (b-2) or (b-4); and
e) aryl is phenyl or phenyl substituted with halo or $C_{1-6}$alkyloxy.

A second group of interesting compounds of formula (VII-a) consists of those compounds of formula (VII-a) wherein one or more of the following restrictions apply:

a) $R^1$ is $C_{1-6}$alkyl;
b) $R^e$ is hydrogen or taken together with $R^d$ may form a bivalent radical of formula (e-1);
c) $R^{15}$ and $R^{16}$ are each independently selected from hydrogen or aryl$C_{2-6}$alkenyl;
d) $R^4$, $R^5$ and $R^6$ are each independently selected from hydrogen;
e) when $R^5$ and $R^6$ are on adjacent positions they may taken together form a bivalent radical of formula (b-2); and
e) aryl is phenyl substituted with halo or $C_{1-6}$alkyloxy.

A group of preferred compounds consists of those compounds of formula (VII-a) wherein $R^1$ is $C_{1-6}$alkyl; when $R^e$ is a radical of formula (a-1) or (a-2) then $R^{15}$ and $R^{16}$ are each independently selected from hydrogen, $C_{1-6}$alkyl,

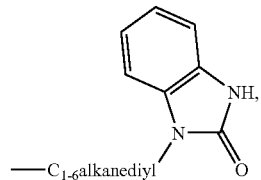

aryloxy(hydroxy)$C_{1-6}$alkyl, aryl$C_{1-6}$alkyl, or aryl$C_{2-6}$alkenyl; $R^4$, $R^5$ and $R^6$ are each independently selected from hydrogen or halo or when $R^5$ and $R^6$ are on adjacent positions they may taken together form a bivalent radical of formula (b-2) or (b-4); and aryl is phenyl or phenyl substituted with halo or $C_{1-6}$alkyloxy.

A further group of preferred compounds consists of those compounds of formula (VII-a) wherein $R^1$ is $C_{1-6}$alkyl; $R^e$ is hydrogen or taken together with $R^d$ may form a bivalent radical of formula (a-1); $R^{15}$ and $R^{16}$ are each independently selected from hydrogen or aryl$C_{2-6}$alkenyl; $R^4$, $R^5$ and $R^6$ are each independently selected from hydrogen or when $R^5$ and $R^6$ are on adjacent positions they may taken together form a bivalent radical of formula (b-2); and aryl is phenyl substituted with halo or $C_{1-6}$alkyloxy.

Compounds of formula (VII-a-1), defined as compounds of formula (VII-a), wherein $R^e$ taken together with $R^d$ forms a bivalent radical of formula (e-1) or (e-2) (e.g. a bivalent radical of formula (e-1)) and $R^{15}$ or $R^{16}$ (e.g. $R^{15}$) are other than hydrogen, can be prepared by reacting a compound of formula (VII-a), wherein $R^e$ taken together with $R^d$ forms a bivalent radical of formula (c-1) or (c-2) (e.g. a bivalent radical of formula (e-1)) and $R^{15}$ or $R^{16}$ (e.g. $R^{15}$) are hydrogen, herein referred to as compounds of formula (VII-a-2), with an intermediate of formula (XIX) wherein W is an appropriate leaving group such as, for example, chloro, bromo, methanesulfonyloxy or benzenesulfonyloxy and $R^{15}$ or $R^{16}$ (e.g. $R^{15}$) are other than hydrogen. The reaction can be performed in a reaction-inert solvent such as, for example, sodium carbonate, potassium carbonate or triethylamine.

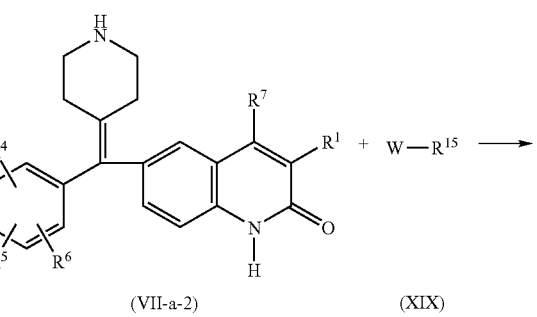

-continued

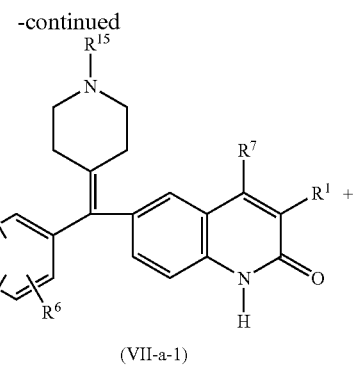

(VII-a-1)

Compounds of formula (VII-a) wherein $R^{15}$ or $R^{16}$ (e.g. $R^{15}$) are aryloxy(hydroxy)$C_{1-6}$alkyl, herein referred to as compounds of formula (VII-a-3), can be prepared by reacting a compound of formula (VII-a-2) with an intermediate of formula (XX) wherein R is an appropriate substituent in the presence of 2-propanol.

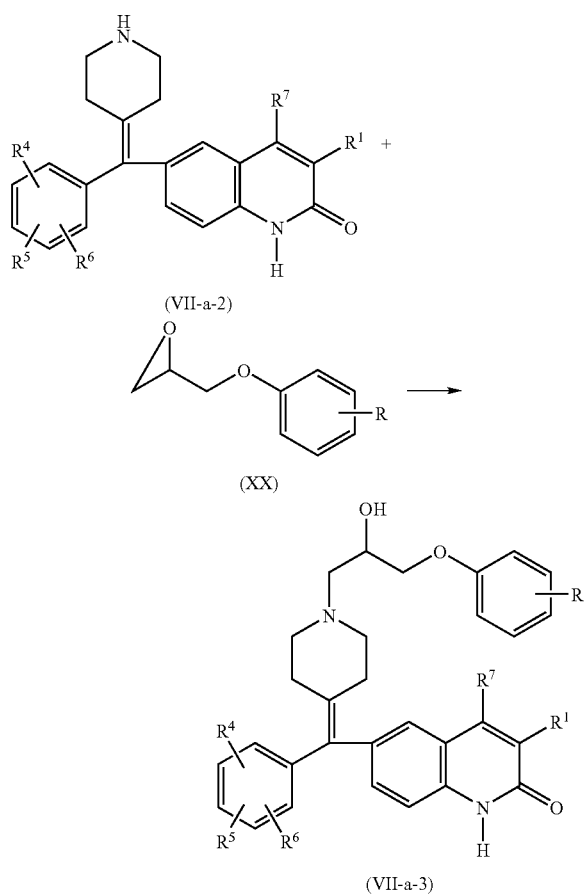

(VII-a-3)

The present invention also relates to compounds of formula (I) or formula (VII-a) as defined above for use as a medicine.

The compounds of the present invention have PARP inhibiting properties as can be seen from the experimental part hereinunder.

The present invention also contemplates the use of compounds in the preparation of a medicament for the treatment of one or more diseases and disorders in an animal described herein, wherein said compound is a compound of formula (I)

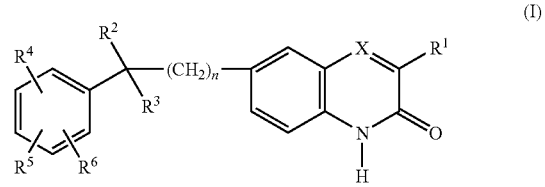

(I)

the N-oxide forms, the addition salts and the stereo-chemically isomeric forms thereof, wherein n is 0, 1 or 2;

X is N or $CR^7$, wherein $R^7$ is hydrogen or taken together with $R^1$ may form a bivalent radical of formula —CH=CH—CH=CH—;

$R^1$ is $C_{1-6}$alkyl or thiophenyl;

$R^2$ is hydrogen, hydroxy, $C_{1-6}$alkyl, $C_{3-6}$alkynyl or taken together with $R^3$ may form =O;

$R^3$ is a radical selected from

—$(CH_2)_s$—$NR^8R^9$ (a-1),

—O—H (a-2),

—O—$R^{10}$ (a-3),

—S—$R^{11}$ (a-4), or

—C≡N (a-5), wherein s is 0, 1, 2 or 3;

$R^8$, $R^{10}$ and $R^{11}$ are each independently selected from —CHO, $C_{1-6}$alkyl, hydroxy$C_{1-6}$alkyl, $C_{1-6}$alkylcarbonyl, amino, $C_{1-6}$alkylamino, di($C_{1-6}$alkyl)amino$C_{1-6}$alkyl, $C_{1-6}$alkyloxycarbonyl, $C_{1-6}$alkylcarbonylamino$C_{1-6}$alkyl, piperidinyl$C_{1-6}$alkylaminocarbonyl, piperidinyl, piperidinyl$C_{1-6}$alkyl, piperidinyl$C_{1-6}$alkylaminocarbonyl, $C_{1-6}$alkyloxy, thiophenyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, aryl$C_{1-6}$alkyl($C_{1-6}$alkyl)amino$C_{1-6}$alkyl, and $R^9$ is hydrogen or $C_{1-6}$alkyl;

or $R^3$ is a group of formula

—$(CH_2)_t$—Z (b-1), wherein t is 0, 1, 2 or 3;

—Z is a heterocyclic ring system selected from

(c-1)

(c-2)

-continued

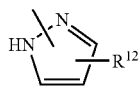 (c-3)

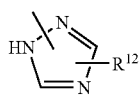 (c-4)

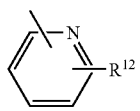 (c-5)

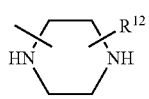 (c-6)

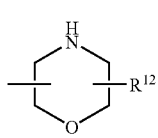 (c-7)

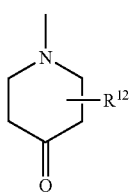 (c-8)

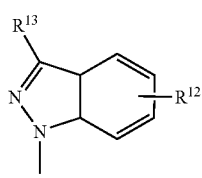 (c-9)

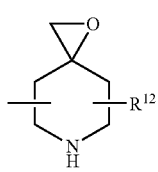 (c-10)

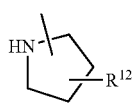 (c-11)

wherein $R^{12}$ is hydrogen, halo, $C_{1-6}$alkyl, aminocarbonyl, amino, hydroxy, aryl,

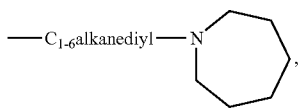,

-continued

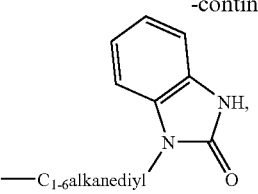

$C_{1-6}$alkylamino$C_{1-6}$alkyloxy, $C_{1-6}$alkyloxy$C_{1-6}$alkyl, $C_{1-6}$alkyloxy$C_{1-6}$alkylamino, aryl$C_{1-6}$alkyl, di(phenyl$C_{2-6}$alkenyl), piperidinyl, piperidinyl$C_{1-6}$alkyl, $C_{3-10}$cycloalkyl, $C_{3-10}$cycloalkyl$C_{1-6}$alkyl, aryloxy(hydroxy)$C_{1-6}$alkyl, haloindazolyl, aryl$C_{1-6}$alkyl, aryl$C_{2-6}$alkenyl, aryl$C_{1-6}$alkylamino, morpholino, $C_{1-6}$alkylimidazolyl, pyridinyl$C_{1-6}$alkylamino; and $R^{13}$ is hydrogen, piperidinyl or aryl;

$R^4$, $R^5$ and $R^6$ are each independently selected from hydrogen, halo, trihalomethyl, trihalomethoxy, $C_{1-6}$alkyl, $C_{1-6}$alkyloxy, amino, amino$C_{1-6}$alkyl, di($C_{1-6}$alkyl)amino, di($C_{1-6}$alkyl)amino$C_{1-6}$alkyloxy or $C_{1-6}$alkyloxycarbonyl, or $C_{1-6}$alkyl substituted with 1, 2 or 3 substituents independently selected from hydroxy, $C_{1-6}$alkyloxy, or amino$C_{1-6}$alkyloxy; or when $R^5$ and $R^6$ are on adjacent positions they may taken together form a bivalent radical of formula —O—CH$_2$—O— (d-1), —O—(CH$_2$)$_2$—O— (d-2), —CH═CH—CH═CH— (d-3), or —NH—C(O)—NR$^{14}$═CH— (d-4), wherein $R^{14}$ is $C_{1-6}$alkyl;

aryl is phenyl, phenyl substituted with halo, $C_{1-6}$alkyl or $C_{1-6}$alkyloxy.

The present invention also contemplates the use of compounds of formula (I) in the preparation of a medicament for the treatment of one or more diseases and disorders in an animal described herein, wherein the compound is a compound of formula (I-k)

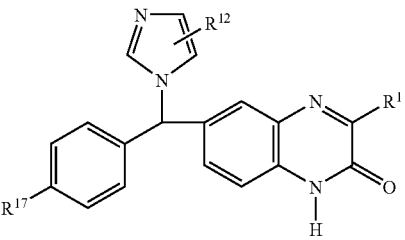 (I-k)

the N-oxide forms, the addition salts and the stereo-chemically isomeric forms thereof, wherein n is 0;

X is N;

$R^1$ is methyl or ethyl;

$R^2$ is hydrogen;

$R^3$ is a group of formula (b-1);

t is 0;

—Z is the heterocyclic ring system (c-2) wherein said heterocyclic ring system —Z is attached to the rest of the molecule with a nitrogen atom;

$R^{12}$ is hydrogen or $C_{1-6}$alkyl; and $R^{17}$ is halo or $C_{1-6}$alkyloxy or when $R^1$ is ethyl than $R^{17}$ can be hydrogen.

More in particular the compound of formula (I-k) is 6-[(1H-imidazol-1-yl)(4-methoxyphenyl)methyl]-3-methyl-2(1H)-quinoxalinone (compound No. 128), 3-ethyl-6-(1H-imidazol-1-ylphenylmethyl)-2(1H)-quinoxalinone (compound No. 127) and 6-[(4-chlorophenyl)-1H-imidazol-1-ylmethyl]-3-methyl-2(1H)-quinoxalinone (compound No. 146).

The present invention also contemplates the use of compounds of formula (VII-a) in the preparation of a medicament for the treatment of one or more diseases and disorders in an animal described herein The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; or chemosensitize and/or radiosensitize (hypoxic) tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) and the compounds of formula (VII-a) for inhibiting PARP activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tmors and cancerous cells. Chemotherapy treatment of other diseases not listed herein are also contemplated by the present invention.

The compounds, compositions and methods of the present invention are particularly useful for treating or preventing tissue damage resulting from cell death or damage due to necrosis or apoptosis.

The compounds of the present invention can be "anticancer agents", which term also encompasses "anti-tumor cell growth agents" and "anti-neoplastic agents". For example, the methods of the invention are useful for treating cancers and chemosensitizing and/or radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma gallbladder cancer, hairy cell leukemia, head &neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva and Wilm's tumor.

Hence, the compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemothearpeutic agents which act on the tumor or other therapueutically effective compounds for treating cancer or other disease. Examples of additional therapeutical agents that may be used in conjunction with chemosensitizers include, but are not limited to: methylating agents, toposisomerase I inhibitors and other chemothearpeutic agents such as cisplatin and bleomycin.

The compounds of formula (I) and the compounds of formula (VII-a) can also be used to detect or identify the PARP, and more in particular the PARP-1 receptor. For that purpose the compounds can be labeled. Said label can be selected from the group consisting of a radioisotope, spin label, antigen label, enzyme label fluorescent group or a chemiluminiscent group.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples illustrate the present invention.

Experimental Part

Hereinafter, "BuLi" is defines as butyl-lithium, "MeOH" is defined as methanol, "DIPE" is defined as diisopropyl ether, "DMF" is defined as N,N-dimethylformamide, "DCM" is defined as dichloromethane, "DMSO" is defined as dimethylsulfoxide, "EtOAc" is defined as ethyl acetate, "THF" is defined as tetrahydrofuran, "MEK" is defined as methyl ethyl keton.

A. Preparation of the Intermediate Compounds

Example A1 a) Preparation of Intermediate 1

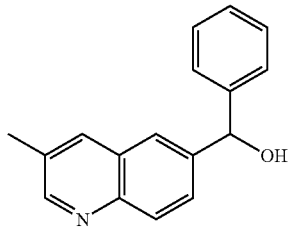

A solution of bromo-benzene (0.316 mol) in diethyl ether was added dropwise to a solution of Mg turnings (0.316 mol) in diethyl ether at room temperature and the mixture was stirred for 1 h 30 min. The mixture was cooled to 0° C., 3-methyl-6-quinolinecarboxaldehyde (0.263 mol) in THF (200 ml) was added dropwise and the mixture was stirred for 2 h. The mixture was poured into a saturated aqueous ammonium chloride solution and extracted with DCM. The organic layer was dried (MgSO$_4$), filtered off and evaporated till dryness. The residue (65.65 g) was crystallized from DIPE. The product was used without further purification, yielding 45.92 g (70%) of intermediate 1.

b) Preparation of Intermediate 2

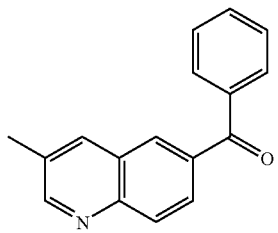

Potassium permanganate (0.24 mol) was added portionwise to a solution of intermediate 1 (0.16 mol) in DCM (300 ml) and triethanolamine tris(2-methoxyethyl) ether (5 ml) and the mixture was stirred for 2 h. The mixture was filtered through celite and evaporated till dryness, yielding 35 g (88%) of intermediate 2.

c) Preparation of Intermediate 3

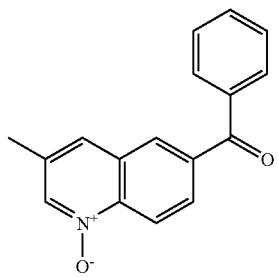

A solution of intermediate 2 (0.142 mol) in DCM (200 ml) was added dropwise to a solution of 3-chloro-benzenecarboperoxoic acid (0.283 mol) in DCM at room temperature and the mixture was stirred for 12 h. The mixture was poured into water, basified with potassium carbonate and extracted with DCM. The organic layer was dried (MgSO$_4$), filtered off and evaporated till dryness, yielding 32.68 g (87%) of intermediate 3.

d) Preparation of Intermediate 4

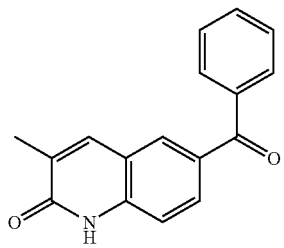

Tosyl chloride (0.145 mol) was added portionwise to a mixture of intermediate 3 (0.121 mol) in DCM (300 ml) and potassium carbonate 10% (665 ml) and the mixture was stirred for 1 h 30 min. DCM and water were added, the mixture was filtered through celite and extracted with DCM. The organic layer was dried (MgSO$_4$), filtered off and evaporated till dryness. The residue (36.43 g) was purified by column chromatography over silica gel (eluent: DCM/MeOH 98/2). The pure fractions were collected and evaporated. The residue (4.09 g) was crystallized from 2-propanone, yielding 1.67 g (5%) of intermediate 4, melting point 264.6° C.

e) Preparation of Intermediate 5

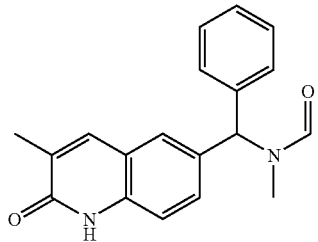

A mixture of intermediate 4 (0.037 mol) and N-methylformamide (1.85 mol) in formic acid (15 ml) was stirred and heated at 160° C. for 48 h. The mixture was cooled to room temperature, poured into ice water, basified with potassium carbonate 10% and extracted with EtOAc. The organic layer was dried (MgSO$_4$), filtered off and evaporated. The residue was crystallized from diethyl ether. A part (3 g) of the residue (7 g) was recrystallized from DCM/diethyl ether, yielding 2.15 g of intermediate 5, melting point 189.8° C.

Example A2 a) Preparation of Intermediate 6

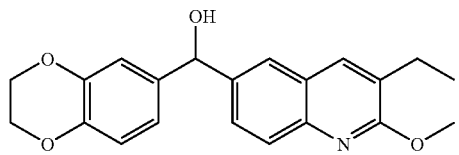

nBuLi 1.6M in hexane (0.0382 mol) was added dropwise at −60° C. under N₂ flow to a mixture of 6-bromo-3-ethyl-2-methoxy-quinoline (0.03 mol) in THF (50 ml). The mixture was stirred at −60° C. for 1 hour. A solution of 2,3-dihydro-1,4-benzodioxin-6-carboxaldehyde (0.0361 mol) in THF (50 ml) was added dropwise. The mixture was stirred at −60° C. for 2 hours, then at −40° C. for 1 hour, poured out into water and ammonium hydroxide and extracted with DCM. The organic layer was separated, dried (MgSO₄), filtered and the solvent was evaporated. The product was used without further purification, yielding 10.56 g of intermediate 6.

b) Preparation of Intermediate 7

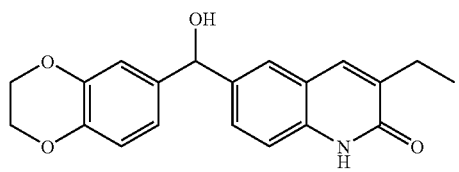

A mixture of intermediate 6 (0.0398 mol) in hydrochloric acid 3N (100 ml) and THF (20 ml) was stirred at 60° C. for 12 hours, then poured out into ice water and ammonium hydroxide and extracted with DCM. The organic layer was separated, dried (MgSO₄), filtered and the solvent was evaporated. The residue was taken up in 2-propanone and DIPE, filtered off and dried, yielding 6.2 g (47%) of intermediate 7, melting point 232° C.

Example A3 a) Preparation of Intermediate 8

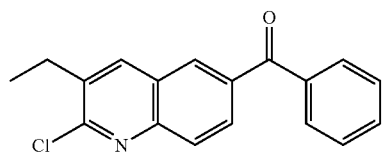

nBuLi 1.6M (0.102 mol) was added dropwise at −78° C. to a solution of 6-bromo-2-chloro-3-ethyl-quinoline (0.085 mol) in THF (200 ml) under N₂ flow. The mixture was stirred at −78° C. for 1 hour. A solution of N-methoxy-N-methyl-benzamide (0.085 mol) in THF (50 ml) was added dropwise at −78° C. The mixture was stirred from −78° C. to 0° C. for 2 H 30 min, hydrolysed with water and extracted with EtOAc. The organic layer was separated, dried (MgSO₄), filtered, and the solvent was evaporated. The residue was purified by column chromatography over silica gel (15-35 μm) (eluent: cyclohexane/EtOAc 93/7). The pure fractions were collected and the solvent was evaporated. The residue (7.5 g, 30%) was crystallized from 2-propanone. The precipitate was filtered off and dried, yielding 7.15 g (28%) of intermediate 8, melting point 94° C.

b) Preparation of Intermediate 9

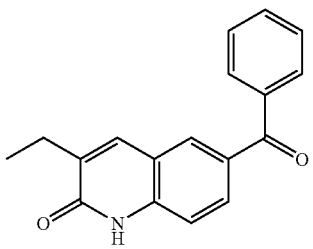

A mixture of intermediate 8 (0.169 mol) in hydrochloric acid 3N (250 ml) was stirred and refluxed for 12 h. The mixture was cooled to room temperature and filtered off. The precipitate was washed with water, then with 2-propanone and then with diethyl ether. The product was used without further purification, yielding 26 g (55%) of intermediate 9.

c) Preparation of Intermediate 10

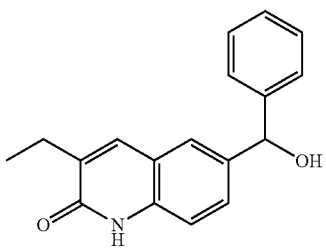

Sodium hydroborate (0.018 mol) was added portionwise at 0° C. under N₂ to a solution of intermediate 9 (0.018 mol) in MeOH (100 ml), the mixture was stirred at 5° C. for 1 h and then at room temperature for 1 h. The mixture was poured into ice water and filtered off. The precipitate was washed with 2-propanone and diethyl ether and it was recrystallized from 2-propanone/MeOH, yielding 2.62 (52%) of intermediate 10, melting point 235.7° C.

Example A4 a) Preparation of Intermediate 11

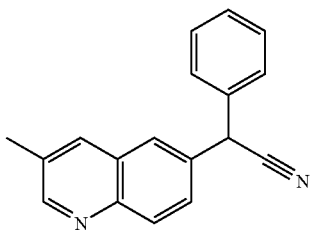

2-methyl-2-propanol, potassium salt (0.21 mol) and then MeOH (10.5 ml) were added at 0° C. to a solution of tosyl-methyl isocyanide (0.085 mol) in DMSO (300 ml). Intermediate 2 (0.06 mol) was added at 5° C. and the mixture was stirred at 5° C. for 1 h. The mixture was poured into ice water and extracted with DCM. The organic layer was washed with a hydrocloric acid 3N solution and evaporated till dryness.

The residue was recrystallized from diethyl ether, yielding 6.3 g (40%) of intermediate 11.

b) Preparation of Intermediate 12

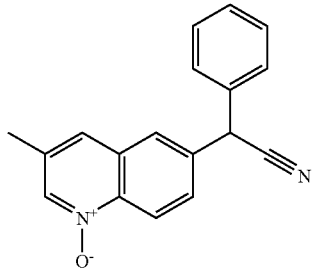

A solution of 3-chloro-benzenecarboperoxoic acid (0.048 mol) in DCM was added at 0° C. to a solution of intermediate 11 (0.024 mol) in DCM and the mixture was stirred at room temperature for 12 h. The mixture was washed with potassium carbonate 10% and extracted with DCM. The organic layer was dried (MgSO$_4$), filtered off and evaporated, yielding 6.28 g (94%) of intermediate 12.

Example A5 a) Preparation of Intermediate 13

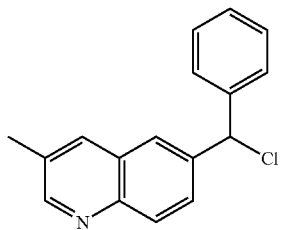

A solution of intermediate 1 (0.08 mol) in DCM (300 ml) was cooled till 0° C. Thionyl chloride (0.4 mol) was added dropwise and the mixture was stirred at room temperature for 12 h. The mixture was poured into ice water, basified with ammonium hydroxide and extracted with DCM. The organic layer was dried (MgSO$_4$), filtered off and evaporated till dryness. The product was used without further purification, yielding 21.5 g of intermediate 13.

b) Preparation of Intermediate 14

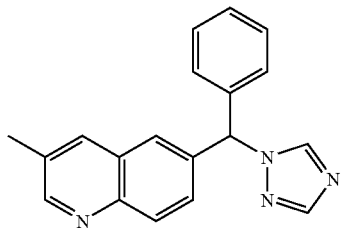

A mixture of intermediate 13 (0.08 mol), 1-H-1,2,4-triazole (0.24 mol) and potassium carbonate (0.24 mol) in acetonitrile (200 ml) was stirred and heated at 80° C. for 48 h. The mixture was poured into water and extracted with DCM. The organic layer was dried (MgSO$_4$), filtered off and evaporated till dryness. The residue (25.22 g) was purified by column chromatography over silica gel (eluent: DCM/MeOH 97/3).

The pure fractions were collected and evaporated, yielding 14.3 g (60%) of intermediate 14.

c) Preparation of Intermediate 15

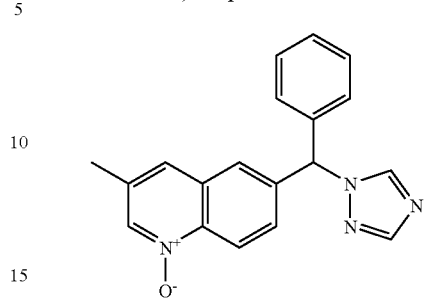

A solution of intermediate 14 (0.043 mol) and 3-chloro-benzenecarboperoxoic acid (0.086 mol) in DCM (150 ml) was stirred at room temperature for 12 h. The mixture was poured into water, basified with ammonium hydroxide and extracted with DCM. The organic layer was dried (MgSO$_4$), filtered off and evaporated till dryness. The product was used without further purification, yielding 14 g of intermediate 15.

Example A6 a) Preparation of Intermediate 16

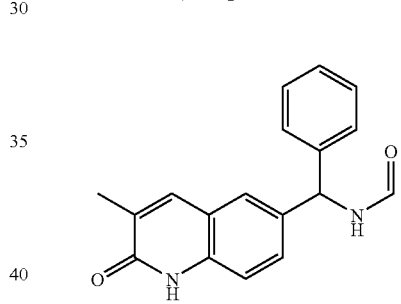

A mixture of intermediate 4 (0.076 mol) in formamide (300 ml) and formic acid (100 ml) was stirred at 160° C. for a weekend and poured out into ice water. The precipitate was filtered, rinsed with water then with diethyl ether and dried. The residue was crystallized from DCM/MeOH. The precipitate was filtered off and dried, yielding 14.5 g (65%) of intermediate 16, melting point >260° C.

b) Preparation of Intermediate 17 and 18 intermediate 17

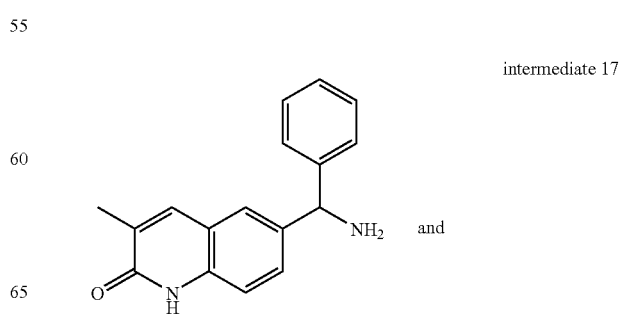

and

-continued intermediate 18

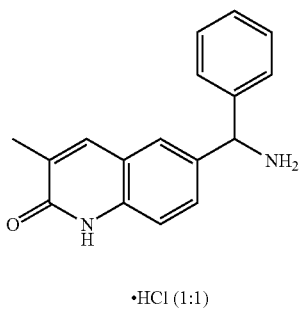

•HCl (1:1)

A mixture of intermediate 16 (0.044 mol) in hydrochloric acid 6N (290 ml) was stirred at 100° C. for 4 hours and 30 minutes, then brought to room temperature. The precipitate was filtered, washed with water, then with diethyl ether and dried, yielding 13.5 g (100%) of intermediate 18 as a monohydrochloride salt, melting point >260° C. Part of this fraction (11.8 g) was basified with sodium hydroxide and extracted with DCM. The organic layer was separated, dried (MgSO₄), filtered and the solvent was evaporated. yielding 9.95 g of intermediate 17.

Example A7

Preparation of Intermediate 19

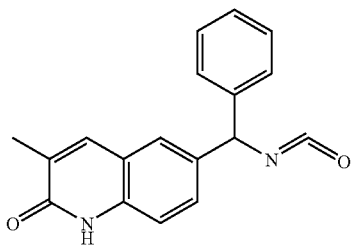

A mixture of 1,1'-carbonylbis-1H-imidazole (0.0794 mol) in THF (100 ml) was stirred at room temperature for 15 min. A mixture of intermediate 18 (0.0265 mol) in THF (100 ml) was added slowly. The mixture was stirred at room temperature for 2 hours. The product was used without further purification, yielding 7.7 g (100%) of intermediate 19.

Example A8 a) Preparation of Intermediate 20

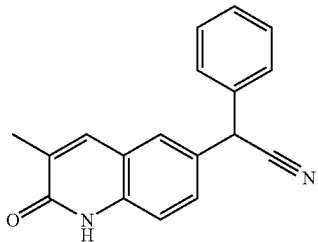

A mixture of intermediate 12 (0.022 mol) and tosyl chloride (0.033 mol) in potassium carbonate 10% (100 ml) and DCM (100 ml) was stirred at room temperature for 1 h. The mixture was extracted with DCM. The organic layer was dried (MgSO₄), filtered off and evaporated. The residue was recrystallized from diethyl ether, yielding 5 g (84%) of intermediate 20, melting point 227.5° C.

b) Preparation of Intermediate 21

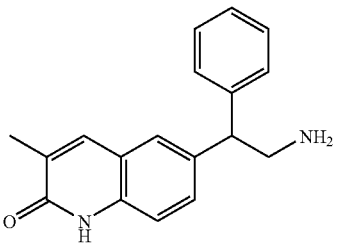

Intermediate 20 (0.015 mol) in MeOH/NH₃ 7N (100 ml) was hydrogenated with Raney Nickel (4 g) as a catalyst at room temperature over a 6 h period under a 3 bar pressure and the flask was flushed with N₂. After uptake of H₂ (2 eq), the catalyst was filtered off and the filtrate was evaporated. The residue was purified by column chromatography over silica gel (eluent: DCM/MeOH/NH₄OH 90/10/0.1). The pure fractions were collected and evaporated, yielding 3 g (73%) of intermediate 21.

Example A9 a) Preparation of Intermediate 22

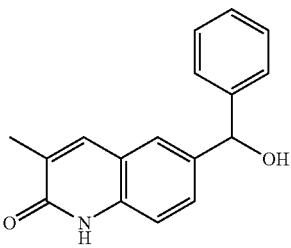

Sodium hydroborate (0.15 mol) was added portionwise at 5° C. under N₂ to a mixture of intermediate 4 (0.075 mol) in MeOH (500 ml) and THF (500 ml). The mixture was stirred at 5° C. for 1 h and then at room temperature for 1 h. The mixture was poured into ice and extracted with DCM. The organic layer was dried (MgSO₄), filtered off and evaporated. A part (3 g) of the residue (36.82 g, 92%) was recrystallized from diethyl ether and THF, yielding 2 g of intermediate 22, melting point 237.7° C.

b) Preparation of Intermediate 23

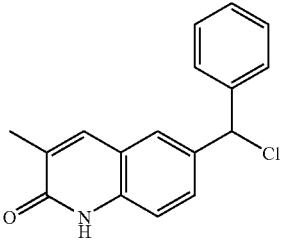

Thionyl chloride (10 ml) was added dropwise to a solution of intermediate 22 (0.0162 mol) in DCM (200 ml) at 0° C. When the addition was complete, the mixture was stirred at room temperature for 12 h. The mixture was evaporated in vacuo and the product was used without further purification, yielding 4.6 g (100%) of intermediate 23.

Example A10 a) Preparation of Intermediate 24

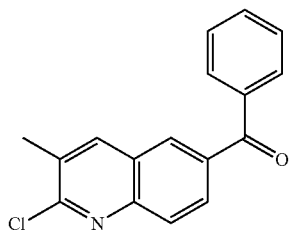

A mixture of intermediate 4 (0.076 mol) in phosphoryl chloride (60 ml) was stirred at 60° C. for 5 h. The mixture was evaporated till dryness, the residue was taken up in ice, basified with NaHCO$_3$ and extracted with EtOAc. The organic layer was dried (MgSO$_4$), filtered off and evaporated. The product was used without further purification, yielding 18 g (86%) of intermediate 24.

b) Preparation of Intermediate 25

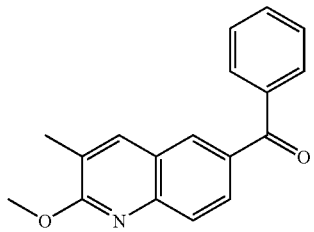

Sodium methylate (0.16 mol) was added to a solution of intermediate 24 (0.035 mol) in MeOH (100 ml) and the mixture was stirred and refluxed for 5 h. The mixture was cooled to room temperature, poured into ice water and extracted with EtOAc. The organic layer was dried (MgSO$_4$), filtered off and evaporated. The residue was crystallized from diethyl ether, yielding 7 g (72%) of intermediate 25.

c) Preparation of Intermediate 26

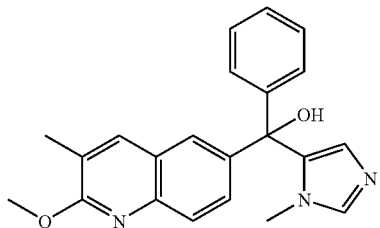

n-BuLi (0.0539 mol) was added slowly at −70° C. under N$_2$ flow to a solution of 1-methyl-1H-imidazole (0.0539 mol) in THF (80 ml). The mixture was stirred at −70° C. for 30 min. Chlorotriethyl-silane (0.0539 mol) was added. The mixture was allowed to warm to room temperature and then cooled to −70° C. n-BuLi (0.0539 mol) was added slowly. The mixture was stirred at −70° C. for 1 hour, then allowed to warm to −15° C. and cooled to −70° C. A solution of intermediate 25 (0.0414 mol) in THF (50 ml) was added. The mixture was allowed to warm to room temperature and then stirred at room temperature overnight. Water was added. The mixture was extracted with EtOAc. The organic layer was separated, dried (MgSO$_4$), filtered and the solvent was evaporated. The residue (28 g) was purified by column chromatography over silica gel (20-45 μm) (eluent: DCM/MeOH/NH$_4$OH 96.5/3.5/0.1). The pure fractions were collected and the solvent was evaporated, yielding 9.7 g (65%) of intermediate 26.

Example A11 a) Preparation of Intermediate 27

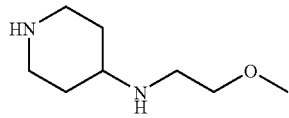

A mixture of N-(2-methoxyethyl)-1-(phenylmethyl)-4-piperidinamine (0.0402 mol) in ethanol (100 ml) was hydrogenated at 40° C. for 2 hours in a and then at room temperature under a 3 bar pressure for 3 hours with Pd/C 10% (1 g) as a catalyst. After uptake of H$_2$ (1 equiv), the catalyst was filtered through celite, washed with ethanol and the filtrate was evaporated. The product was used without further purification, yielding 6.5 g (99%) of intermediate 27.

b) Preparation of Intermediate 28

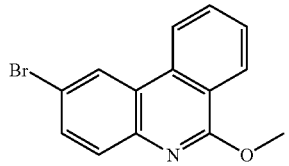

Sodium methylate 30% in MeOH (138 ml) was added to a mixture of 2-bromo-6-chloro-phenanthridine (0.124 mol) in MeOH (413 ml). The mixture was stirred and refluxed overnight, then poured out on ice and extracted with DCM. The precipitate was filtered off and dried. The filtrate was dried (MgSO$_4$), filtered and the solvent was evaporated. The residue (19.7 g) was purified by column chromatography over silica gel (20-45 μm) (eluent: DCM/cyclohexane 30/70). The pure fractions were collected and the solvent was evaporated, yielding 9.6 g (27%) of intermediate 28.

c) Preparation of Intermediate 29

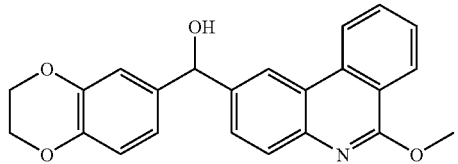

nBuLi 1.6M (0.028 mol) was added dropwise at −78° C. under N$_2$ flow to a mixture of intermediate 28 (0.014 mol) in THF (40 ml). The mixture was stirred at −78° C. for 1 hour. A mixture of 2,3-dihydro-1,4-benzodioxin-6-carboxaldehyde (0.0305 mol) in THF (40 ml) was added. The mixture was stirred at −78° C. for 1 hour, hydrolized and extracted with EtOAc. The organic layer was separated, dried (MgSO₄), filtered and the solvent was evaporated. The residue (11.2 g) was purified by column chromatography over silica gel (15-35 μm) (eluent: cyclohexane/EtOAc 70/30). The pure fractions were collected and the solvent was evaporated, yielding: 4 g (77%) of intermediate 29.

d) Preparation of Intermediate 30

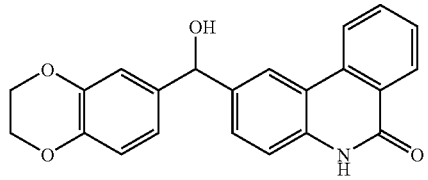

A mixture of intermediate 29 (0.0107 mol) in hydrochloric acid 3N (40 ml) and THF (10 ml) was stirred and refluxed overnight and poured out into water. The precipitate was filtered off and dried, yielding 3.7 g (97%) of intermediate 30.

e) Preparation of Intermediate 31

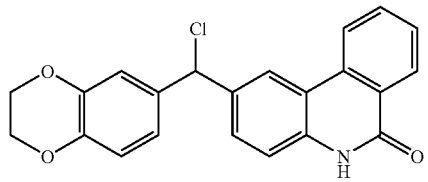

Thionyl chloride (10 ml) was added at room temperature to a mixture of intermediate 30 (0.0028 mol) in DCM (10 ml). The mixture was stirred at room temperature overnight. The solvent was evaporated till dryness. The product was used without further purification, yielding 1.3 g (quant.) of intermediate 31.

Example A12

Preparation of Intermediate 32

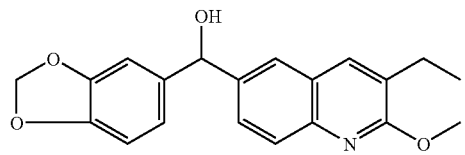

nBuLi 1.6M (0.0451 mol) was added slowly at −78° C. under N₂ flow to a solution of 6-bromo-3-ethyl-2-methoxy-quinoline (0.0376 mol) in THF (200 ml). The mixture was stirred for 90 min and cooled again to −78° C. A mixture of piperonylaldehyde (0.0376 mol) in THF (100 ml) was added dropwise. The mixture was stirred for 2 hours, poured out into water and ammonium chloride and extracted with EtOAc. The organic layer was separated, dried (MgSO₄), filtered and the solvent was evaporated till dryness. The residue (14.9 g) was purified by column chromatography over silica gel (15-35 μm) (eluent: DCM/MeOH 99/1). The pure fractions were collected and the solvent was evaporated. The residue was crystallized from diethyl ether. The precipitate was filtered off and dried, yielding 1 g of intermediate 32, melting point 116° C.

Example A13 a) Preparation of Intermediate 33

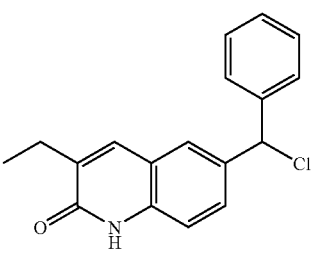

Thionyl chloride (0.069 mol) was added dropwise at 10° C. under N₂ to a solution of intermediate 10 (0.0183 mol) in DCM (50 ml) and the mixture was stirred at 10° C. for 1 h and at room temperature overnight. The mixture was evaporated and the residue was taken up in DCM. The mixture was alkalized with potassium carbonate 10% and extracted with DCM. The organic layer was dried (MgSO₄), filtered off and evaporated, yielding 5.10 g (94%) of intermediate 33.

b) Preparation of Intermediate 34

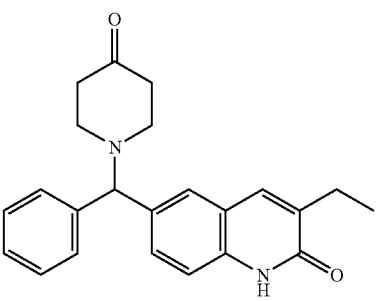

A mixture of 4,4-piperidinediol, hydrochloride (0.1974 mol) and potassium carbonate (0.396 mol) in DMF (150 ml) was stirred at 40° C. under N₂ flow for 15 min and then added quickly at 40° C. under N₂ flow to a solution of intermediate 33 (0.0987 mol) in DMF (150 ml). The mixture was stirred under N₂ flow for 12 hours. The solvent was evaporated till dryness. The residue was taken up in water and DCM, washed with hydrochloric acid 3N and decanted. The aqueous layer was basified with ammonium hydroxide and extracted with DCM. The combined organic layer was dried (MgSO₄), filtered and the solvent was evaporated. The residue (17 g) was purified by column chromatography over silica gel (15-40 μm) (eluent: DCM/MeOH/NH₄OH 97/25/0.5). The pure fractions were collected and the solvent was evaporated. The residue was crystallized from 2-propanone/DIPE. The precipitate was filtered off and dried, yielding 3.2 g of intermediate 34.

Example A14 a) Preparation of Intermediate 35

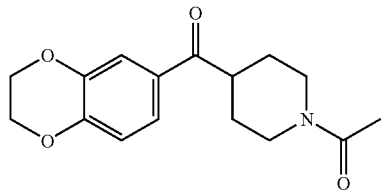

1-acetyl-4-piperidinecarbonyl chloride (0.1227 mol) was added slowly at 5° C. to a mixture of aluminum chloride (0.2699 mol) in 1,2-dichloro-ethane (25 ml). The mixture was heated to 65° C. 2,3-dihydro-1,4-benzodioxin (0.18405 mol) was added. The mixture was stirred at 65° C. for 15 hours, cooled to room temperature, poured out into water and extracted with DCM. The organic layer was separated, dried ($MgSO_4$), filtered and the solvent was evaporated till dryness. The residue (44.44 g) was purified by column chromatography over silica gel (15-35 μm) (eluent: DCM/MeOH 97.5/2.5). The pure fractions were collected and the solvent was evaporated. Part (0.2 g) of the residue (27 g, 76%) was crystallized from MEK and DIPE. The precipitate was filtered off and dried, yielding intermediate 35, melting point 102° C.

b) Preparation of Intermediate 36

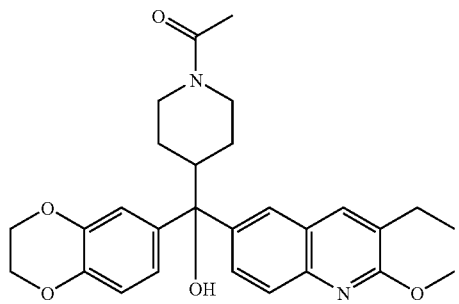

nBuLi 1.6M in hexane (0.09 mol) was added slowly at −78° C. under $N_2$ flow to a solution of 6-bromo-3-ethyl-2-methoxy-quinoline (0.075 mol) in THF (200 ml). The mixture was stirred for 1 hour. A mixture of intermediate 35 (0.075 mol) in THF (100 ml) was added dropwise at −78° C. The mixture was stirred at −30° C. for 2 hours, poured out into water and ammonium chloride and extracted with EtOAc. The organic layer was separated, dried ($MgSO_4$), filtered and the solvent was evaporated till dryness. The residue (37.1 g) was purified by column chromatography over silica gel (15-35 μm) (eluent: DCM/MeOH/$NH_4OH$ 97/3/0.15). The desired fractions were collected and the solvent was evaporated. The residue was crystallized from DIPE. The precipitate was filtered off and dried, yielding 0.8 g of intermediate 36, melting point 114° C.

c) Preparation of Intermediate 37

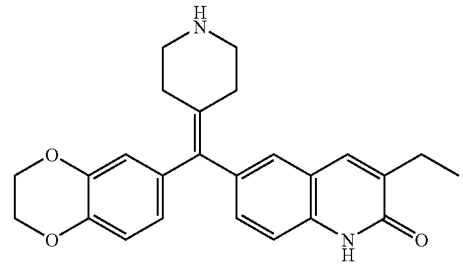

A mixture of intermediate 36 (0.0504 mol) in hydrochloric acid 3N (400 ml) and THF (200 ml) was stirred and refluxed for 12 hours, then poured out into ice water, basified with ammonium hydroxide and extracted with DCM. The organic layer was separated, dried ($MgSO_4$), filtered and the solvent was evaporated. The residue was purified by column chromatography over silica gel (eluent: DCM/MeOH/$NH_4OH$ 90/10/0.1). The pure fractions were collected and the solvent was evaporated. The residue was crystallized from DIPE. The precipitate was filtered off and dried, yielding 7.45 g (37%) of intermediate 37, melting point 249° C.

d) Preparation of Intermediate 38

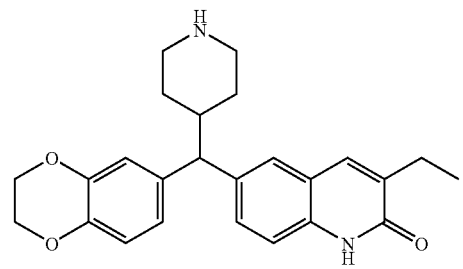

A mixture of intermediate 37 (0.015 mol) in MeOH (100 ml) was hydrogenated at 50° C. under 20 bar pressure for 15 hours with Pd/C 10% (1.3 g) as a catalyst. After uptake of $H_2$, the catalyst was filtered off. Hydrogenation was continued. After uptake of $H_2$, the catalyst was filtered off and the filtrate was evaporated till dryness. The residue (5.4 g) was purified by column chromatography over silica gel (15-40 μm) (eluent: DCM/MeOH/$NH_4OH$ 85/15/1). The desired fractions were collected and the solvent was evaporated, yielding 3.5 g (54%) of intermediate 38.

Example A15 a) Preparation of Intermediate 39

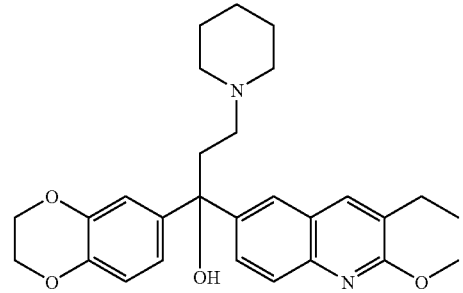

nBuLi 1.6M (0.02986 mol) was added at −78° C. under $N_2$ flow to a solution of 6-bromo-3-ethyl-2-methoxy-quinoline (0.02488 mol) in THF (120 ml). The mixture was stirred at −30° C. for 1 hour and cooled again to −70° C. A mixture of 1-(2,3-dihydro-1,4-benzodioxin-6-yl)-3-(1-piperidinyl)-1-propanone (0.02488 mol) in THF (60 ml) was added slowly. The mixture was stirred at −70° C. for 1 hour, poured out into water and ammonium chloride and extracted with EtOAc. The organic layer was separated, dried (MgSO$_4$), filtered and the solvent was evaporated till dryness. The residue (14.92 g) was purified by column chromatography over silica gel (15-35 μm) (eluent: DCM/MeOH/NH$_4$OH 94/6/0.1). The desired fractions were collected and the solvent was evaporated, yielding 7.2 g (63%) of intermediate 39.

b) Preparation of Intermediate 40, 41 and 42

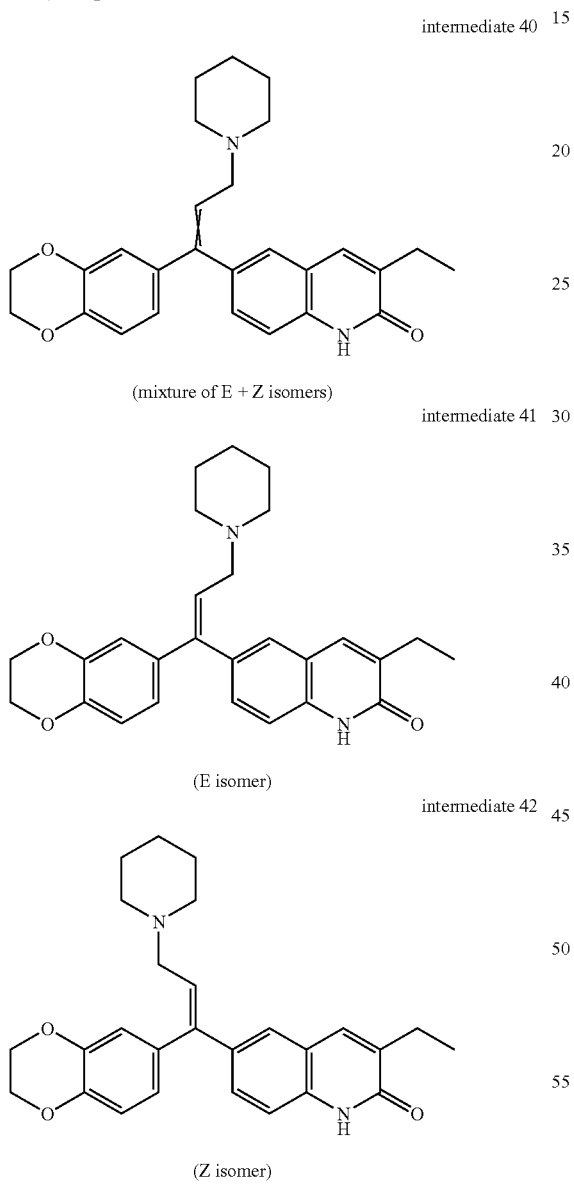

intermediate 40
(mixture of E + Z isomers)

intermediate 41
(E isomer)

intermediate 42
(Z isomer)

A mixture of intermediate 39 (0.0123 mol) in hydrochloric acid 6N (95 ml) and THF (38 ml) was stirred and refluxed for 15 hours, cooled to room temperature, poured out on ice, basified with a concentrated ammonium hydroxide solution and extracted with DCM. The organic layer was separated, dried (MgSO$_4$), filtered and the solvent was evaporated till dryness. The residue (13.6 g) was purified by column chromatography over silica gel (15-35 μm) (eluent: DCM/MeOH/NH$_4$OH 94/6/0.5). Three desired fractions were collected and their solvents were evaporated, yielding 2.1 g F1 (E isomer), 2 g F2 (Z isomer) and 0.67 g of intermediate 40 (mixture of E+Z isomers). Both F1 and F2 fractions were crystallized from 2-propanone. The precipitate was filtered off and dried, yielding 0.7 g of intermediate 41 (E) and 0.7 g of intermediate 42 (Z).

Example A16

Preparation of Intermediate 43

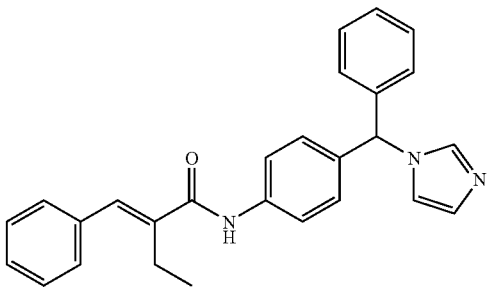

α-ethyl-cinnamoyl chloride (0.107 mol) was added at 0° C. to a solution of 4-(1H-imidazol-1-ylphenylmethyl)-benzenamine (0.089 mol) in pyridine (20 ml) and DCM (150 ml) and the mixture was stirred for 4 h. The mixture was evaporated till dryness, the residue was basified with ammonium hydroxide and extracted with DCM. The organic layer was dried (MgSO$_4$), filtered off and evaporated till dryness. The product was used without further purification, yielding intermediate 43.

Example A17 a) Preparation of Intermediate 44

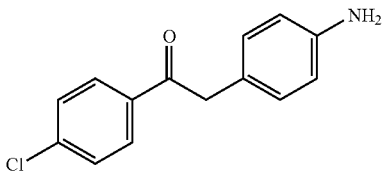

To a solution of 1-(4-chlorophenyl)-2-(4-nitrophenyl)-ethanone (0.09064 mol) in MeOH (500 ml), Raney Nickel (25 g) was added. The mixture was stirred under reduced pressure (3 bar) for 30 minutes. Then the hot reaction mixture was filtered off. The solvent was evaporated, yielding intermediate 44.

b) Preparation of Intermediate 45

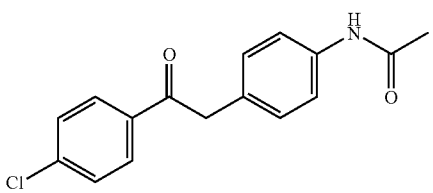

To a solution of intermediate 44 (0.252 mol) in DCM (600 ml), acetic acid, anhydride (71.5 ml) was added dropwise.

The mixture was stirred for 1 hour at room temperature. Then the mixture was poured on ice water, neutralized with concentrated ammonium hydroxide decanted, washed, dried, and the solvent was evaporated, yielding 72 g (99%) of intermediate 45, melting point 190° C.

c) Preparation of Intermediate 46

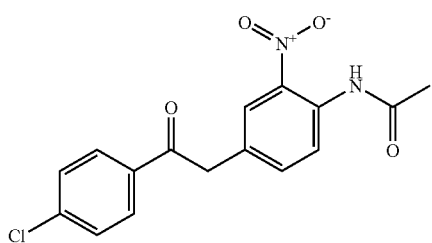

To a mixture of intermediate 45 (0.25 mol) in acetic acid, anhydride (500 ml) at room temperature, nitric acid (fuming) (39.6 ml) was added portionwise. The mixture was stirred for 1 hour. Then the mixture was poured on ice water, neutralized with concentrated ammonium hydroxide, filtered off, washed with MEK and dried, yielding 47 g (56.5%) of intermediate 46, melting point 145° C.

d) Preparation of Intermediate 47

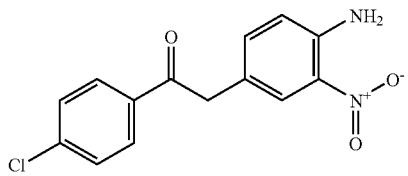

A mixture of intermediate 46 (0.1202 mol) in hydrochloric acid 3N (100 ml) and THF (300 ml) was stirred at 60° C. for 12 hours, poured out into water and extracted three times with DCM (3×80 ml). The organic layer was separated, dried (MgSO$_4$), filtered and the solvent was evaporated, yielding 34 g (97%) of intermediate 47, melting point 112° C.

e) Preparation of Intermediate 48

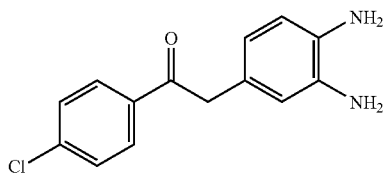

A mixture of intermediate 47 (0.0103 mol) in MeOH (350 ml) was hydrogenated at room temperature under a 3 bar pressure for 90 min with Raney Nickel (34 g) as a catalyst. After uptake of H$_2$ (3 equiv), the catalyst was filtered through celite, washed with MeOH and the filtrate was evaporated, yielding 23 g (75%) of intermediate 48, melting point 128° C.

f) Preparation of Intermediates 49 and 50

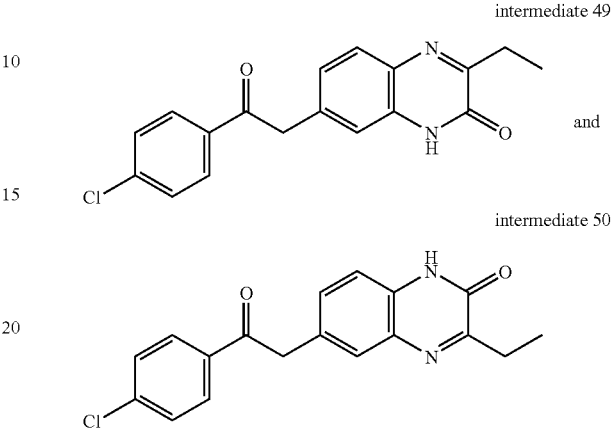

A mixture of intermediate 48 (0.0882 mol) in water (160 ml) was stirred at 0° C. A solution of 2-oxo-butanoic acid (0.112 mol) in acetic acid (70 ml) was added portionwise at 0° C. The mixture was allowed to warm to room temperature, then stirred at room temperature for 12 hours, poured out into water and sodium hydroxide 3N and extracted with DCM and MeOH. The organic layer was separated, dried (MgSO$_4$), filtered and the solvent was evaporated. The residue (33 g) was dissolved in DCM/MeOH/NH$_4$OH 97/3/0.1. A precipitate was filtered off (*) and crystallized twice from MeOH and DCM. The precipitate was filtered off and dried, yielding 0.64 g (3%) of intermediate 49, melting point 228° C. (*) The filtrate was purified by column chromatography over silica gel (20-45 µm) (eluent: DCM/MeOH/NH$_4$OH 97/3/0.1). The desired fractions were collected and the solvent was evaporated. The residue was crystallized from 2-propanone and diethyl ether. The precipitate was filtered off and dried, yielding 1.5 g (5%) of intermediate 50, melting point 236° C.

Example A18 a) Preparation of Intermediate 51

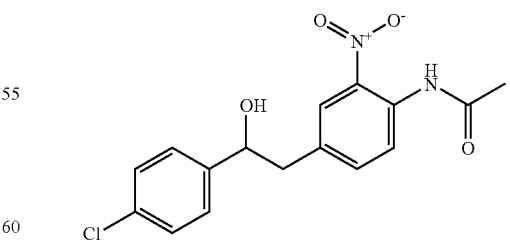

To a solution of intermediate 46 (0.141 mol) in MeOH (500 ml) cooled to 10° C., sodium hydroborate (0.0141 mol) was added portionwise. Then water was added and the precipitate filtered off, washed and dried, yielding 44 g of (93.2%) of intermediate 51.

b) Preparation of Intermediate 52

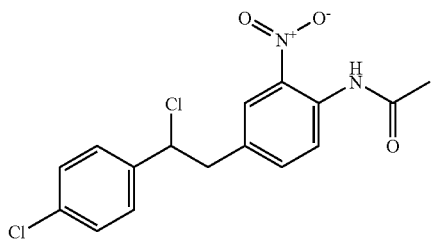

To a solution of intermediate 51 (0.131 mol) in DCM (400 mL), triethylamine (36.6 ml) was added. The mixture was cooled to 0° C. Then methanesulfonyl chloride (20.35 ml) was added dropwise. The mixture was stirred overnight at room temperature. Then the mixture was poured into ice water, decanted, washed, dried ($MgSO_4$) and the solvent was evaporated, yielding 58 g (100%) of intermediate 52.

c) Preparation of Intermediate 53

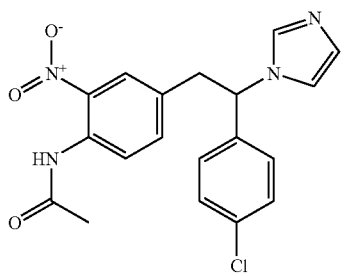

A mixture of intermediate 52 (0.131 mol) in acetonitrile (400 ml), 1H-imidazole (0.658 mol) and potassium carbonate (89.06 g) was stirred at 80° C. overnight. The solvent was evaporated till dryness and then the residue was taken up in DCM, decanted, washed, dried and the solvent was evaporated. The residue (35 g) was purified by column chromatography over silica gel (eluent: DCM/MeOH 98/2) yielding 13 g (27.6%) of intermediate 53, melting point 131° C.

d) Preparation of Intermediate 54

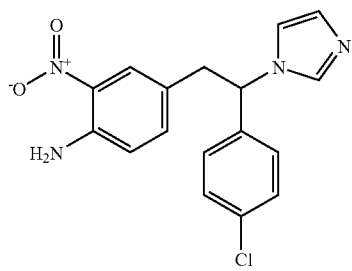

A mixture of intermediate 53 (0.0352 mol) in sodium hydroxide 2N (130 ml) and ethanol (13 ml) was stirred at room temperature for 24 hours, then the reaction mixture was neutralised with hydrochloric acid and extracted with DCM. The organic layer was washed with water, dried ($MgSO_4$), filtered off and the solvent was evaporated. The residue was crystallised from DIPE/2-propanone and the resulting precipitate was collected, yielding 10 g (82.8%) of intermediate 54, melting point 153° C.

e) Preparation of Intermediate 55

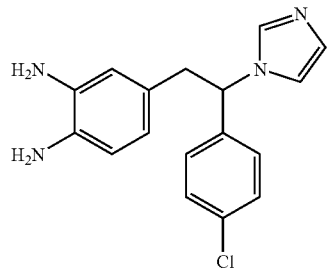

A mixture of intermediate 54 (0.0292 mol) in MeOH (100 ml) was hydrogenated at room temperature for 1 hour with Raney Nickel (10 g) as a catalyst. After uptake of $H_2$ (3 equiv.), the solution was filtered over a celite path and the solvent was evaporated (vac.), yielding 9.1 g of intermediate 55 (used as such in the next reaction step without further purification).

Example A19 a) Preparation of Intermediate 56

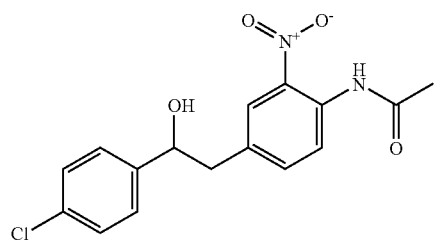

To a solution of intermediate 46 (0.141 mol) in MeOH (500 ml) cooled to 10° C., sodium hydroborate (0.0141 mol) was added portionwise. Then water was added and the precipitate filtered off, washed and dried, yielding 44 g (93.2%) of intermediate 56.

b) Preparation of Intermediate 57

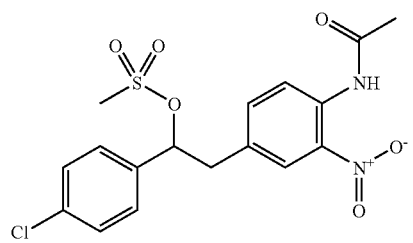

Methylsulfonyl chloride (0.048 mol) was added slowly at 0° C. to a solution of intermediate 56 (0.0239 mol) and triethylamine (0.048 mol) in DCM (80 ml). The mixture was allowed to warm to room temperature over a 4-hour period. The solvent was evaporated till dryness. The product was used without further purification, yielding intermediate 57.

c) Preparation of Intermediate 58

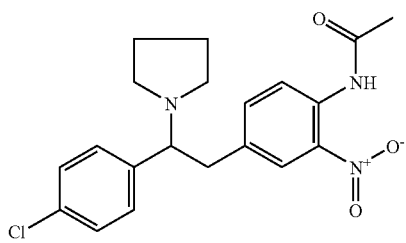

A mixture of intermediate 57 (0.0291 mol), pyrrolidine (0.0871 mol) and potassium carbonate (0.0868 mol) in acetonitrile (150 ml) was stirred and refluxed for 12 hours, then cooled, filtered, washed with acetonitrile, filtered again and the solvent was evaporated till dryness. The residue was taken up in DCM and water. The organic layer was separated, dried ($MgSO_4$), filtered and the solvent was evaporated. The residue (12 g) was purified by column chromatography over silica gel (15-40 μm) (eluent: DCM/MeOH/$NH_4OH$ 99/1/0.1). The pure fractions were collected and the solvent was evaporated, yielding 1.7 g (15%) of intermediate 58.

d) Preparation of Intermediate 59

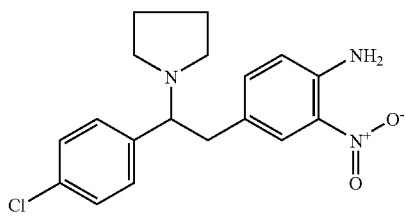

A mixture of intermediate 58 (0.00438 mol) in sodium hydroxide 3N (80 ml) and ethanol (20 ml) was stirred at room temperature for 12 hours, poured out into water and extracted with DCM. The organic layer was separated, dried ($MgSO_4$), filtered and the solvent was evaporated, yielding 1.2 g (80%) of intermediate 59.

e) Preparation of Intermediate 60

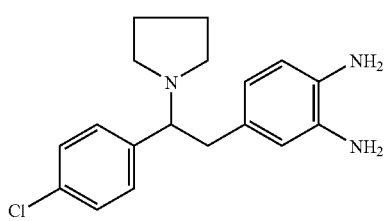

A mixture of intermediate 59 (0.00347 mol) in MeOH (80 ml) was hydrogenated at room temperature under a 3 bar pressure for 30 min with Raney Nickel (1.2 g) as a catalyst. After uptake of $H_2$ (3 equiv), the catalyst was filtered through celite, washed with MeOH and the filtrate was evaporated. The product was used without further purification, yielding 0.98 g of intermediate 60.

Example A20 a) Preparation of Intermediate 61

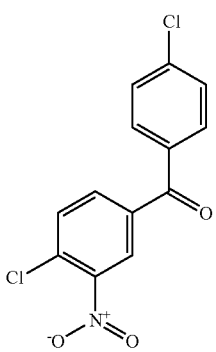

Reaction (I): A mixture of 4-chloro-3-nitro-benzoic acid (0.125 mol) in thionyl chloride (30 ml) and chloroform (60 ml) was stirred and refluxed for 4.5 hours and then the reaction mixture was concentrated to dryness, to give Residue (I). Reaction (II): Residue (I) was dissolved in chlorobenzene (65 ml) and the resulting solution was added dropwise under cooling (ice-bath) to a stirred suspension of aluminum chloride (0.188 mol) in chlorobenzene (65 ml). The reaction mixture was stirred overnight at room temperature and poured out into ice-water, then extracted with DCM. The extract was washed with a $NaHCO_3$ solution, and with water, then dried ($MgSO_4$) and concentrated (vac.) until dryness. The residue was crystallised from 2-propanol and the desired product was collected, yielding 23.7 g of intermediate 61, melting point 83.4° C.

b) Preparation of Intermediate 62

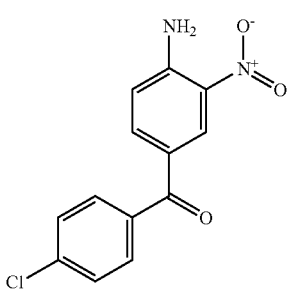

A mixture of intermediate 61 (0.06 mol) and $NH_3$ (10 g) in MeOH (180 ml) and thiophane dioxide (20 ml) was heated overnight in a pressure-tube at 120-130° C., then MeOH was distilled off under reduced pressure and the residue was stirred in a boiling, diluted hydrochloric acid solution. The mixture was cooled and the resulting precipitate was suctioned off, then washed with water and recrystallised from ethanol. Finally, the desired product was collected, yielding 12 g (72.3%) of intermediate 62, melting point 200.9° C.

c) Preparation of Intermediate 63

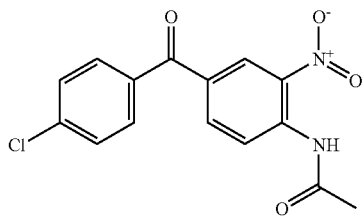

A mixture of intermediate 62 (0.0686 mol) in DCM (200 ml) and acetyl chloride (20 ml) was stirred for 12 hours at room temperature and then the solvent was evaporated dry. The residue was taken up in diethyl ether (50 ml), then the desired product was filtered off and dried, yielding 21.6 g (99%) of intermediate 63, melting point 138° C.

d) Preparation of Intermediate 64

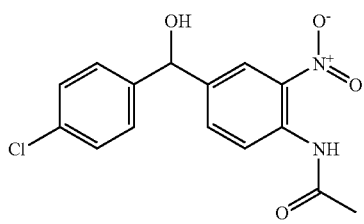

A mixture of intermediate 63 (0.066 mol) in MeOH (200 ml) was stirred at 0° C. and a solution of sodium hydroborate (0.066 mol) in water was added dropwise, then the reaction mixture was stirred for 1 hour at room temperature and the solvent was evaporated. The residue was extracted with DCM/MeOH/$H_2O$ and the extract was dried ($MgSO_4$). Finally the solvent was evaporated and the desired product was collected, yielding 20.4 g (97%) of intermediate 64, melting point 198° C.

e) Preparation of Intermediate 65

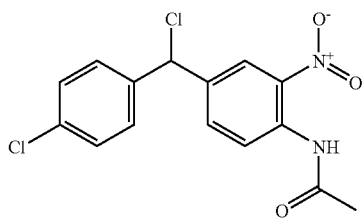

In a 3-neck reaction flask (500 ml), equipped with an addition funnel and thermometer, a mixture of intermediate 64 (0.062 mol) and triethylamine (0.125 mol) in DCM (200 ml) was cooled to 0° C. and methylsulfonyl chloride (0.125 mol) was added dropwise keeping the temperature at 0-5° C., then the reaction mixture was stirred for 4 hours at room temperature and poured out into water (1000 ml). The organic layer was separated, dried ($MgSO_4$), filtered off and the solvent was evaporated, yielding 18 g (oil, 85%) of intermediate 65.

f) Preparation of Intermediate 66

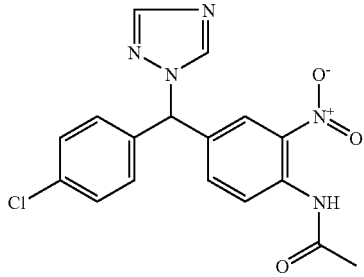

A mixture of intermediate 65 (0.0490 mol), 1H-1,2,4-triazole (0.265 mol) and potassium carbonate (0.267 mol) in acetonitrile (200 ml) was stirred and refluxed for 2 hours, then the solvent was evaporated dry and the residue was partitioned between water and DCM. The organic layer was separated, dried ($MgSO_4$), filtered off and the solvent was evaporated. The residue was purified by high-performance liquid chromatography over silica gel (eluent: DCM/MeOH 98/2). The pure fractions were collected and the solvent was evaporated, yielding 14 g (71%) of intermediate 66.

g) Preparation of Intermediate 67

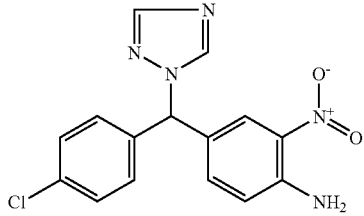

A mixture of intermediate 66 (0.0376 mol) in hydrochloric acid 3N (80 ml) was stirred at room temperature for 12 hours and water (200 ml) was added, then the reaction mixture was neutralised with potassium carbonate and extracted with DCM/MeOH. The organic extract was dried ($MgSO_4$) and the solvent was evaporated. The residue (12 g) was purified by column chromatography over silica gel (eluent: DCM/MeOH 98/2). The product fractions were collected and the solvent was evaporated, yielding 7.2 g (58%) of intermediate 67.

h) Preparation of Intermediate 68

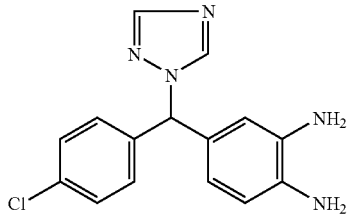

A mixture of intermediate 67 (0.0218 mol) in MeOH (100 ml) was hydrogenated for 1 hour with Raney Nickel (7 g) as a catalyst. After uptake of $H_2$ (3 equiv.), the $H_2$ was flushed

Example A21

Preparation of Intermediate 69

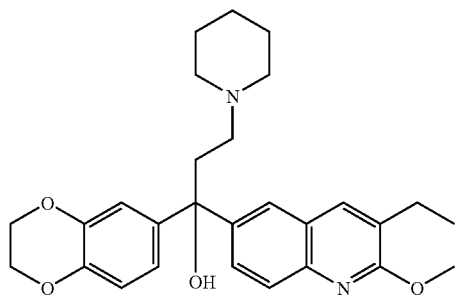

nBuLi 1.6M (0.02986 mol) was added at −78° C. under N₂ flow to a solution of 6-bromo-3-ethyl-2-methoxy-quinoline (0.02488 mol) in THF (120 ml). The mixture was stirred at −30° C. for 1 hour and cooled again to −70° C. A mixture of 1-(2,3-dihydro-1,4-benzodioxin-6-yl)-3-(1-piperidinyl)-1-propanone (0.02488 mol) in THF (60 ml) was added slowly. The mixture was stirred at −70° C. for 1 hour, poured out into water and ammonium chloride and extracted with EtOAc. The organic layer was separated, dried (MgSO₄), filtered and the solvent was evaporated till dryness. The residue (14.92 g) was purified by column chromatography over silica gel (15-35 μm) (eluent: DCM/MeOH/NH₄OH 94/6/0.1). The desired fractions were collected and the solvent was evaporated, yielding: 7.2 g (63%) of intermediate 69.

Example A22

Preparation of Intermediate 70

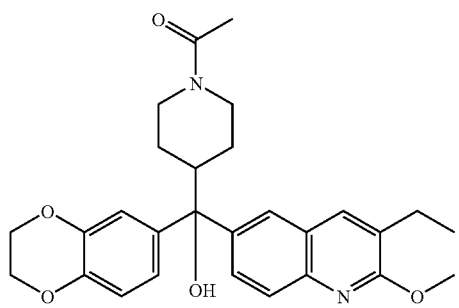

nBuLi 1.6M in hexane (0.09 mol) was added slowly at −78° C. under N₂ flow to a solution of 6-bromo-3-ethyl-2-methoxy-quinoline (0.075 mol) in THF (200 ml). The mixture was stirred for 1 hour. A mixture of 1-acetyl-4-[(2,3-dihydro-1,4-benzodioxin-6-yl)carbonyl]-piperidine (0.075 mol) in THF (100 ml) was added dropwise at −78° C. The mixture was stirred at −30° C. for 2 hours, poured out into water and ammonium chloride and extracted with EtOAc. The organic layer was separated, dried (MgSO₄), filtered and the solvent was evaporated till dryness. The residue (37.1 g) was purified by column chromatography over silica gel (15-35 μm) (eluent: DCM/MeOH/NH₄OH 97/3/0.15). The desired fractions were collected and the solvent was evaporated. The residue was crystallized from DIPE. The precipitate was filtered off and dried, yielding 0.8 g of intermediate 70, melting point 114° C.

B. Preparation of the Final Compounds

Example B1

Preparation of Compound 1

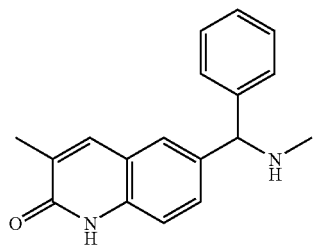

A mixture of intermediate 5 (0.013 mol) in hydrochloric acid 6N (40 ml) and 2-propanol (40 ml) was stirred and heated at 80° C. for 6 h. The mixture was cooled to room temperature, poured into ice water, basified with NH₄OH and extracted with DCM. The organic layer was dried (MgSO₄), filtered off and evaporated. The residue was purified by column chromatography over silica gel (15-40 μm) (eluent: DCM/MeOH/NH₄OH 97/3/0.1). The pure fractions were collected and evaporated. The residue (3.9 g) was crystallized from EtOAc, yielding 2.47 g (27%) of compound 1, melting point 174.3° C.

Example B2

Preparation of Compound 2

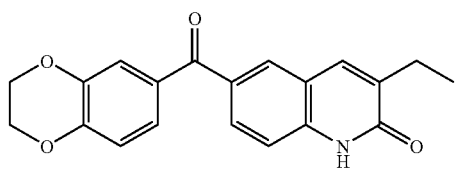

Sulfuric acid (1 ml) was added at 0° C. to a solution of chromium(VI)oxide (0.01186 mol) in water (2.2 ml). The mixture was then added at 0° C. to a suspension of intermediate 7 (0.00593 mol) in 2-propanone (40 ml). The mixture was stirred at room temperature for 3 hours, poured out into an aqueous potassium carbonate 10% solution and extracted with DCM. The precipitate was filtered off and washed with a boiling mixture of DCM and MeOH (50/50). The combined organic layer was dried (MgSO₄), filtered and the solvent was evaporated till dryness. The residue was crystallized from MeOH. The precipitate was filtered off and dried, yielding 0.69 g of compound 2, melting point 255° C.

Example B3

Preparation of Compound 3

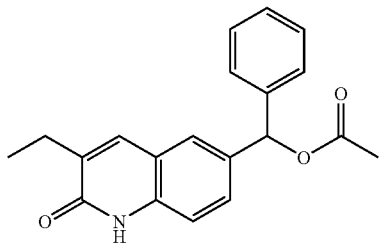

A mixture of intermediate 10 (0.01432 mol) in acetic acid, anhydride (50 ml) was stirred at 100° C. for 3 h. The mixture was poured into ice, basified with ammonium hydroxide and extracted with EtOAc. The organic layer was washed with water, dried (MgSO$_4$), filtered off and evaporated till dryness. The residue was purified by column chromatography over silica gel (15-40 µm) (eluent: DCM/MeOH/NH$_4$OH 97/3/0.1). The pure fractions were collected and the solvent was evaporated. The residue was crystallized from diethyl ether, yielding 1.65 g (36%) of compound 3, melting point 168.2° C.

Example B4

Preparation of Compound 4

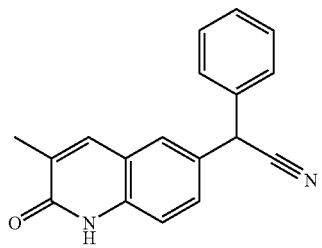

A mixture of intermediate 12 (0.022 mol) and tosyl chloride (0.033 mol) in potassium carbonate 10% (100 ml) and DCM (100 ml) was stirred at room temperature for 1 h. The mixture was extracted with DCM. The organic layer was dried (MgSO$_4$), filtered off and evaporated. The residue was recrystallized from diethyl ether, yielding 5 g (84%) of compound 4, melting point 227.5° C.

Example B5

Preparation of Compound 5

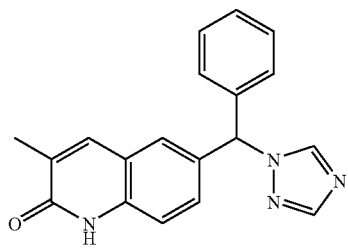

A solution of intermediate 15 (0.044 mol) in acetic acid, anhydride (100 ml) was stirred and refluxed for 12 h. The mixture was evaporated till dryness. The residue was taken up in water, basified with ammonium hydroxide and extracted in DCM. The organic layer was dried (MgSO$_4$), filtered off and evaporated till dryness. The residue (13.49 g) was purified by column chromatography over silica gel (eluent: DCM/MeOH/NH$_4$OH 97/3/0.1). The pure fractions were collected and evaporated. The residue (3 g, 22%) was added to a solution of activated carbon and MeOH. The mixture was stirred, filtered through celite and evaporated till dryness. The residue was crystallized from MEK, yielding 1.77 g (13%) of compound 5, melting point 254.2° C.

Example B6

Preparation of Compound 6

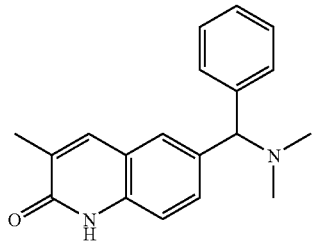

Formaldehyde (0.189 mol) and sodium cyanotrihydroborate (0.028 mol) were added to a mixture of intermediate 17 (0.00945 mol) in acetonitrile (50 ml). Acetic acid (0.019 mol) was added carefully over a 10 min. period and the mixture was stirred at room temperature for 3 h. The mixture was extracted with diethyl ether and washed with sodium hydroxide 3N. The organic layer was dried (MgSO$_4$), filtered off and evaporated. The residue was recrystallized from 2-propanone, yielding 1.6 g (76%) of compound 6, melting point 226.7° C.

Example B7

Preparation of Compound 7

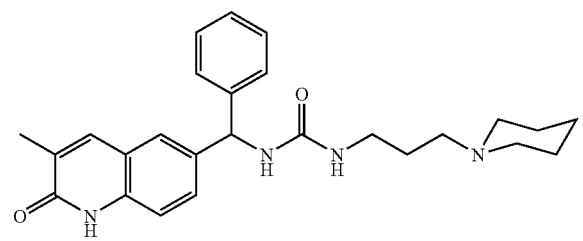

1-piperidinepropanamine (0.0794 mol) was added to a solution of intermediate 19 (0.0265 mol) in THF (200 ml). The mixture was stirred at room temperature for 4 hours. The solvent was evaporated till dryness. The residue was washed several times with water and taken up in DCM/MeOH 98/2. The organic solution was dried (MgSO$_4$), filtered and the solvent was evaporated. The residue (4 g) was purified by column chromatography over silica gel (35-70 µm) (eluent: DCM/MeOH/NH$_4$OH 90/10/1). The pure fractions were collected and the solvent was evaporated. The residue was washed with diethyl ether and dried. The residue (2.8 g) was taken up in potassium carbonate 10% and DCM and extracted with DCM. The organic layer was separated, dried (MgSO$_4$), filtered and the solvent was evaporated. The residue (2.2 g) was crystallized from diethyl ether. The precipitate was filtered off and dried, yielding 1.85 g (16%) of compound 7 as hydrate (1:1).

Example B8

Preparation of Compound 8

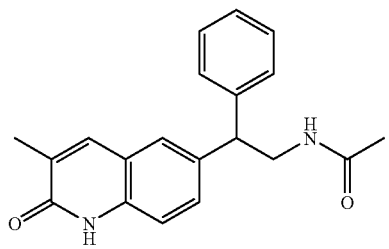

Acetyl chloride (0.012 mol) in DCM was added at 0° C. to a solution of intermediate 21 (0.01 mol) in DCM (52 ml) and pyridine (3 ml) and the mixture was stirred at room temperature for 2 h. Water was added and the product was extracted with DCM. The organic layer was washed with aqueous HCl 1N, then with aqueous potassium carbonate 10%, dried (MgSO$_4$), filtered off and evaporated. The residue (3.02 g) was recrystallized from EtOAc and diethyl ether, yielding 1.7 g (51%) of compound 8, melting point 206.2° C.

Example B9

Preparation of Compound 9

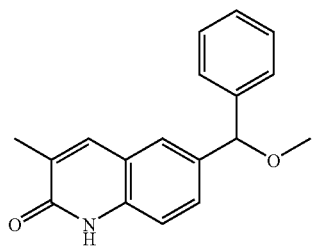

A solution of intermediate 23 (0.0088 mol) in MeOH (50 ml) was stirred and refluxed for 4 h. The mixture was cooled to room temperature and evaporated in vacuo. The residue was taken up in EtOAc/DCM/MeOH and stirred with activated carbon. The precipitate was filtered through celite and the filtrate was evaporated. The residue was recrystallized from DCM/MeOH, yielding 1.5 g (62%) of compound 9, melting point 207.3° C.

Example B10

Preparation of Compound 10

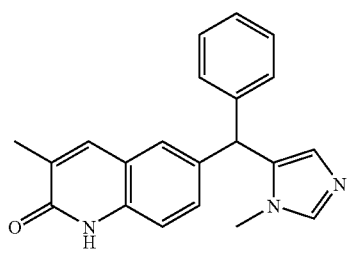

·H$_2$O (1:1)

Hydrochloric acid 12N (20 ml) and tin(II)chloride (0.0888 mol) were added to a mixture of intermediate 26 (0.0148 mol) in acetic acid (80 ml). The mixture was stirred at 120° C. for 24 hours, poured out into water, basified with ammonium hydroxide, filtered trough celite and rinced with DCM. The organic layer was separated, dried (MgSO$_4$), filtered and the solvent was evaporated. The residue (4.86 g) was crystallized from 2-propanone and diethyl ether. The precipitate was filtered off and dried. The residue (4.05 g, 83%,) was taken up in DCM. The mixture was washed with water and filtered trough celite. The organic layer was separated, dried (MgSO$_4$), filtered and the solvent was evaporated. The residue (3.46 g) was crystallized from 2-propanone and diethyl ether. The precipitate was filtered off and dried, yielding 2.71 g of compound 10 as hydrate (1:1), melting point 240° C.

Example B11

Preparation of Compound 11

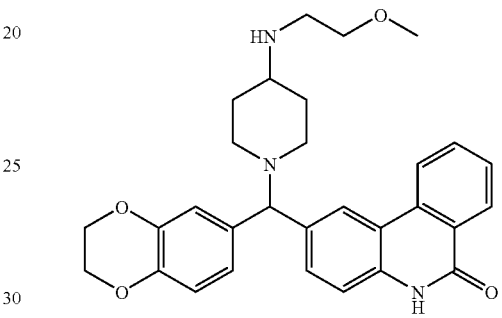

A mixture of intermediate 31 (0.0028 mol), intermediate 27 (0.0056 mol) and potassium carbonate (0.0084 mol) in acetonitrile (10 ml) was stirred at 80° C. for 2 hours. Water was added. The mixture was extracted with EtOAc. The organic layer was separated, dried (MgSO$_4$), filtered and the solvent was evaporated. The residue (1.1 g) was purified by column chromatography over silica gel (15-40 μm)(eluent: DCM/MeOH/NH$_4$OH 94/6/0.2). The pure fractions were collected and the solvent was evaporated. The residue (0.6 g, 43%) was crystallized from diethyl ether. The precipitate was filtered off and dried, yielding 0.201 g (14%) of compound 11, melting point 116° C.

Example B12

Preparation of Compound 12

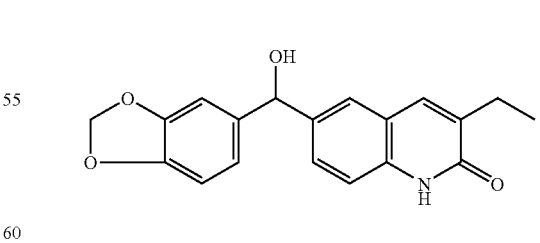

A mixture of intermediate 32 (0.0235 mol) in hydrochloric acid 3N (132 ml) and THF (80 ml) was stirred and refluxed for 4 hours, cooled to room temperature and poured out into ice water. The precipitate was filtered off, washed with water and with diethyl ether and dried. Part (1 g) of the residue (5.7 g) was crystallized from 2-propanone. The precipitate was fil-

Example B13

Preparation of Compound 13

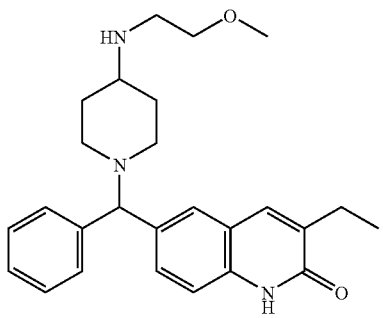

Sodium cyanotrihydroborate (0.0147 mol) was added portionwise to a solution of intermediate 34 (0.0147 mol) and 2-methoxy-ethanamine (0.0176 mol) in MeOH (80 ml), while stirring at 0° C. under $N_2$ flow. The mixture was allowed to warm to room temperature over a 30-min period, then poured out into water and extracted twice with DCM (2×100 ml). The combined organic layer was dried (MgSO$_4$), filtered and the solvent was evaporated. The residue (5 g) was purified by column chromatography over silica gel (15-40 µm) (eluent: DCM/MeOH/NH$_4$OH 95/5/0.3). The pure fractions were collected and the solvent was evaporated. The residue was allowed to crystallize out. The precipitate was filtered off and dried. The residue was recrystallized from diethyl ether and petroleum ether. The precipitate was filtered off and dried, yielding 2.1 g (34%) of compound 13.

Example B14

Preparation of Compound 14 and 15 compound 14

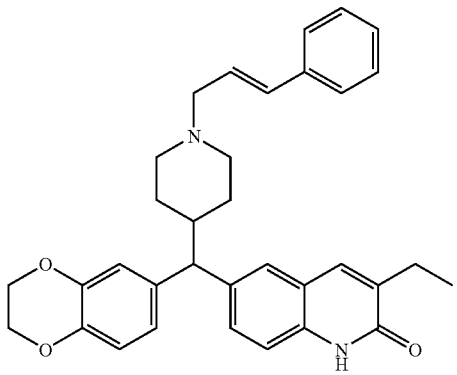

and compound 15

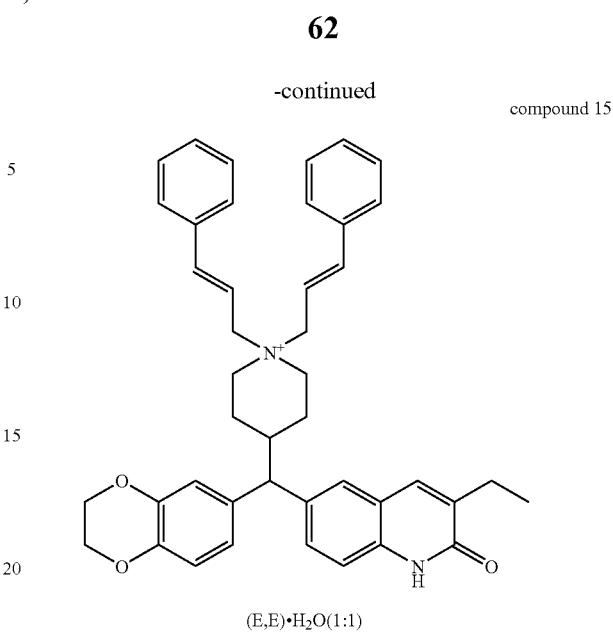

(E,E)·H$_2$O(1:1)

A mixture of intermediate 38 (0.001409 mol), (3-chloro-1-propenyl)-benzene (0.00183 mol) and potassium carbonate (0.00507 mol) in DMF (10 ml) was stirred at 70° C. for 15 hours, cooled to room temperature, poured out into water and extracted with EtOAc. The organic layer was separated, dried (MgSO$_4$), filtered and the solvent was evaporated till dryness. The residue (2.95 g) was purified by column chromatography over silica gel (15-35 µm) (eluent: DCM/MeOH/NH$_4$OH 95/5/0.1 and 80/20/0.5). Two fractions were collected and their solvents were evaporated, yielding 0.24 g F1 (33%) and 0.5 g F2 (53%). F1 was crystallized from 2-propanone and DIPE. The precipitate was filtered off and dried, yielding 0.16 g of compound 14, melting point 107° C. F2 was crystallized from 2-propanone and diethyl ether. The precipitate was filtered off and dried. The residue (0.38 g) was taken up in HCl (3N). The mixture was extracted with DCM. The organic layer was separated, dried (MgSO$_4$), filtered and the solvent was evaporated till dryness, yielding 0.25 g of compound 15, melting point 198° C.

Example B15

Preparation of Compound 16

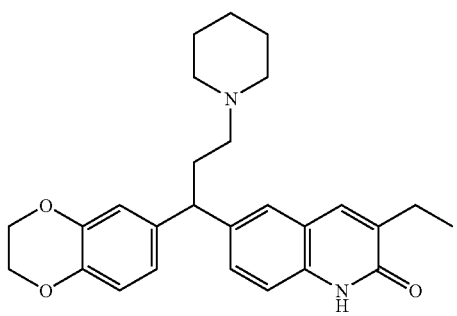

A mixture of intermediate 40 (0.00836 mol) in MeOH (60 ml) was hydrogenated under a 3 bar pressure for 15 hours with Pd/C 10% (0.36 g) as a catalyst. After uptake of H$_2$ (1 equiv), the catalyst was filtered through celite and the filtrate was evaporated till dryness. The residue (3.4 g) was purified by column chromatography over silica gel (15-40 μm) (eluent: DCM/MeOH/NH$_4$OH). The pure fractions were collected and their solvents were evaporated. The residue (1.8 g, 50%) was crystallized from MEK and DIPE. The precipitate was filtered off and dried, yielding compound 16, melting point 181° C.

Example B16

Preparation of Compound 17

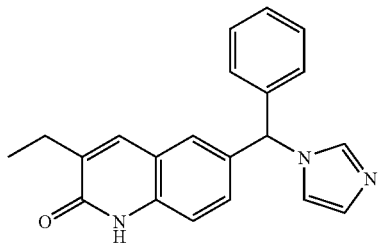

A mixture of intermediate 43 (0.088 mol) and chlorobenzene (1.162 mol) in aluminum chloride (300 ml) was stirred at 100° C. for 12 h. The mixture was poured into ice water, basified with ammonium hydroxide, filtered through celite and extracted with DCM. The organic layer was dried (MgSO$_4$), filtered off and evaporated till dryness. The residue (49.35 g) was purified by column chromatography over silica gel (eluent: DCM/MeOH/NH$_4$OH 97/3/0.2). The pure fractions were collected and evaporated. The residue (4.1 g, 14%) and norit in MeOH was stirred at 50° C. The mixture was filtered through celite and the filtrate was evaporated till dryness. The residue was crystallized from MEK/DIPE/MeOH, yielding 2.58 g (9%) of compound 17, melting point 220.1° C.

Example B17

Preparation of Compound 18

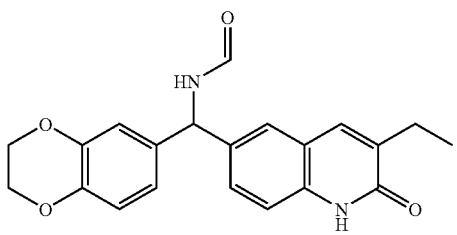

A mixture of compound 2 (0.0089 mol) in formic acid (11.3 ml) and formamide (3 ml) was stirred at 160° C. for 15 hours and then cooled to room temperature. Formic acid (11.3 ml) and formamide (3 ml) were added again. The mixture was stirred at 160° C. for 6 hours, cooled to room temperature, poured out into ice water and basified with a concentrated ammonium hydroxide solution. DCM was added. The precipitate was filtered off and taken up in water and MeOH. The mixture was stirred for 20 min. The precipitate was filtered off and dried, yielding 1.55 g (48%) of compound 18, melting point >260° C.

Example B18

Preparation of Compound 19

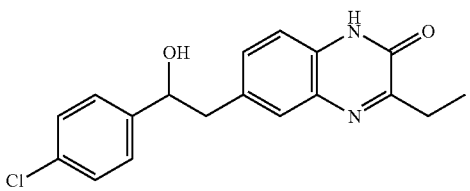

Sodium tetrahydroborate (0.0292 mol) was added slowly at 0° C. under N$_2$ flow to a suspension of [mixture (0.024 mol) of intermediate 49 (0.012 mol) and intermediate 50 (0.012 mol)] in MeOH (80 ml) and THF (80 ml). The mixture was stirred for 1 hour, then poured out into water and extracted with DCM. The organic layer was separated, dried (MgSO$_4$), filtered and the solvent was evaporated till dryness. The residue (7.5 g) was purified by column chromatography over silica gel (15-40 μm) (eluent: DCM/2-propanol/NH$_4$OH 96/4/0.1). The pure fractions were collected and the solvent was evaporated. The residue (5 g) was separated into its isomers by column chromatography over C 18 (column: HYPERSIL® C 18 10 μm) (eluent: MeOH/H$_2$O 68/32). The pure fractions were collected and the solvent was evaporated. The residue (2 g, 25%) was crystallized from MeOH. The precipitate was filtered off and dried, yielding 2 g of compound 19, melting point 204° C.

Example B19

Preparation of Compound 20

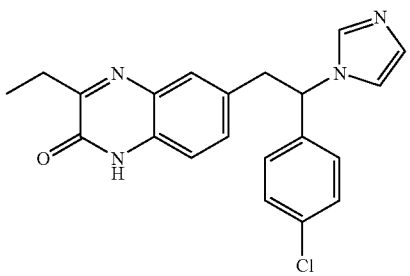

A solution of intermediate 55 (0.02 mol) in water (100 ml) was stirred at 0° C. and then a solution of propionylformic acid (0.029 mol) in acetic acid (30 ml) was added dropwise, then the resulting solution was stirred at room temperature for 2 hours and poured out into ice water. The mixture was neutralised to pH: 7 with sodium hydroxide (3N) and extracted with DCM. The organic layer was dried (MgSO$_4$) and the solvent was evaporated dry. The oily residue (11 g) was purified by high-performance liquid chromatography over silica gel (eluent: Toluene/2-propanol/NH$_4$OH 90/10/0.1). The product fractions were collected and the solvent was evaporated. The residue was crystallised from MeOH/DCM

Example B20

Preparation of Compound 21

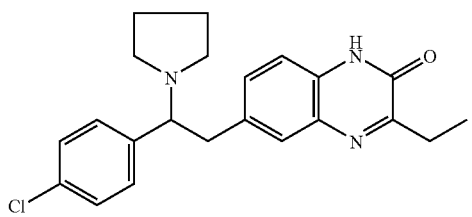

A mixture of intermediate 60 (0.0031 mol) and 2-oxo-butanoic acid, ethyl ester (0.00622 mol) in MeOH (50 ml) was stirred and refluxed for 12 hours. The solvent was evaporated. The residue (2 g) was purified by column chromatography over silica gel (15-40 μm) (eluent: DCM/MeOH/NH$_4$OH 95/5/0.5). The pure fractions were collected and the solvent was evaporated. The residue was crystallized from MEK and DIPE. The precipitate was filtered off and dried, yielding 0.215 g (18%) of compound 21, melting point 194° C.

Example B21

Preparation of Compound 22

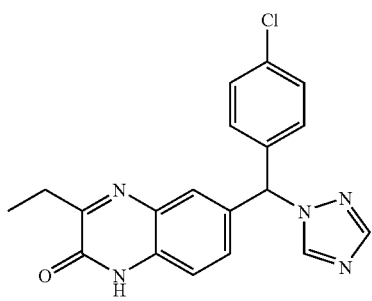

A mixture of propionylformic acid (0.0264 mol) in acetic acid (q.s.) was added dropwise at 0° C. to a solution of intermediate 68 (0.0250 mol) in acetic acid (q.s.) and water (80 ml), then the solution was stirred for 2 hours at 0° C. and poured out into ice-water. Sodium hydroxide (3N) was added until pH 7 and the resulting solution was extracted with DCM/MeOH. The organic layer was dried (MgSO$_4$) and the solvent was evaporated (vac.). The crude oily residue (12 g) was taken up with MeOH/DCM. The mother layers were evaporated dry and the residue was crystallised from EtOAc/MeOH, finally the desired product was collected, yielding 1.4 g (16%) of compound 22, melting point 188° C.

Example B22

Preparation of Compound 129 and 130

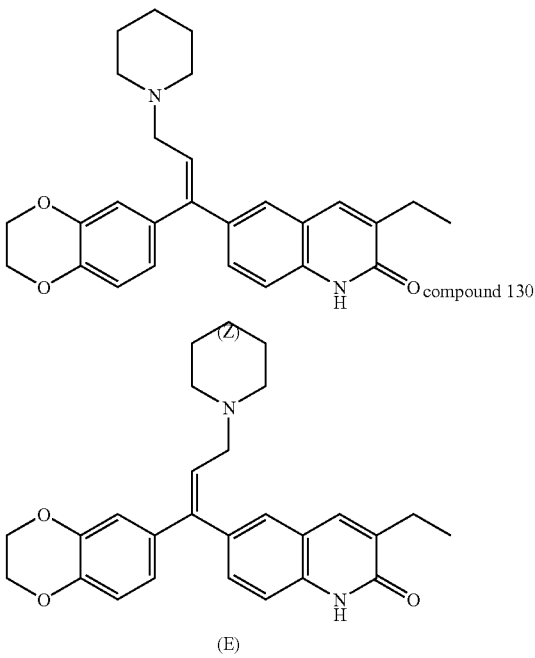

A mixture of intermediate 69 (0.0123 mol) in hydrochloric acid 6N (95 ml) and THF (38 ml) was stirred and refluxed for 15 hours, cooled to room temperature, poured out on ice, basified with a concentrated NH$_4$OH solution and extracted with DCM. The organic layer was separated, dried (MgSO$_4$), filtered and the solvent was evaporated till dryness. The residue (13.6 g) was purified by column chromatography over silica gel (15-35 μm) (eluent: DCM/MeOH/NH$_4$OH 94/6/0.5). Two desired fractions were collected and their solvents were evaporated. Both fractions were crystallized from 2-propanone. Each precipitate was filtered off and dried, yielding 0.7 g of compound 130, melting point 170° C. and 0.7 g of compound 129, melting point 252° C.

Example B23

Preparation of Compound 131

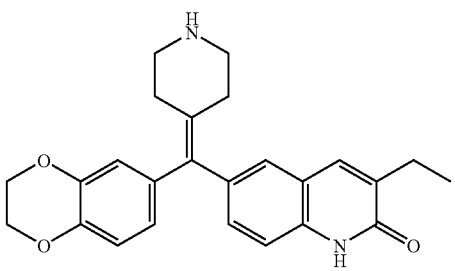

A mixture of intermediate 70 (0.0504 mol) in hydrochloric acid 3N (400 ml) and THF (200 ml) was stirred and refluxed for 12 hours, then poured out into ice water, basified with ammonium hydroxide and extracted with DCM. The organic layer was separated, dried (MgSO$_4$), filtered and the solvent was evaporated. The residue was purified by column chromatography over silica gel (eluent: DCM/MeOH/NH₄OH 90/10/0.1). The pure fractions were collected and the solvent was evaporated. The residue was crystallized from DIPE. The precipitate was filtered off and dried, yielding 7.45 g (37%) of compound 131, melting point 249° C.

Example B24

Preparation of Compound 132

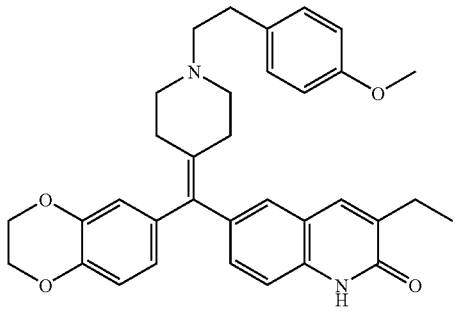

A mixture of compound 131 (0.00124 mol), 1-(2-bromo-ethyl)-4-methoxy-benzene (0.00186 mol) and potassium carbonate (0.00657 mol) in DMF (10 ml) was stirred at 70° C. for 15 hours, cooled to room temperature, poured out into water and extracted with EtOAc. The organic layer was separated, dried (MgSO₄), filtered and the solvent was evaporated till dryness. The residue (2.33 g) was purified by column chromatography over silica gel (15-40 µm) (eluent: DCM/MeOH/NH₄OH 97/3/0.1). The desired fractions were collected and the solvent was evaporated. The residue (0.37 g) was crystallized from 2-propanone and diethyl ether. The precipitate was filtered off and dried, yielding 0.24 g of compound 132, melting point 203° C.

Example B25

Preparation of Compound 133

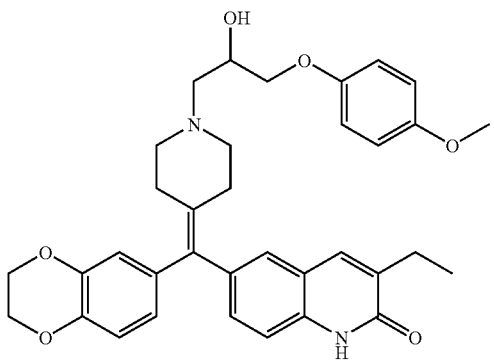

A solution of compound 131 (0.00248 mol) and [(4-methoxyphenoxy)methyl]-oxirane (0.00289 mol) in 2-propanol (15 ml) was stirred at 80° C. for 12 hours. A solid was filtered off and dried. The residue was purified by column chromatography over silica gel (35-70 µm) (eluent: DCM/MeOH/NH₄OH 95/5/0.1). The desired fractions were collected and the solvent was evaporated. The residue was crystallized from methyl ethyl keton and diethyl ether. The precipitate was filtered off and dried, yielding 0.72 g (50%) of compound 133, melting point 219° C.

Example B26

Preparation of Compounds 144 and 145

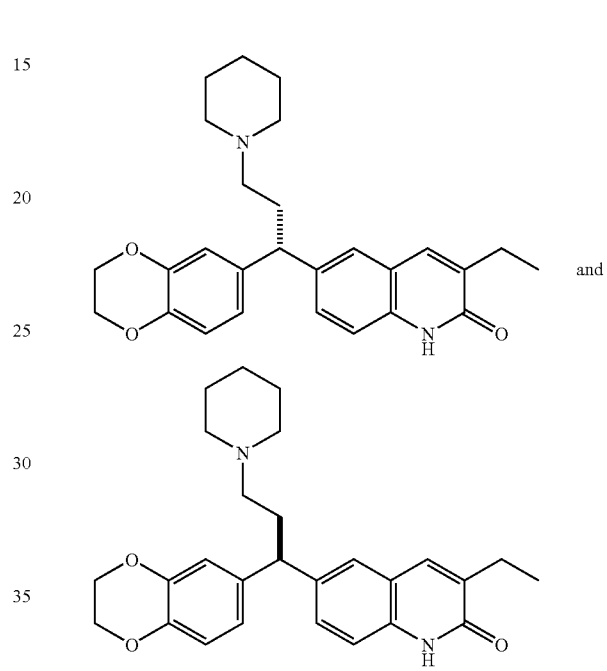

Enantiomer A   Enantiomer B   compound 144   compound 145

A mixture of intermediate 42 (0.0046 mol) and Pd/C (0.1 g) in THF (40 ml) was hydrogenated at room temperature for 18 hours under atmosphere pressure, then filtered over celite. The filtrate was evaporated. The residue (2.5 g) was purified by column chromatography over silica gel (eluent: DCM/MeOH/NH₄OH 95/5/0.5; 15-40 µm). Two fractions were collected and the solvent was evaporated, yielding 1.6 g F1 and 0.5 g F2. F1 was separated into two enantiomers by chiral chromatography (Chiralpak AD: eluent: MeOH 100; 20 µm). Two fractions were collected and the solvent was evaporated, yielding 0.56 g F3 and 0.38 g F4. F3 was crystallized from 2-propanone/DIPE. The precipitate was filtered off and dried, yielding 0.43 g (21%) of compound 144 (melting point 159° C.) (enantiomer A). F4 was crystallized from 2-propanone/DIPE. The precipitate was filtered off and dried, yielding 0.33 g (16%) of compound 145 (melting point 172° C.) (enantiomer B).

Table-1 lists the compounds that were prepared according to one of the above Examples. The following abbreviations were used in the tables: Co. No. stands for Compound Number, Ex. [Bn°] referred to the same method as described in the Bn° examples.

TABLE 1
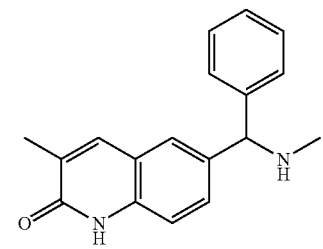
Co. No. 1; Ex. [B1]; mp. 174.3° C.
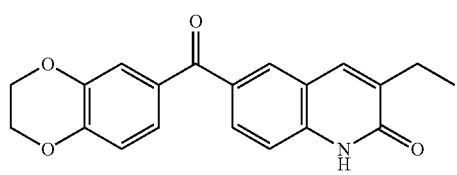
Co. No. 2; Ex. [B2]; mp. 255° C.
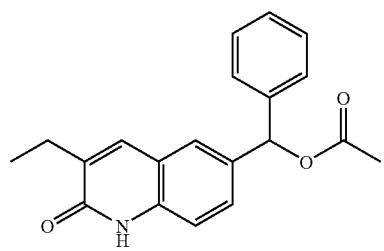
Co. No. 3; Ex. [B3]; mp. 168.2° C.
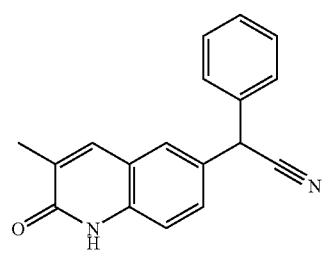
Co. No. 4; Ex. [B4]; mp. 227.5° C.
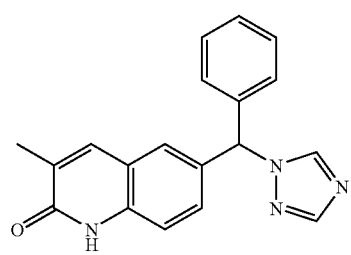
Co. No. 5; Ex. [B5]; mp. 254.2° C.
TABLE 1-continued
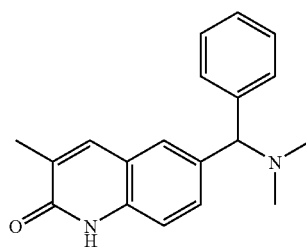
Co. No. 6; Ex. [B6]; mp. 226.7° C.
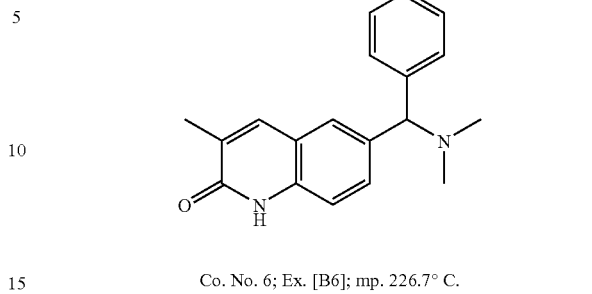
H₂O (1:1); Co. No. 7; Ex. [B7]
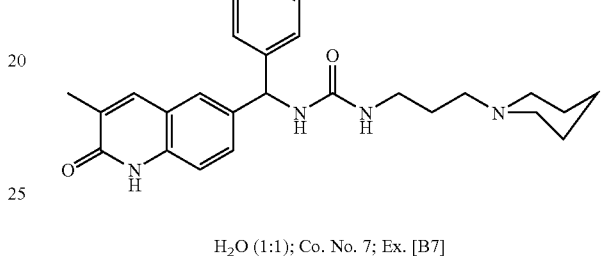
Co. No. 8; Ex. [B8]; mp. 206.2° C.
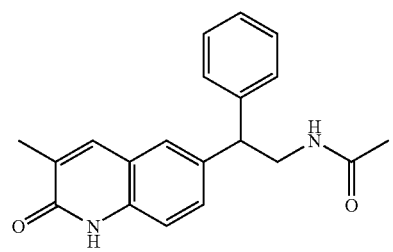
Co. No. 9; Ex. [B9]; mp. 207.3° C.
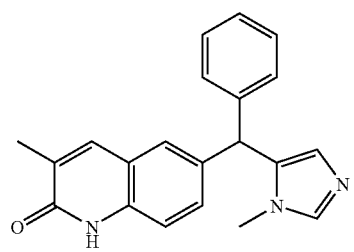
.H₂O (1:1); Co. No. 10; Ex. [B10]; mp. 240° C.

TABLE 1-continued
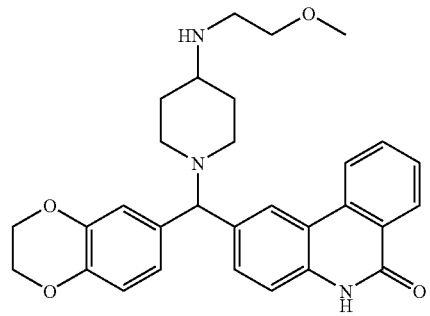
Co. No. 11; Ex. [B11]; mp. 116° C.
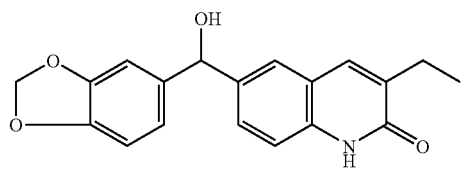
Co. No. 12; Ex. [B12]; mp. 211° C.
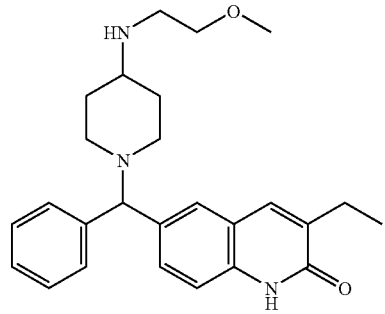
Co. No. 13; Ex. [B13]
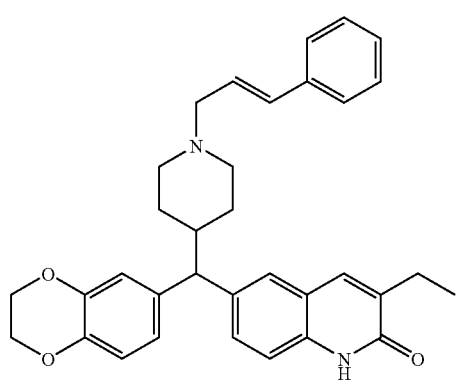
Co. No. 14; Ex. [B14]; mp. 107° C.
TABLE 1-continued
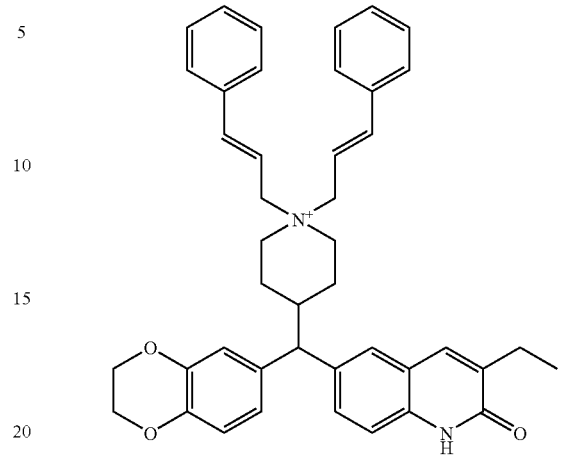
.H₂O (1:1).(E,E); Co. No. 15; Ex. [B14]; mp. 198° C.
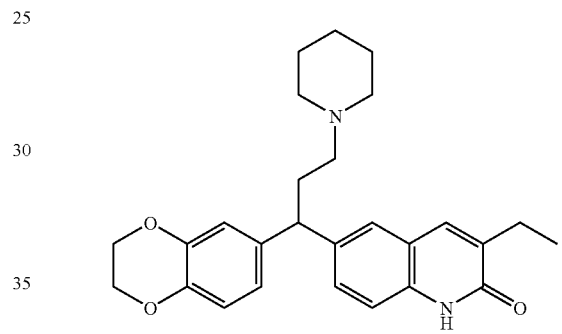
Co. No. 16; Ex. [B15]; mp. 181° C.
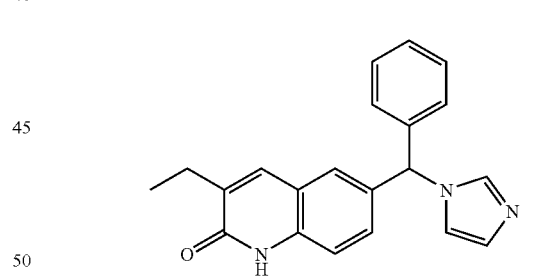
Co. No. 17; Ex. [B16]; mp. 220.1° C.
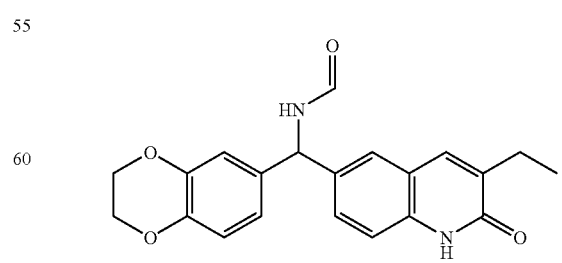
Co. No. 18; Ex. [B17]; mp. >260° C.

TABLE 1-continued
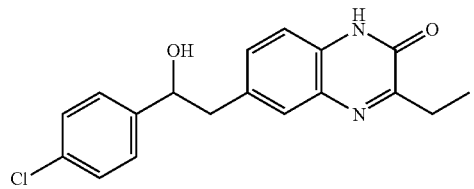
Co. No. 19; Ex. [B18]; mp. 204° C.
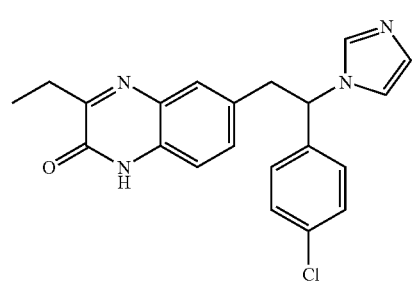
Co. No. 20; Ex. [B19]; mp. 270° C.
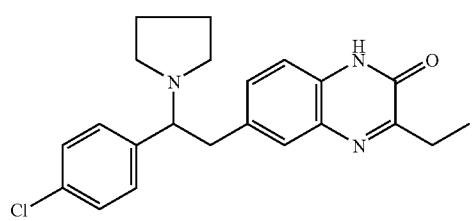
Co. No. 21; Ex. [B20]; mp. 194° C.
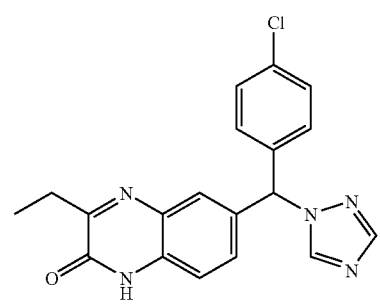
Co. No. 22; Ex. [B21]; mp. 188° C.
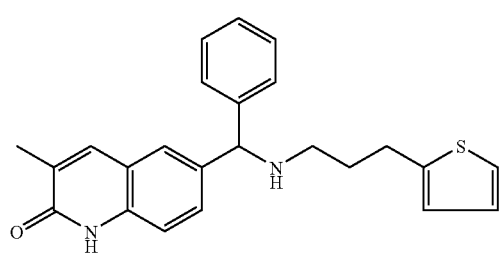
Co. No. 23; Ex. [B11]; mp. 140.7° C.
TABLE 1-continued
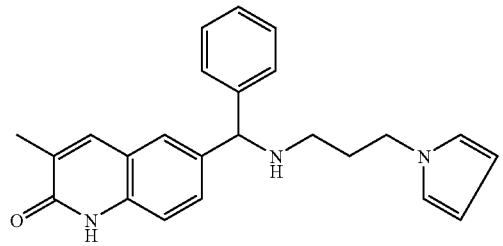
Co. No. 24; Ex. [B11]; mp. 135° C.
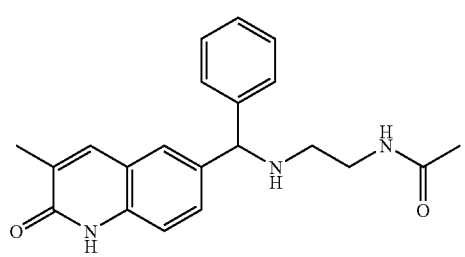
Co. No. 25; Ex. [B11]; mp. 177.3° C.
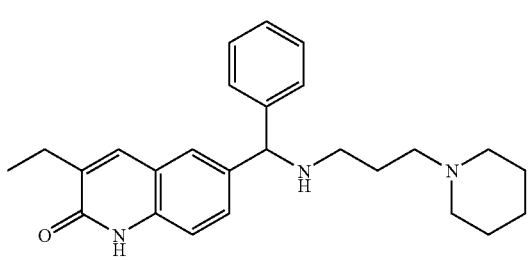
Co. No. 26; Ex. [B11]; mp. 131.2° C.
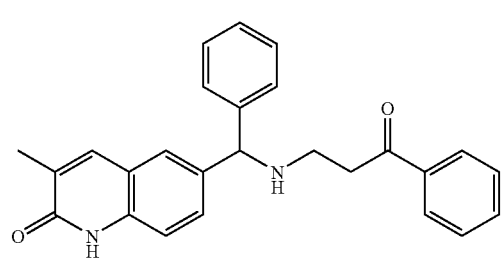
Co. No. 27; Ex. [B11]; mp. 183.2° C.
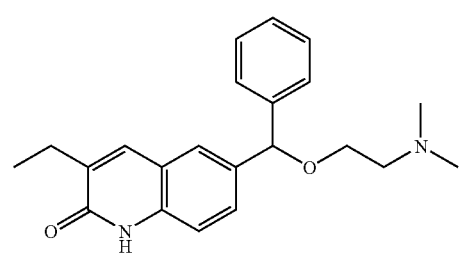
Co. No. 28; Ex. [B11]; mp. 117.1° C.

TABLE 1-continued
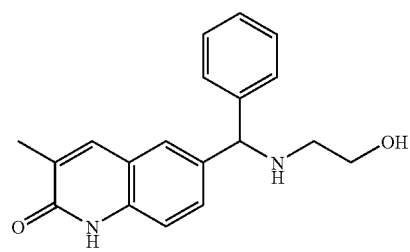
Co. No. 29; Ex. [B11]; mp. 170.6° C.
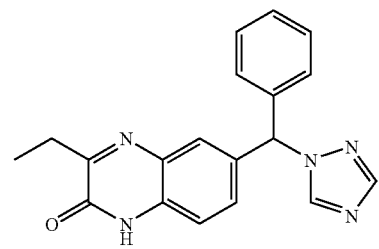
Co. No. 30; Ex. [B11]; mp. 192° C.
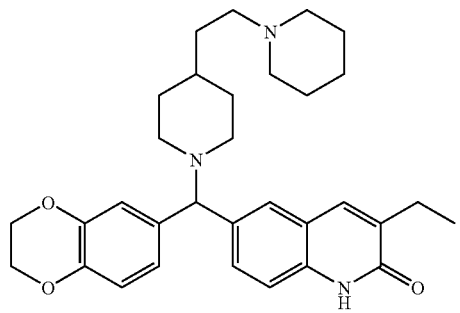
.C$_2$H$_2$O$_4$ (2:5); Co. No. 31; Ex. [B11]; mp. 140° C.
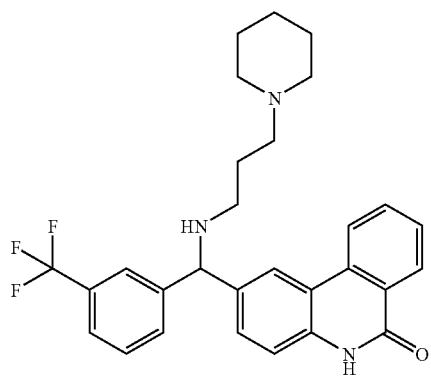
.C$_2$H$_2$O$_4$ (2:5).H$_2$O(1:1); Co. No. 32; Ex. [B11]; mp. 122° C.
TABLE 1-continued
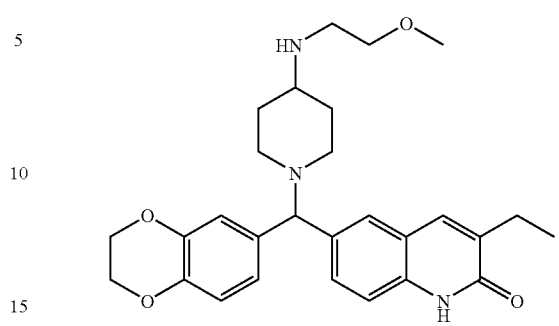
Co. No. 33; Ex. [B11]; mp. 108° C.
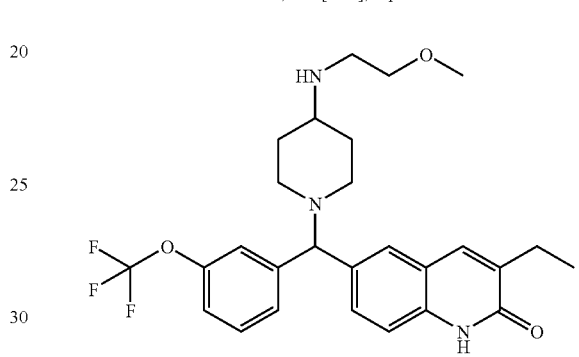
Co. No. 34; Ex. [B11]; mp. 142° C.
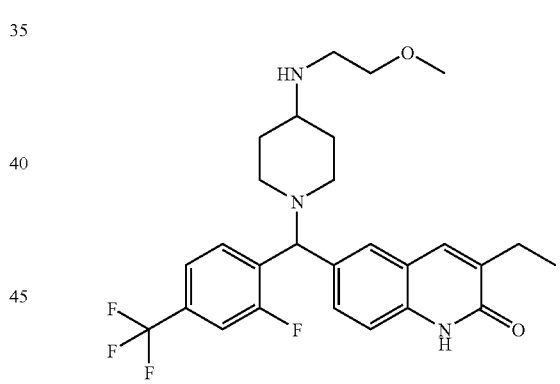
Co. No. 35; Ex. [B11]; mp. 110° C.
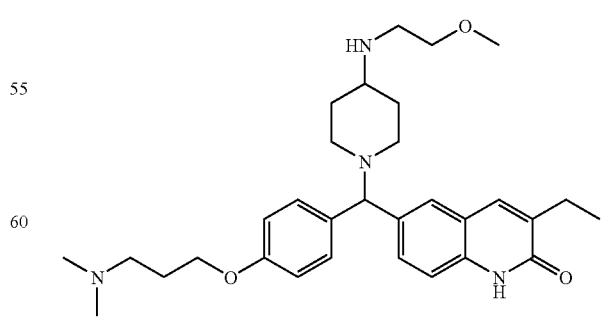
.H$_2$O (1:1); Co. No. 36; Ex. [B11]; mp. 88° C.

TABLE 1-continued
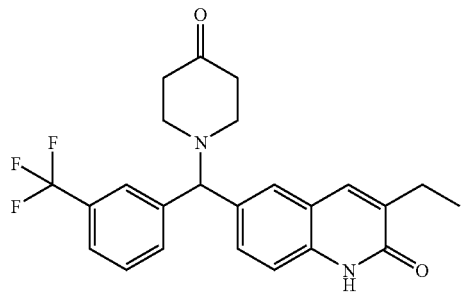
Co. No. 37; Ex. [B11]; mp. 182° C.
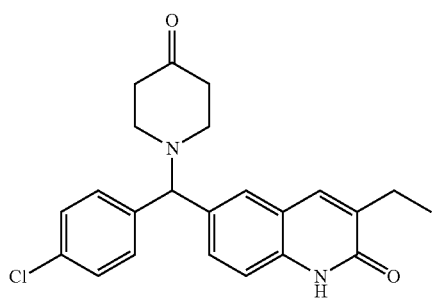
Co. No. 38; Ex. [B11]
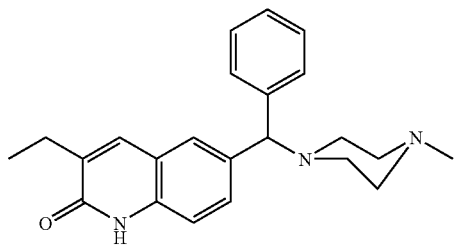
Co. No. 39; Ex. [B11]
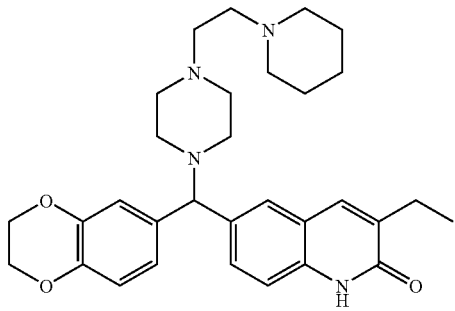
.C₂H₂O₄ (1:3); Co. No. 40; Ex. [B11]; mp. 130° C.
TABLE 1-continued
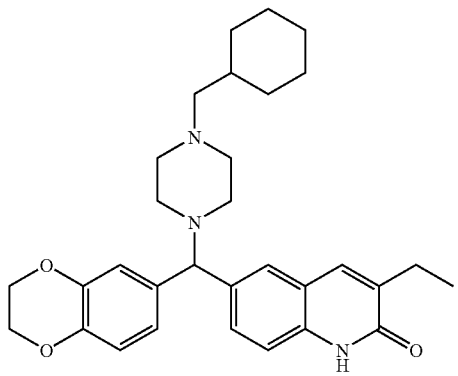
.C₂H₂O₄ (2:3); Co. No. 41; Ex. [B11]; mp. 125° C.
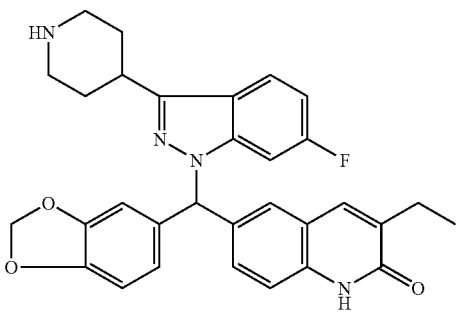
.H₂O (1:1); Co. No. 42; Ex. [B11]; mp. 158° C.
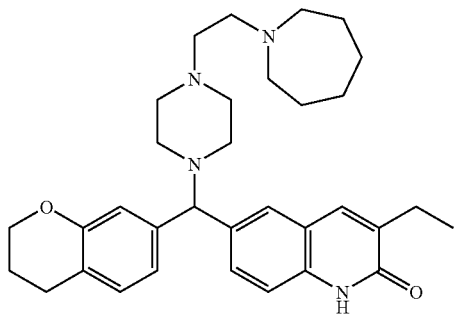
.C₂H₂O₄ (2:5).H₂O (1:1); Co. No. 43; Ex. [B11]; mp. 138° C.
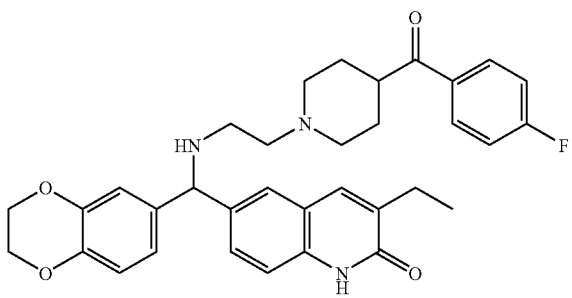
Co. No. 44; Ex. [B11]; mp. 104° C.

TABLE 1-continued
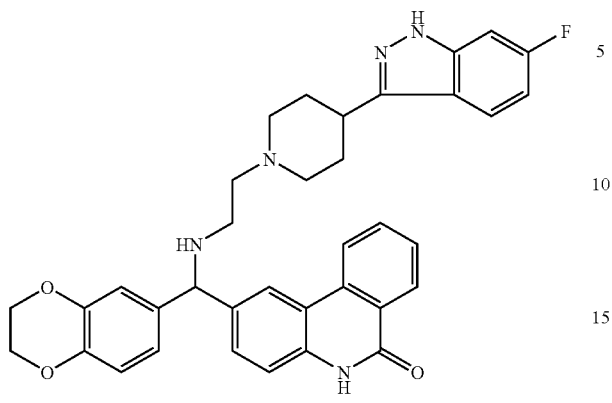
Co. No. 45; Ex. [B11]; mp. 240° C.
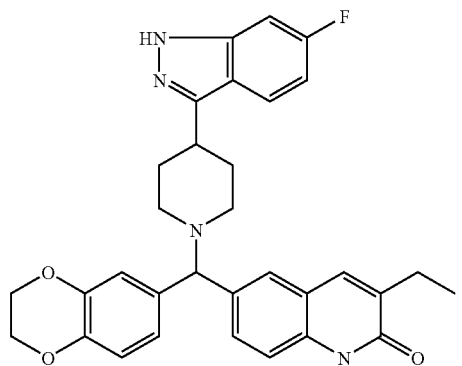
Co. No. 46; Ex. [B11]; mp. 180° C.
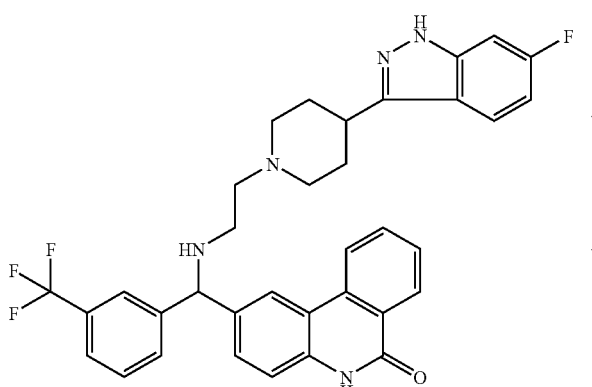
Co. No. 47; Ex. [B11]; mp. 200° C.
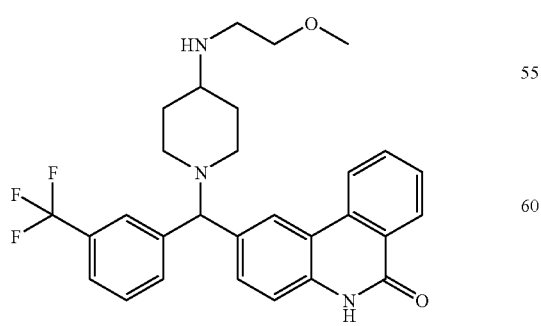
Co. No. 48; Ex. [B11]; mp. 188° C.
TABLE 1-continued
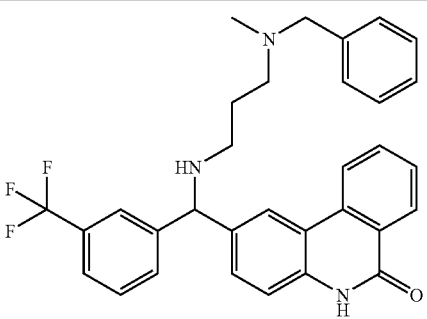
.$C_2H_2O_4$ (1:2); Co. No. 49; Ex. [B11]; mp. 120° C.
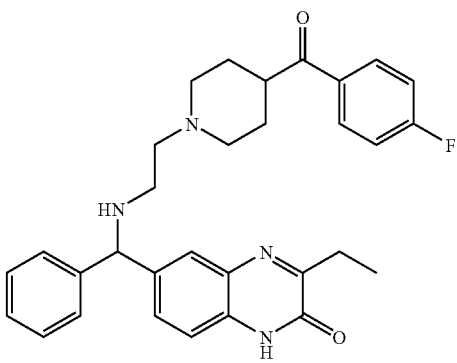
.$C_2H_2O_4$ (2:5).$H_2O$ (1:1); Co. No. 50; Ex. [B11]; mp. 130° C.
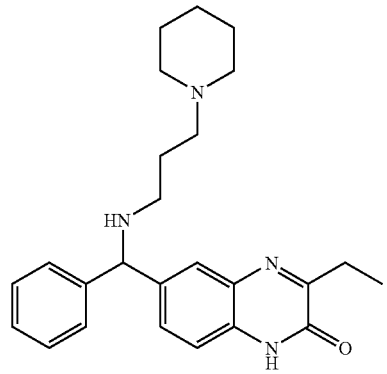
.$C_2H_2O_4$ (2:5).$H_2O$ (1:1); Co. No. 51; Ex. [B11]; mp. 114° C.
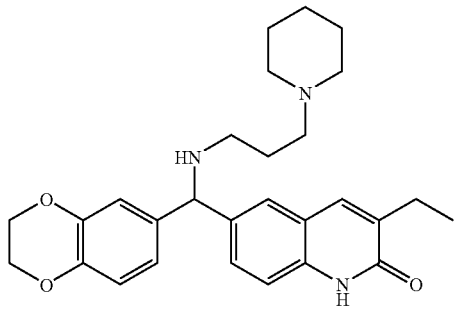
.$C_2H_2O_4$ (1:2).$H_2O$ (1:1); Co. No. 52; Ex. [B11]; mp. 130° C.

TABLE 1-continued
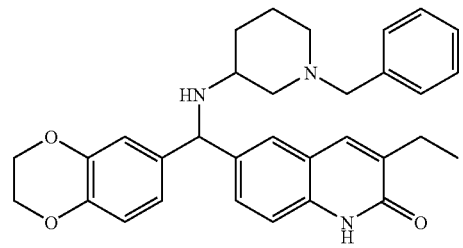
.C₂H₂O₄ (2:5).H₂O (1:1); Co. No. 53; Ex. [B11]; mp. 150° C.
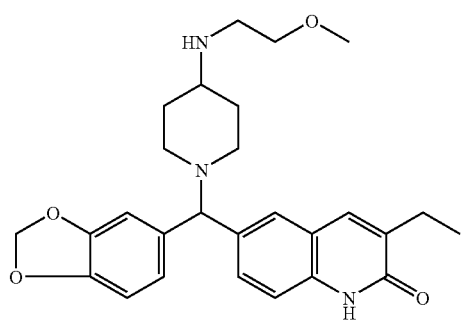
Co. No. 54; Ex. [B11]; mp. 157° C.
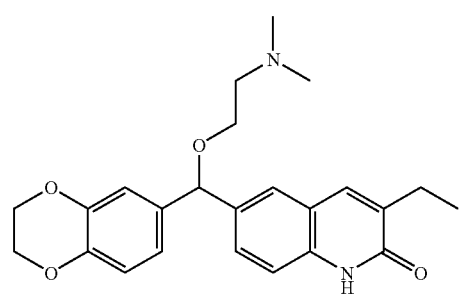
.C₂H₂O₄ (2:3); Co. No. 55; Ex. [B11]; mp. 134° C.
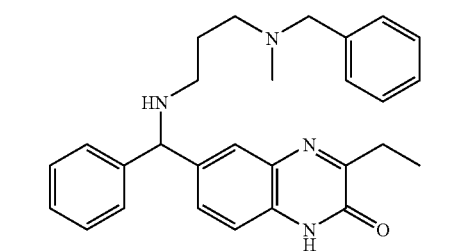
.C₂H₂O₄ (1:2).H₂O (1:1); Co. No. 56; Ex. [B11]; mp. 130° C.
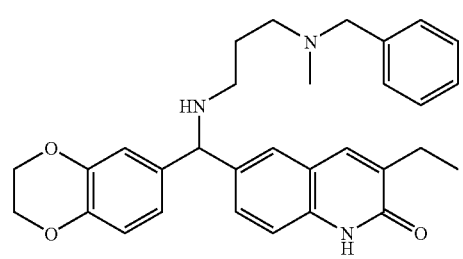
.C₂H₂O₄ (1:2).H₂O (1:1); Co. No. 57; Ex. [B11]; mp. 132° C.
TABLE 1-continued
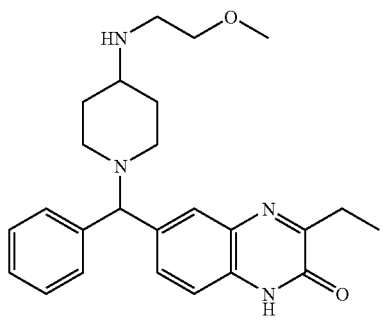
.C₂H₂O₄ (1:2).H₂O (1:1); Co. No. 58; Ex. [B11]; mp. 150° C.
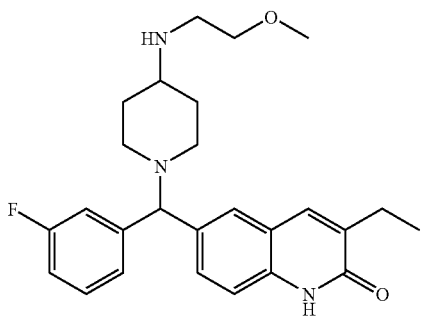
Co. No. 59; Ex. [B11]; mp. 172° C.
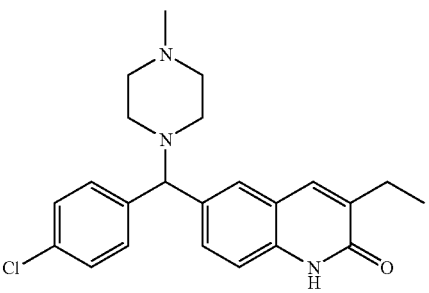
Co. No. 60; Ex. [B11]; mp. 122° C.
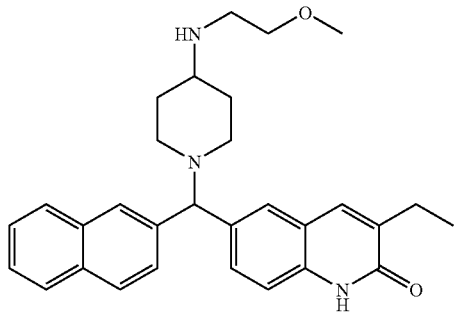
.H₂O (1:1); Co. No. 61; Ex. [B11]; mp. 122° C.

TABLE 1-continued
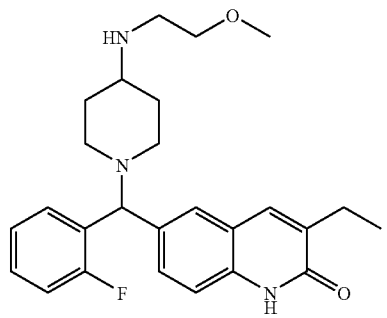
Co. No. 62; Ex. [B11]; mp. 156° C.
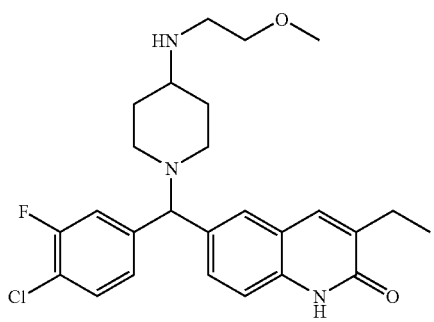
Co. No. 63; Ex. [B11]; mp. 148° C.
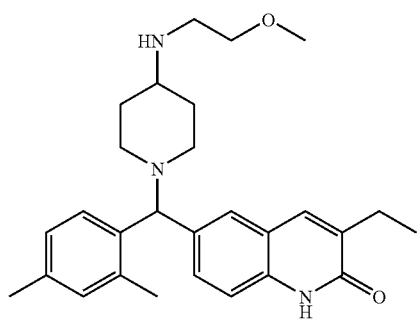
.H₂O (1:1); Co. No. 64; Ex. [B11]; mp. 100° C.
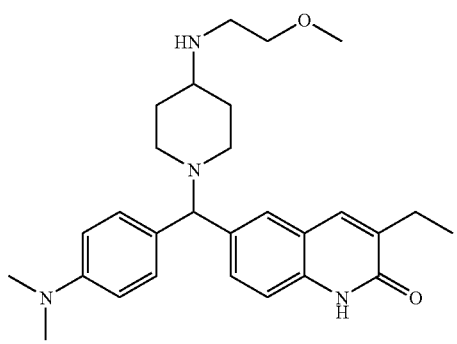
.H₂O (1:1); Co. No. 65; Ex. [B11]; mp. 110° C.
TABLE 1-continued
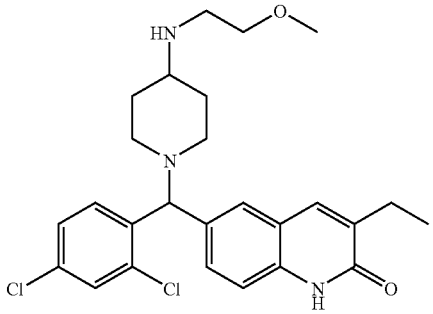
Co. No. 66; Ex. [B11]; mp. 110° C.
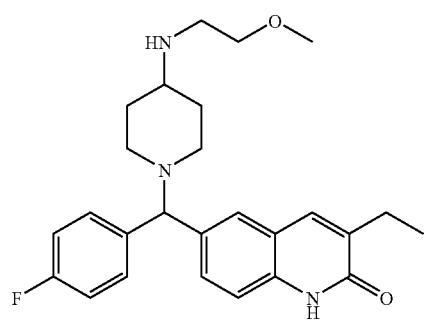
Co. No. 67; Ex. [B11]; mp. 138° C.
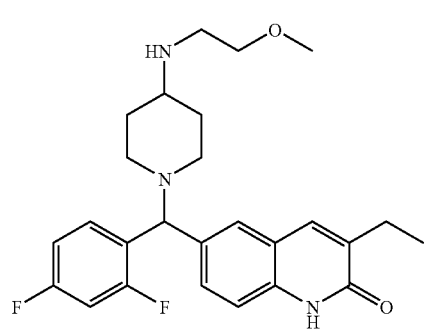
Co. No. 68; Ex. [B11]; mp. 96° C.
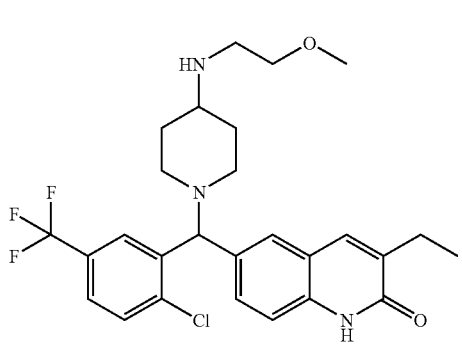
Co. No. 69; Ex. [B11]; mp. 108° C.

TABLE 1-continued
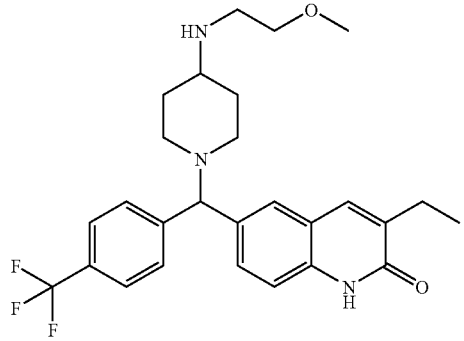
Co. No. 70; Ex. [B11]; mp. 112° C.
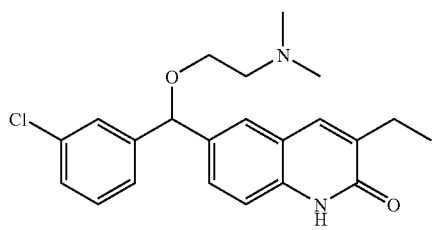
Co. No. 71; Ex. [B11]; mp. 144° C.
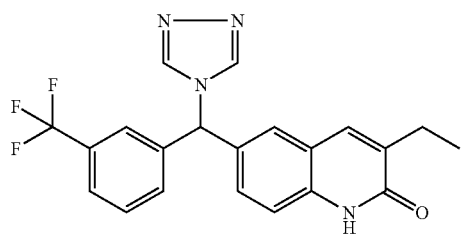
Co. No. 72; Ex. [B11]; mp. >260° C.
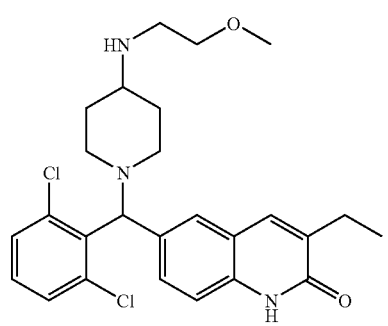
Co. No. 73; Ex. [B11]; mp. 114° C.
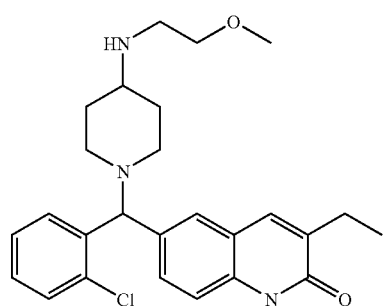
Co. No. 74; Ex. [B11]; mp. 102° C.
TABLE 1-continued
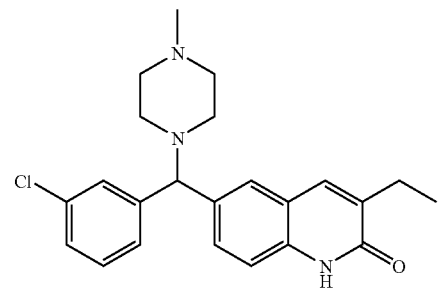
Co. No. 75; Ex. [B11]; mp. 126° C.
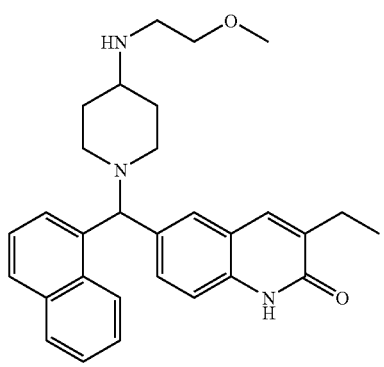
Co. No. 76; Ex. [B11]; mp. 118° C.
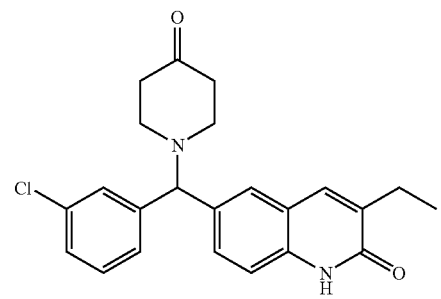
Co. No. 77; Ex. [B11]
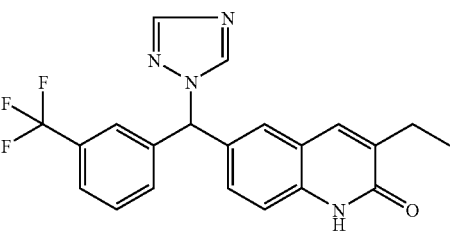
Co. No. 78; Ex. [B11]; mp. 165° C.
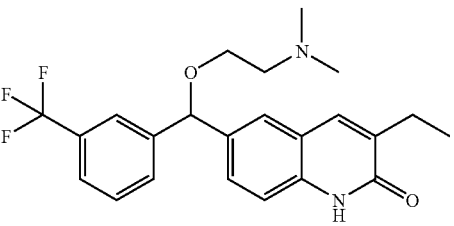
.$C_2H_2O_4$ (1:1); Co. No. 79; Ex. [B11]; mp. 105° C.

TABLE 1-continued
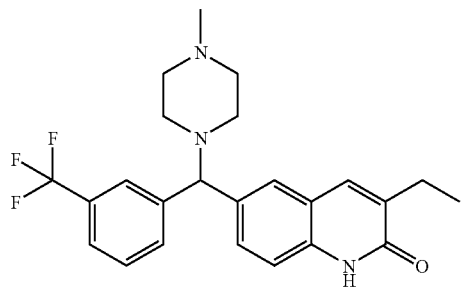
Co. No. 80; Ex. [B11]; mp. 157° C.
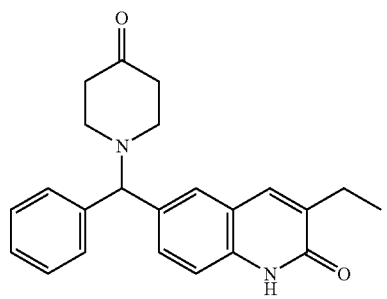
Co. No. 81; Ex. [B11]
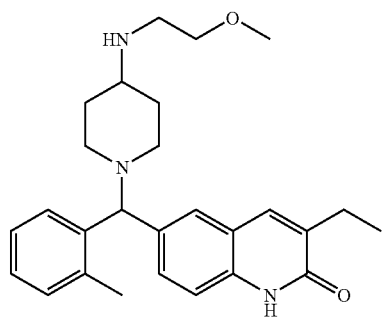
Co. No. 82; Ex. [B11]; mp. 144° C.
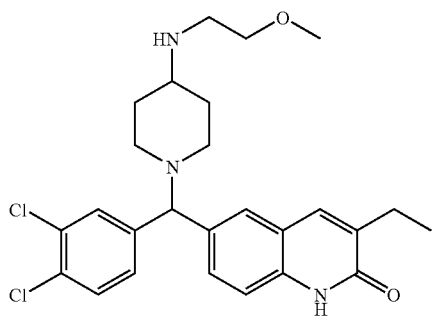
Co. No. 83; Ex. [B11]; mp. 172° C.
TABLE 1-continued
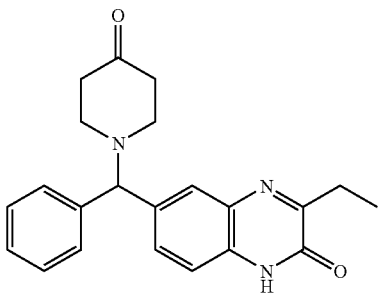
Co. No. 84; Ex. [B11]; mp. 189° C.
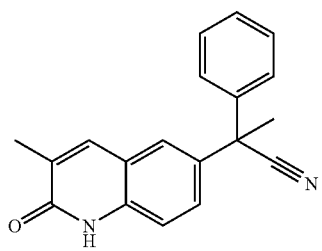
Co. No. 85; Ex. [B12]; mp. 178° C.
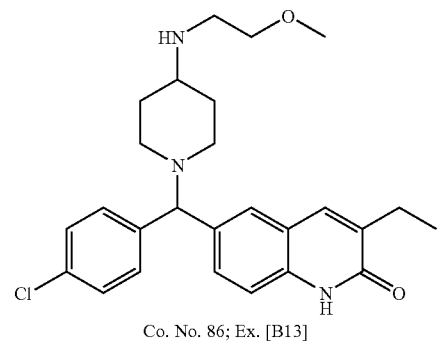
Co. No. 86; Ex. [B13]
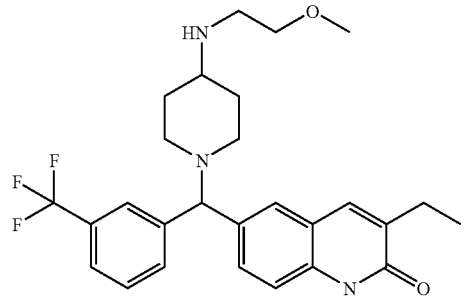
Co. No. 87; Ex. [B13]; mp. 174–178° C.
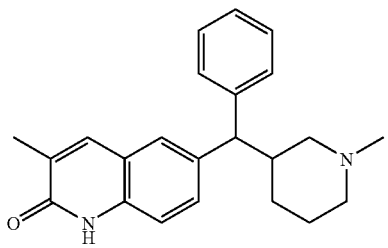
Co. No. 88; Ex. [B15]

TABLE 1-continued
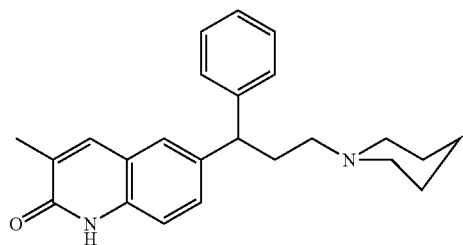
Co. No. 89; Ex. [B15]
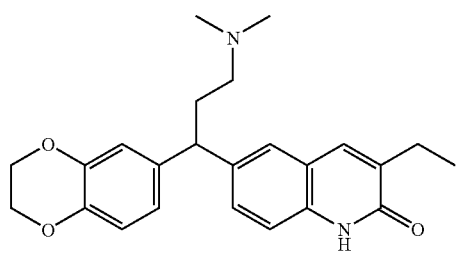
Co. No. 90; Ex. [B15]; mp. 150° C.
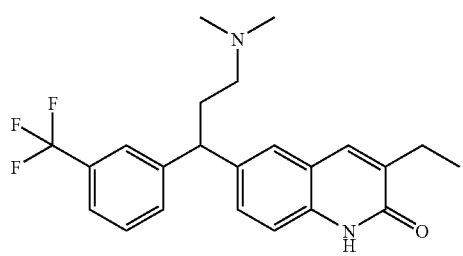
.C$_2$H$_2$O$_4$ (1:1); Co. No. 91; Ex. [B15]; mp. 197° C.
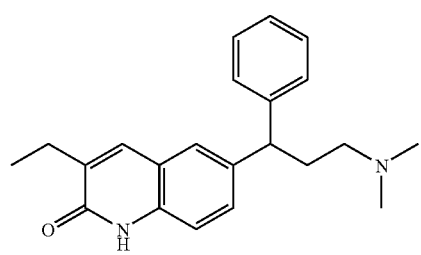
Co. No. 92; Ex. [B15]; mp. 136° C.
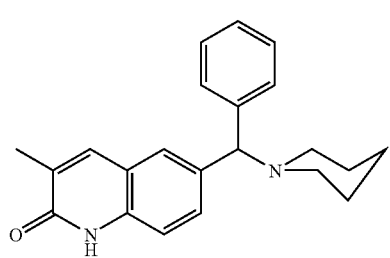
Co. No. 93; Ex. [B16]; mp. 206.5° C.
TABLE 1-continued
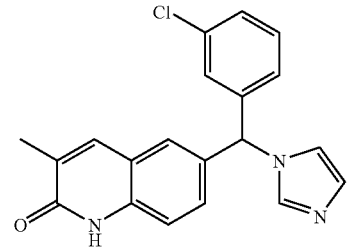
Co. No. 94; Ex. [B16]; mp. 221.9° C.
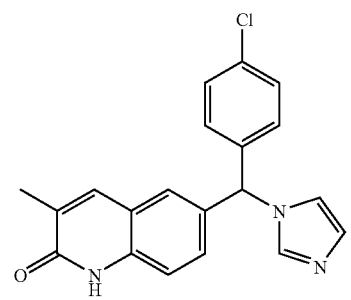
Co. No. 95; Ex. [B16]; mp. 215.1° C.
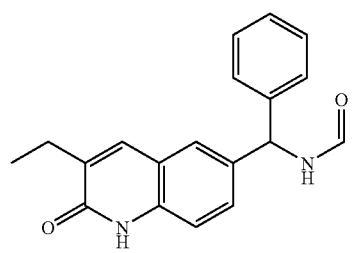
Co. No. 96; Ex. [B17]; mp. >260° C.
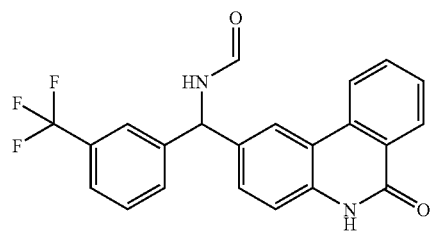
Co. No. 97 Ex. [B17]; mp. >260° C.
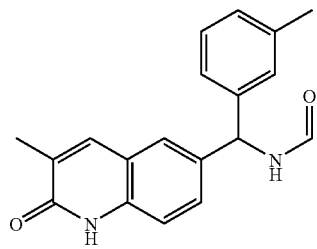
Co. No. 98; Ex. [B17]; mp. 258.6° C.

TABLE 1-continued
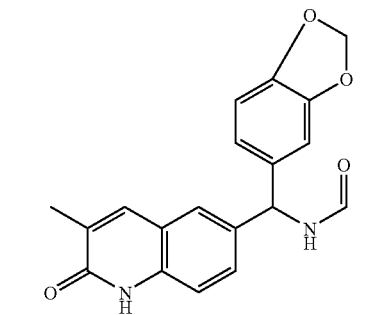
Co. No. 99; Ex. [B17]; mp. 267.5° C.
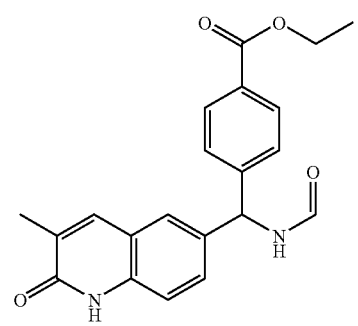
Co. No. 100; Ex. [B17]; mp. 221.6° C.
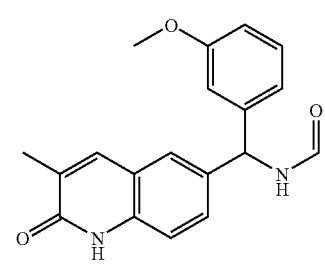
Co. No. 101; Ex. [B17]; 223.6° C.
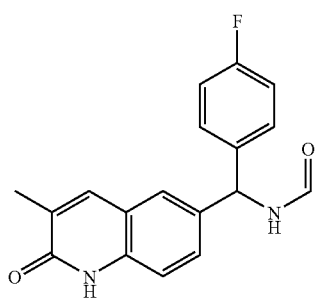
Co. No. 102; Ex. [B17]; mp. 257.9° C.
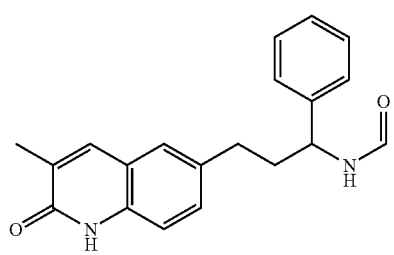
Co. No. 103; Ex. [B17]; mp. 217° C.
TABLE 1-continued
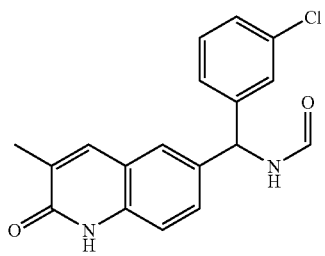
Co. No. 104; Ex. [B17]; mp. 258° C.
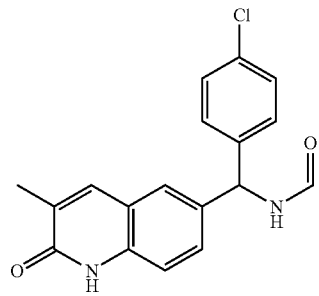
Co. No. 105; Ex. [B17]; mp. 259.7° C.
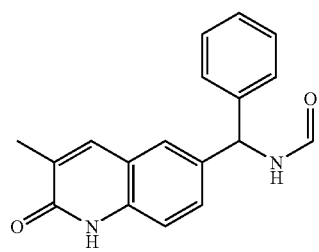
Co. No. 106; Ex. [B17]; mp. 268.7° C.
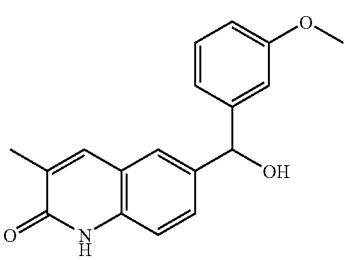
Co. No. 107; Ex. [B18]; mp. 226.8° C.
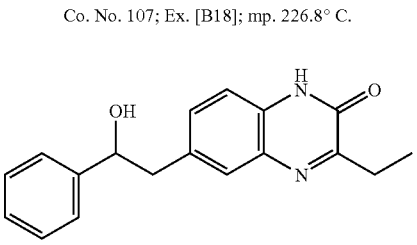
Co. No. 108; Ex. [B18]; mp. 194° C.

TABLE 1-continued
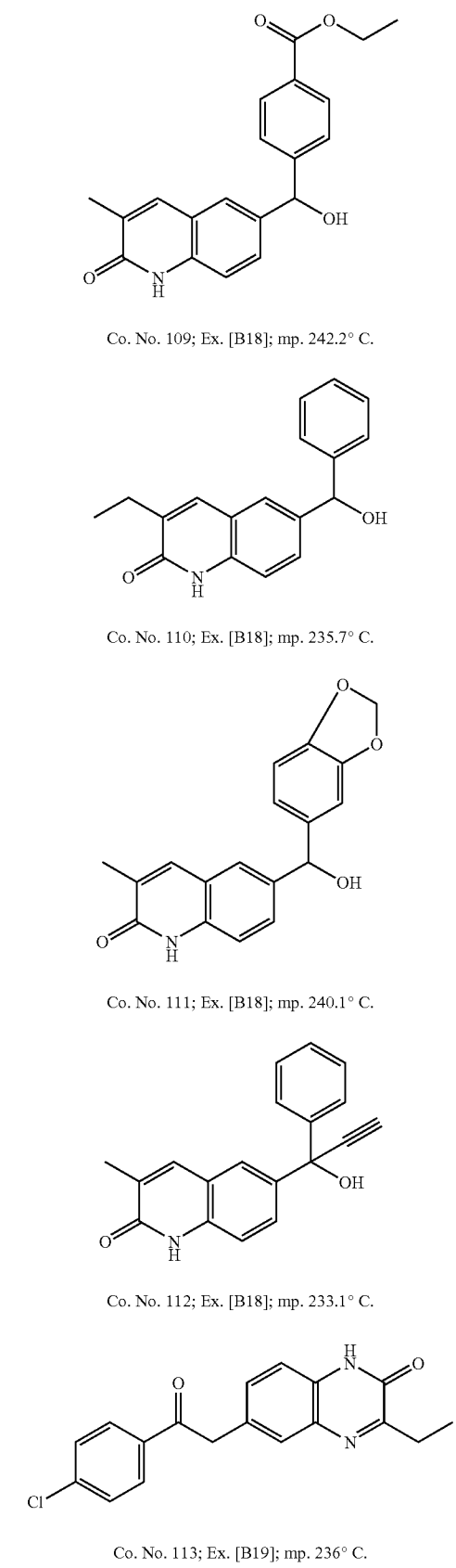
Co. No. 109; Ex. [B18]; mp. 242.2° C.
Co. No. 110; Ex. [B18]; mp. 235.7° C.
Co. No. 111; Ex. [B18]; mp. 240.1° C.
Co. No. 112; Ex. [B18]; mp. 233.1° C.
Co. No. 113; Ex. [B19]; mp. 236° C.
TABLE 1-continued
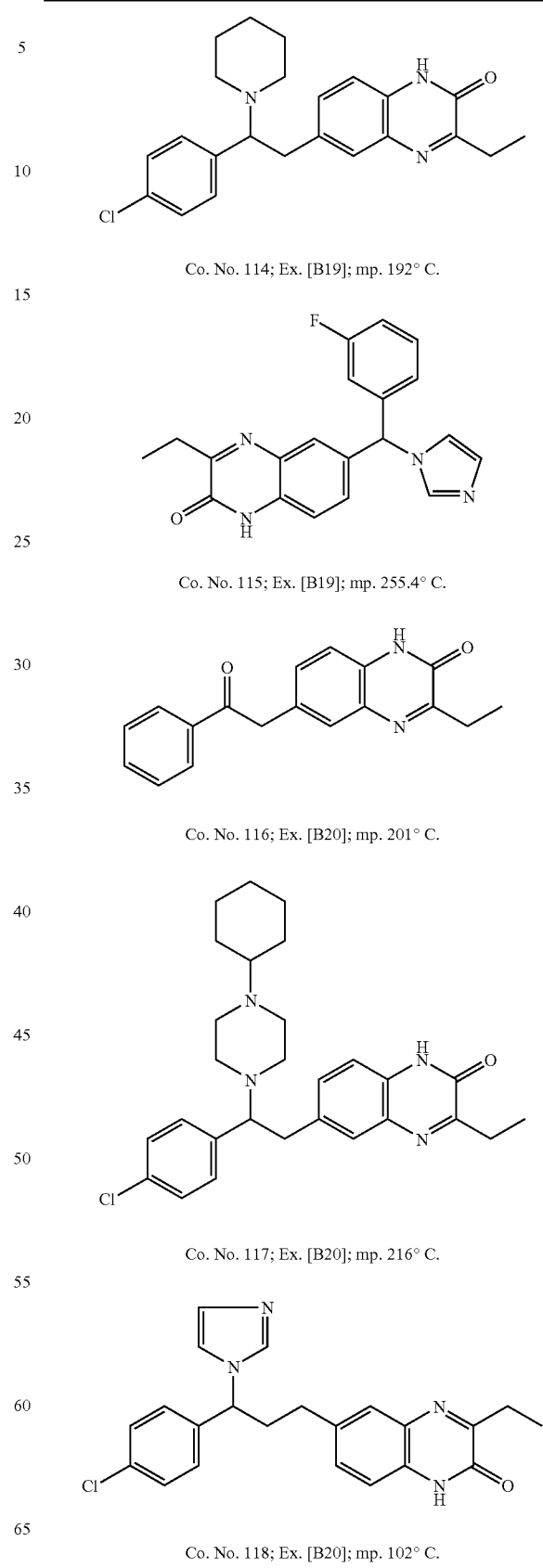
Co. No. 114; Ex. [B19]; mp. 192° C.
Co. No. 115; Ex. [B19]; mp. 255.4° C.
Co. No. 116; Ex. [B20]; mp. 201° C.
Co. No. 117; Ex. [B20]; mp. 216° C.
Co. No. 118; Ex. [B20]; mp. 102° C.

TABLE 1-continued
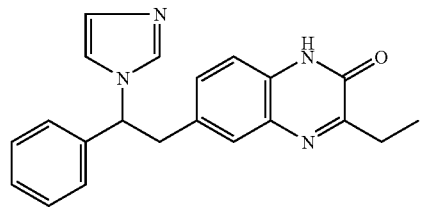
Co. No. 119; Ex. [B20]; mp. 224° C.
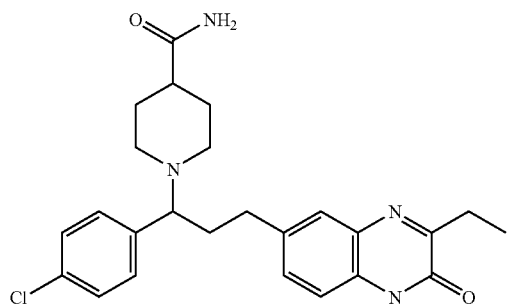
Co. No. 120; Ex. [B20]
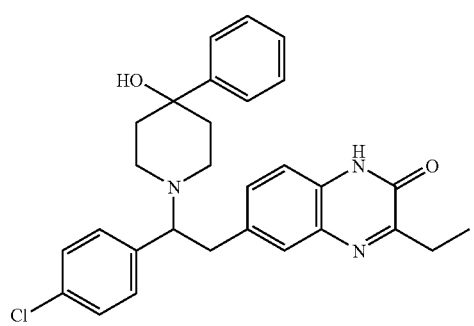
Co. No. 121; Ex. [B20]
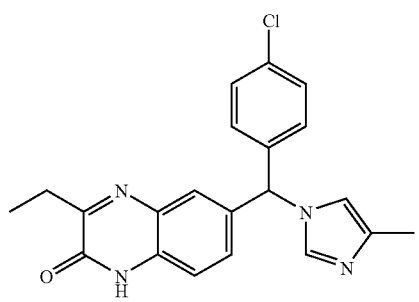
Co. No. 122; Ex. [B21]; mp. 260° C.
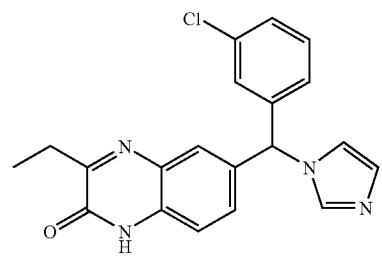
Co. No. 123; Ex. [B21]; mp. 251° C.
TABLE 1-continued
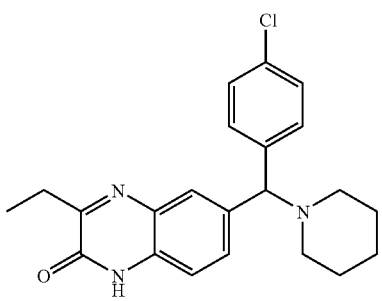
Co. No. 124; Ex. [B21]; mp. 212° C.
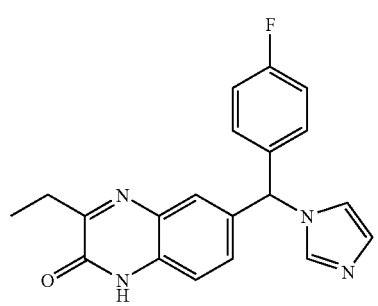
Co. No. 125; Ex. [B21]; mp. 247.7° C.
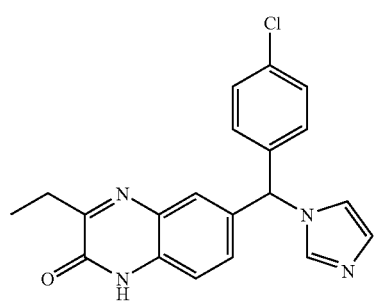
Co. No. 126; Ex. [B21]; mp. 203.8° C.
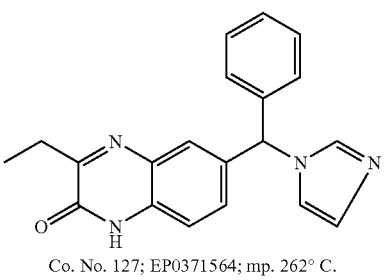
Co. No. 127; EP0371564; mp. 262° C.
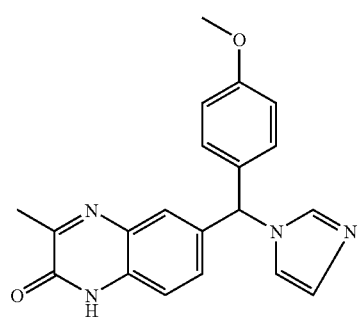
Co. No. 128; EP0371564

TABLE 1-continued
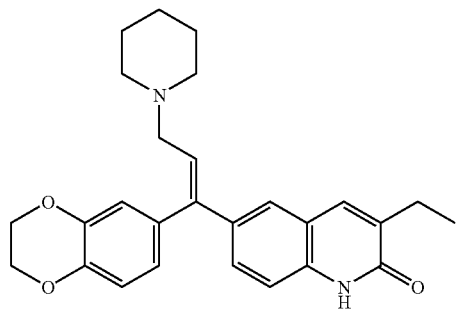
(Z); Co. No. 129; Ex. [B22]; mp. 252° C.
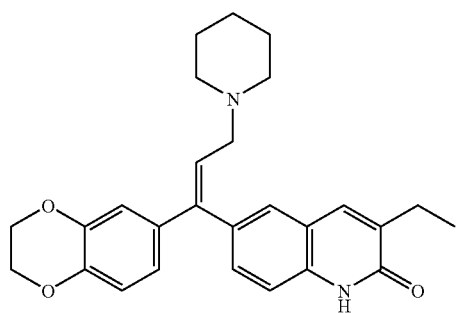
(E); Co. No. 130; Ex. [B22]; mp. 170° C.
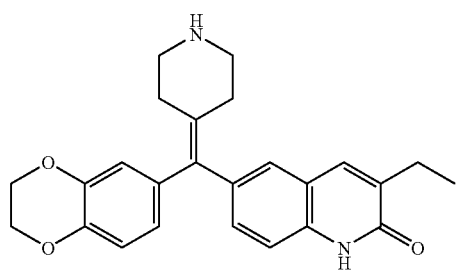
Co. No. 131; Ex. [B23]; mp. 249° C.
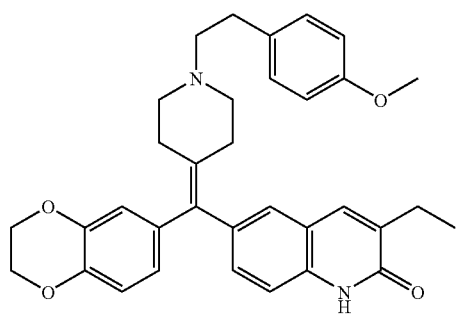
Co. No. 132; Ex. [B24]; mp. 203° C.
TABLE 1-continued
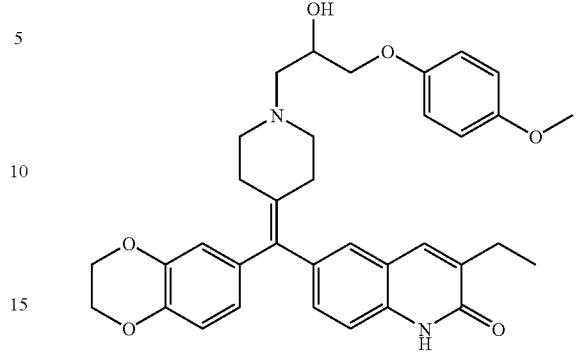
Co. No. 133; Ex. [B25]; mp. 219° C.
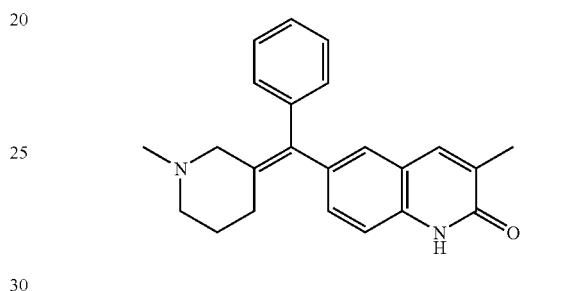
Co. No. 134; Ex. [B22], mp. 205° C.
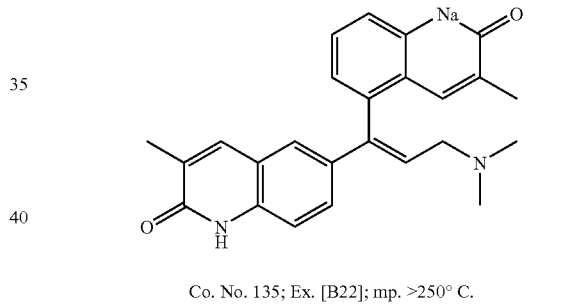
Co. No. 135; Ex. [B22]; mp. >250° C.
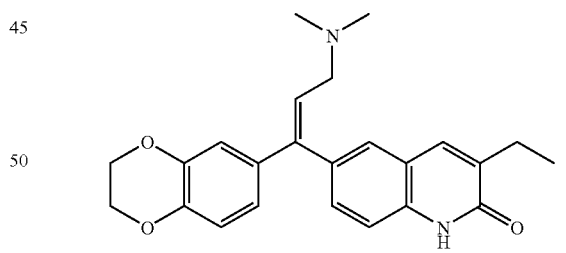
Co. No. 136; Ex. [B22]; mp. 187° C.
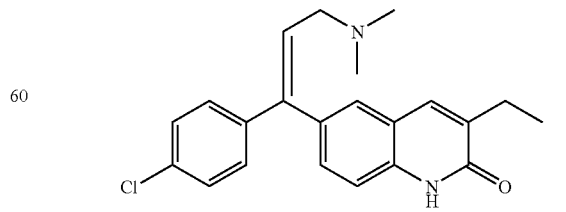
(E); Co. No. 137; Ex. [B22]; mp. 214° C.

TABLE 1-continued
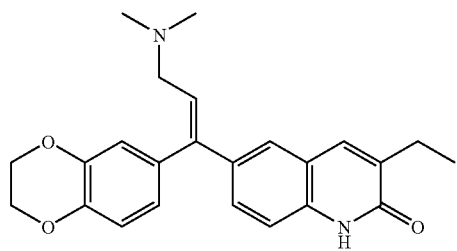
(Z); Co. No. 138; Ex. [B22]; mp. 180° C.
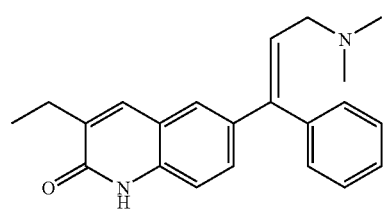
(E); Co. No. 139; Ex. [B22]; mp. 173° C.
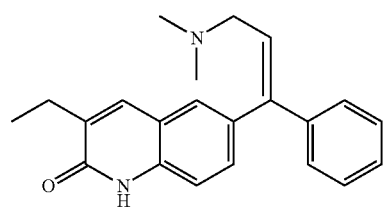
(Z); Co. No. 140; Ex. [B22]; mp. 170° C.
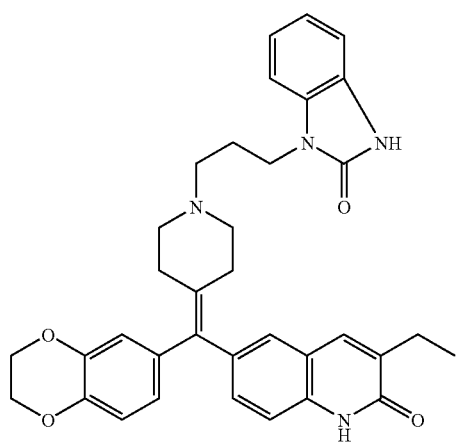
Co. No. 141; Ex. [B24]; mp. 118° C.
TABLE 1-continued
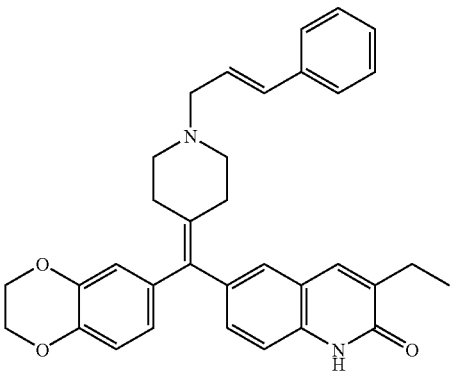
(E); Co. No. 142; Ex. [B24]; mp. 190° C.
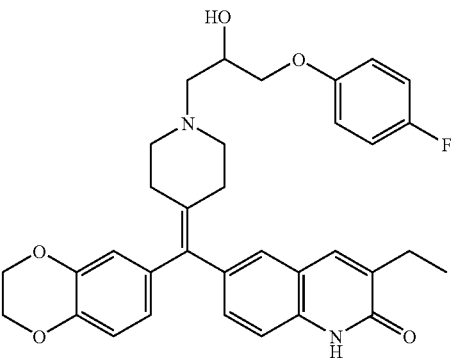
Co. No. 143; Ex. [B25]; mp. 200° C.
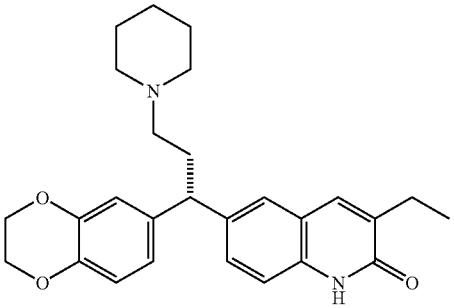
enantiomer A; Co. No. 144; Ex. [B25]; mp. 159° C.
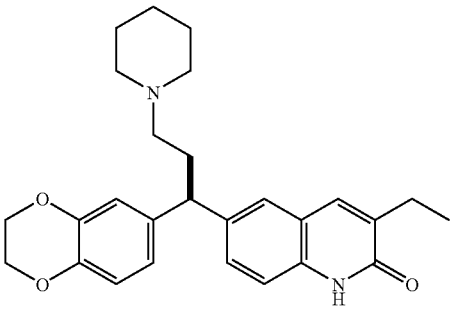
enantiomer B; Co. No. 145; Ex. [B25]; mp. 172° C.

TABLE 1-continued

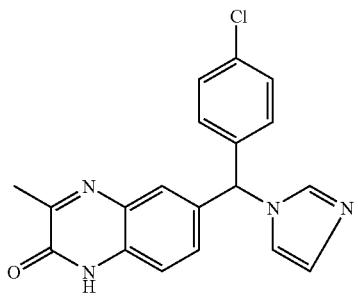

Co. No. 146; EP371564

Pharmacological Example

In vitro Scintillation Proximity Assay (SPA) for PARP-1 Inhibitory Activity

Compounds of the present invention were tested in an in vitro assay based on SPA technology (proprietary to Amersham Pharmacia Biotech).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^-$) as ADP-ribosyl donor.

As inducer of PARP-1 enzyme activity, nicked DNA was prepared. For this, 25 mg of DNA (supplier: Sigma) was dissolved in 25 ml DNAse buffer (10 mM Tris-HCl, pH 7.4; 0.5 mg/ml Bovine Serum Albumine (BSA); 5 mM MgCl$_2$.6H$_2$O and 1 mM KCl) to which 50 µl DNAse solution (1 mg/ml in 0.15 M NaCl) was added. After an incubation of 90 min. at 37° C., the reaction was terminated by adding 1.45 g NaCl, followed by a further incubation at 58° C. for 15 min. The reaction mixture was cooled on ice and dialysed at 4° C. for respectively 1.5 and 2 hours against 1.5 l of 0.2 M KCl, and twice against 1.5 l of 0.01 M KCl for 1.5 and 2 h respectively. The mixture was aliquoted and stored at –20° C. Histones (1 mg/ml, type II-A, supplier: Sigma) were biotinylated using the biotinylation kit of Amersham and stored aliquoted at –20° C. A stock solution of 100 mg/ml SPA poly(vinyl toluene) (PVT) beads (supplier: Amersham) was made in PBS. A stock solution of [$^3$H]-NAD$^+$ was made by adding 120 µl of [$^3$H]-NAD$^+$ (0.1 mCi/ml, supplier: NEN) to 6 ml incubation buffer (50 mM Tris/HCl, pH 8; 0.2 mM DTT; 4 mM MgCl$_2$). A solution of 4 mM NAD$^-$ (supplier: Roche) was made in incubation buffer (from a 100 mM stock solution in water stored at –20° C.). The PARP-1 enzyme was produced using art known techniques, i.e. cloning and expression of the protein starting from human liver cDNA. Information concerning the used protein sequence of the PARP-1 enzyme including literature references can be found in the Swiss-Prot database under primary accession number P09874. Biotinylated histones and PVT-SPA beads were mixed and pre-incubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^1$ was added per well into a 96-well microtiterplate. The final concentrations in the incubation mixture were 2 µg/ml for the biotinylated histones, 2 mg/ml for the PVT-SPA beads, 2 µg/ml for the nicked DNA and between 5-10 µg/ml for the PARP-1 enzyme. After incubation of the mixture for 15 min. at room temperature, the reaction was terminated by adding 100 µl of 4 mM NAD$^+$ in incubation buffer (final concentration 2 mM) and plates were mixed.

The beads were allowed to sediment for at least 15 min. and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$ M or $10^{-6}$ M. When the compounds showed activity at $10^{-5}$ M or $10^{-6}$ M, a dose-response curve was made wherein the compounds were tested at concentrations between $10^{-5}$ M and $10^{-6}$ M. In each test, the blank value was subtracted from both the control and the sample values. The control sample represented maximal PARP-1 enzyme activity. For each sample, the amount of cpm was expressed as a percentage of the mean cpm value of the controls. When appropriate, $IC_{50}$-values (concentration of the drug, needed to reduce the PARP-1 enzyme activity to 50% of the control) were computed using linear interpolation between the experimental points just above and below the 50% level. Herein the effects of test compounds are expressed as $pIC_{50}$ (the negative log value of the $IC_{50}$-value). As a reference compound, 4-amino-1,8-naphthalimide was included to validate the SPA assay. The compounds of the invention showed inhibitory activity at the initial test concentration of $10^{-5}$ M or $10^{-6}$ M (see Tabel-2).

In vitro Filtration Assay for PARP-1 Inhibitory Activity

Compounds of the present invention were tested in an in vitro filtration assay assessing PARP-1 activity (triggered in the presence of nicked DNA) by means of its histone poly (ADP-ribosyl)ation activity using [$^{32}$P]-NAD as ADP-ribosyl donor. The radioactive ribosylated histones were precipitated by trichloroacetic acid (TCA) in 96-well filterplates and the incorporated [$^{32}$P] measured using a scintillation counter A mixture of histones (stock solution: 5 mg/ml in H$_2$O), NAD$^+$ (stock solution: 100 mM in H$_2$O), and [$^{32}$P]-NAD$^+$ in incubation buffer (50 mM Tris/HCl, pH 8; 0.2 mM DTT; 4 mM MgCl$_2$) was made. A mixture of the PARP-1 enzyme (5-10 µg/ml) and nicked DNA was also made. The nicked DNA was prepared as described in the in vitro SPA for PARP-1 inhibitory activity. Seventy-five µl of the PARP-1 enzyme/DNA mixture together with 1 µl of compound in DMSO and 25 µl of histones-NAD$^+$/[$^{32}$P]-NAD$^+$ mixture was added per well of a 96-well filterplate (0.45 µm, supplier Millipore). The final concentrations in the incubation mixture were 2 µg/ml for the histones, 0.1 mM for the NAD$^+$, 200 µM (0.5 µC) for the [$^{32}$P]-NAD$^+$ and 2 µg/ml for the nicked DNA. Plates were incubated for 15 min. at room temperature and the reaction was terminated by the addition of 10 µl ice cold 100% TCA followed by the addition of 10 µl ice-cold BSA solution (1% in H$_2$O). The protein fraction was allowed to precipitate for 10 min. at 4° C. and plates were vacuum filtered. The plates were subsequently washed with, for each well, 1 ml of 10% ice cold TCA, 1 ml of 5% ice cold TCA and 1 ml of 5% TCA at room temperature. Finally 100 µl of scintillation solution (Microscint 40, Packard) was added to each well and the plates were transferred to a TopCount-NXT™ (supplier: Packard) for scintillation counting and values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of $10^{-5}$M. When the compounds showed activity at $10^{-5}$M, a dose-response curve was made wherein the compounds were tested at concentrations between $10^{-5}$M and $10^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, $IC_{50}$-values (concentration of the drug, needed to reduce the PARP-1 enzyme activity to 50% of the control) were computed using linear interpolation between the experimental points just above and below the 50% level. Herein the effects of test compounds are expressed as $pIC_{50}$ (the negative log value of the $IC_{50}$-value). As a reference compound, 4-amino-1,8-naphthalimide was included to validate the filtration assay. The tested compounds showed inhibitory activity at the initial test concentration of $10^{-5}$M (see Tabel-2).

TABEL 2

| Co.No. | In vitro SPA pIC50 | In vitro filtration assay pIC50 |
|---|---|---|
| 1 | 6.545 | 5.632 |
| 2 | 6.134 | |
| 3 | 6.39 | 5.363 |
| 4 | 6.362 | 5.574 |
| 5 | 5.855 | 5.025 |
| 6 | 6.019 | 5.404 |
| 7 | 5.845 | 5.135 |
| 8 | 6.671 | 5.596 |
| 9 | 5.744 | 5.027 |
| 10 | 6.148 | 5.621 |
| 11 | 8.137 | |
| 12 | 7.397 | |
| 13 | 6.657 | 5.675 |
| 14 | 7.013 | |
| 15 | 6.926 | |
| 16 | 8.036 | |
| 17 | 6.817 | 6.208 |
| 18 | 7.711 | |
| 19 | 6.591 | |
| 20 | 6.561 | 5.757 |
| 21 | 6.718 | |
| 22 | 6.436 | 5.393 |
| 23 | 5.85 | 5.485 |
| 24 | 5.565 | 5.12 |
| 25 | 6.303 | 5.409 |
| 26 | 6.925 | 6.037 |
| 27 | 6.034 | 5.633 |
| 28 | 6.645 | 6.112 |
| 29 | 6.099 | 5.321 |
| 30 | 6.441 | 5.744 |
| 31 | 7.672 | |
| 32 | 7.127 | |
| 33 | 7.59 | |
| 34 | 6.28 | |
| 35 | 6.096 | |
| 36 | 6.525 | |
| 37 | 6.52 | 5.932 |
| 38 | 6.5 | 5.576 |
| 39 | 6.225 | 5 |
| 40 | 7.625 | |
| 41 | 6.912 | |
| 42 | 6.023 | |
| 43 | 7.673 | |
| 44 | 7.035 | |
| 45 | 7.341 | |
| 46 | 6.393 | |
| 47 | 6.287 | |
| 48 | 6.722 | |
| 49 | 6.391 | |
| 50 | 6.169 | |
| 51 | 6.338 | |
| 52 | 7.263 | |
| 53 | 6.819 | |
| 54 | 6.995 | |
| 55 | 7.735 | |
| 56 | 6.292 | |
| 57 | 7.474 | |
| 58 | 6.235 | |
| 59 | 6.663 | |
| 60 | 6.529 | |
| 61 | 6.559 | |
| 62 | 6.506 | |
| 63 | 6.442 | |
| 64 | 6.274 | |
| 65 | 6.535 | |
| 66 | 6.38 | |
| 67 | 6.681 | |
| 68 | 6.428 | |
| 69 | 6.341 | |
| 70 | 6.118 | |
| 71 | 6.751 | |
| 72 | 6.676 | 5.677 |
| 73 | 6.908 | |
| 74 | 6.675 | |
| 75 | 6.47 | |
| 76 | 6.386 | |
| 77 | 6.598 | 5.759 |
| 78 | 6.706 | 5.626 |
| 80 | 6.16 | 5.408 |
| 81 | 6.515 | 5.401 |
| 82 | 6.448 | |
| 83 | 6.303 | |
| 84 | 6.497 | |
| 85 | 6.723 | 5.925 |
| 86 | 6.535 | 5.65 |
| 87 | 6.23 | 5.305 |
| 88 | 6.579 | 5.39 |
| 89 | 6.346 | 5.572 |
| 90 | 8.074 | |
| 91 | 6.728 | 6.082 |
| 92 | 6.977 | 5.929 |
| 93 | 6.294 | 5.667 |
| 94 | 6.177 | 5.448 |
| 95 | 6.087 | 5.197 |
| 96 | 7.156 | 6.453 |
| 97 | 7.508 | |
| 98 | 6.562 | 5.417 |
| 99 | 6.539 | 5.833 |
| 100 | 6.299 | 5.455 |
| 101 | 6.112 | 5.546 |
| 102 | 6.437 | 5.799 |
| 103 | 6.045 | 5.112 |
| 104 | 6.3 | 5.624 |
| 105 | 6.209 | 5.833 |
| 106 | 6.307 | 5.775 |
| 107 | 6.075 | 5 |
| 108 | 6.391 | |
| 109 | 6.122 | 5.634 |
| 110 | 6.557 | 5.588 |
| 111 | 6.214 | 5.354 |
| 112 | 6.162 | 5.567 |
| 113 | 6.255 | 5.227 |
| 114 | 6.258 | 5.802 |
| 115 | 6.087 | 5.463 |
| 116 | 6.249 | |
| 117 | 6.149 | |
| 118 | 6.061 | |
| 119 | 6.704 | |
| 120 | 6.257 | |
| 121 | 6.081 | |

TABEL 2-continued

| Co.No. | In vitro SPA pIC50 | In vitro filtration assay pIC50 |
|---|---|---|
| 122 | 6.057 | 5.569 |
| 123 | 6.213 | 5.481 |
| 124 | 5.803 | 5.86 |
| 125 | 6.148 | 5.251 |
| 126 | 6.242 | 5.648 |
| 127 | 5.954 | 5.436 |
| 128 | 6.442 | 5.638 |
| 129 | 7.243 | |
| 130 | 6.725 | |
| 131 | 7.558 | |
| 132 | 7.243 | |
| 133 | 6.906 | |
| 134 | 6.525 | 5.806 |
| 135 | 6.1 | 5.379 |
| 136 | 6.864 | |
| 137 | 6.369 | |
| 138 | 7.201 | |
| 139 | 6.175 | 5.385 |
| 140 | 6.366 | 5.667 |
| 141 | 6.917 | |
| 142 | 6.492 | |
| 143 | 6.804 | |

The compounds can be further evaluated in a cellular chemo- and/or radiosensitization assay, an assay measuring inhibition of endogenous PARP-1 activity in cancer cell lines and eventually in an in vivo radiosensitization test.

The invention claimed is:
1. A compound of formula (I),

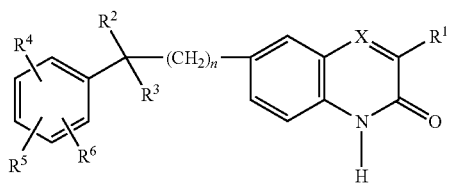
(I)

the N-oxide forms, the pharmaceutically acceptable salts and the stereo-chemically isomeric forms thereof, wherein n is 0, 1 or 2;
X is N or $CR^7$, wherein $R^7$ is hydrogen;
$R^1$ is $C_{1-6}$alkyl;
$R^2$ is hydrogen, hydroxy, $C_{1-6}$alkyl, or $C_{3-6}$alkynyl;
$R^3$ is a radical selected from —$(CH_2)_s$—$NR^8R^9$ (a-1), —O—H (a-2), —O—$R^{10}$ (a-3), —S—$R^{11}$ (a-4), or —C≡N (a-5), wherein
s is 0, 1, 2 or 3;
$R^8$, $R^{10}$ and $R^{11}$ are each independently selected from —CHO, $C_{1-6}$alkyl, hydroxy$C_{1-6}$alkyl, $C_{1-6}$alkylcarbonyl, amino, $C_{1-6}$alkylamino, di($C_{1-6}$alkyl)amino$C_{1-6}$alkyl, $C_{1-6}$alkyloxycarbonyl, $C_{1-6}$alkylcarbonylamino$C_{1-6}$alkyl, piperidinyl$C_{1-6}$alkylaminocarbonyl, piperidinyl, piperidinyl$C_{1-6}$alkyl, $C_{1-6}$alkyloxy, thiophenyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, aryl$C_{1-6}$alkyl($C_{1-6}$alkyl)amino$C_{1-6}$alkyl, and $R^9$ is hydrogen or $C_{1-6}$alkyl;
or $R^3$ is a group of formula —$(CH_2)_t$—Z (b-1), wherein
t is 0, 1, 2 or 3;
—Z is a heterocyclic ring system selected from

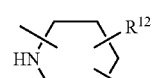
(c-1)

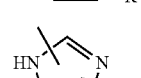
(c-2)

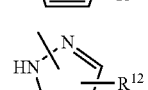
(c-3)

(c-4)

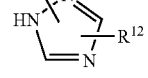
(c-5)

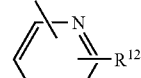
(c-6)

(c-7)

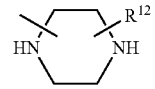
(c-8)

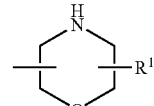
(c-9)

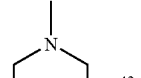

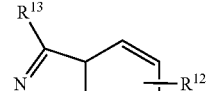
(c-10)

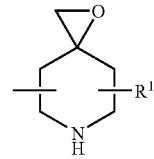

-continued (c-11)

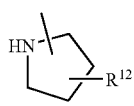

wherein $R^{12}$ is hydrogen, halo, $C_{1-6}$alkyl, aminocarbonyl, amino, hydroxy, aryl,

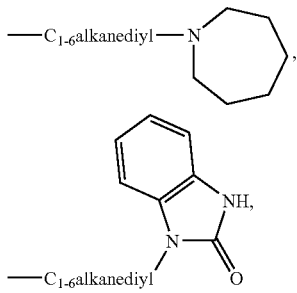

$C_{1-6}$alkylaminoC$_{1-6}$alkyloxy, $C_{1-6}$alkyloxyC$_{1-6}$alkyl, $C_{1-6}$alkyloxyC$_{1-6}$alkylamino, arylC$_{1-6}$alkyl, di(phenylC$_{2-6}$alkenyl), piperidinyl, piperidinylC$_{1-6}$alkyl, $C_{3-10}$cycloalkyl, $C_{3-10}$cycloalkylC$_{1-6}$alkyl, aryloxy(hydroxy)C$_{1-6}$alkyl, haloindazolyl, arylC$_{2-6}$alkenyl, arylC$_{1-6}$alkylamino, morpholino, $C_{1-6}$alkylimidazolyl, pyridinylC$_{1-6}$alkylamino; and $R^{13}$ is hydrogen, piperidinyl or aryl;

$R^4$, $R^5$ and $R^6$ are each independently selected from hydrogen, halo, trihalomethyl, trihalomethoxy, $C_{1-6}$alkyl, $C_{1-6}$alkyloxy, amino, aminoC$_{1-6}$alkyl, di(C$_{1-6}$alkyl)amino, di(C$_{1-6}$alkyl)aminoC$_{1-6}$alkyloxy or $C_{1-6}$alkyloxycarbonyl, or $C_{1-6}$alkyl substituted with 1, 2 or 3 substituents independently selected from hydroxy, $C_{1-6}$alkyloxy, or aminoC$_{1-6}$alkyloxy; or when $R^5$ and $R^6$ are on adjacent positions they may taken together form a bivalent radical of formula —O—CH$_2$—O— (d-1), —O—(CH$_2$)$_2$—O— (d-2), —CH=CH—CH=CH— (d-3), or —NH—C(O)—NR$^{14}$=CH— (d-4), wherein $R^{14}$ is $C_{1-6}$alkyl;
and aryl is phenyl, phenyl substituted with halo, $C_{1-6}$alkyl or $C_{1-6}$alkyloxy.

2. A compound as claimed in claim 1 wherein
$R^3$ is a radical selected from the group consisting of (a-1), (a-2), (a-3) (a-5), and (b-1) wherein —Z is a heterocyclic ring system selected from (c-1), (c-6), (c-8), (c-9), or (c-11); s is 0, 1 or 2; $R^8$ and $R^{10}$ are each independently selected from —CHO, $C_{1-6}$alkyl, hydroxyC$_{1-6}$alkyl, di(C$_{1-6}$alkyl)aminoC$_{1-6}$alkyl, $C_{1-6}$alkylcarbonylaminoC$_{1-6}$alkyl, piperidinylC$_{1-6}$alkyl, piperidinylC$_{1-6}$alkylaminocarbonyl, $C_{1-6}$alkyloxy, thiophenylC$_{1-6}$alkyl, pyrrolylC$_{1-6}$alkyl, arylC$_{1-6}$alkylpiperidinyl, arylcarbonylC$_{1-6}$alkyl, arylcarbonylpiperidinylC$_{1-6}$alkyl, haloindozolylpiperidinylC$_{1-6}$alkyl, or arylC$_{1-6}$alkyl(C$_{1-6}$alkyl)aminoC$_{1-6}$alkyl; t is 0 or 2; $R^{12}$ is hydrogen, $C_{1-6}$alkyl, aminocarbonyl,

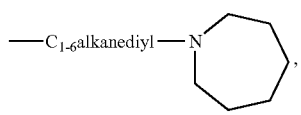

$C_{1-6}$alkyloxyC$_{1-6}$alkylamino, di(phenylC$_{2-6}$alkenyl), piperidinylC$_{1-6}$alkyl, $C_{3-10}$cycloalkyl, $C_{3-10}$cycloalkylC$_{1-6}$alkyl, haloindazolyl, or arylC$_{2-6}$alkenyl; $R^4$, $R^5$ and $R^6$ are each independently selected from hydrogen, halo, trihalomethyl, trihalomethoxy, $C_{1-6}$alkyl, $C_{1-6}$alkyloxy, di(C$_{1-6}$alkyl)amino, di(C$_{1-6}$alkyl)aminoC$_{1-6}$alkyloxy or $C_{1-6}$alkyloxycarbonyl; and when $R^5$ and $R^6$ are on adjacent positions they may taken together form a bivalent radical of formula (d-1) or (d-2).

3. A compound according to claim 1 wherein
n is 0; X is CH; $R^2$ is hydrogen; Z is a heterocyclic ring system selected from (c-1); t is 2; $R^{12}$ is hydrogen; $R^{13}$ is hydrogen; and $R^5$ and $R^6$ are on adjacent positions and taken together form a bivalent radical of formula (d-2).

4. A compound selected from the group consisting of

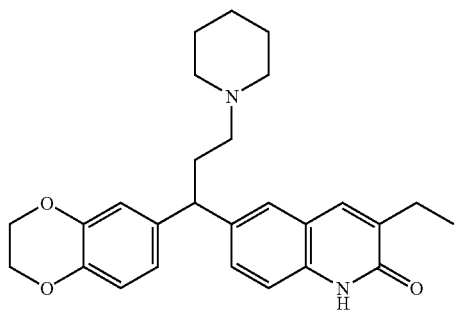

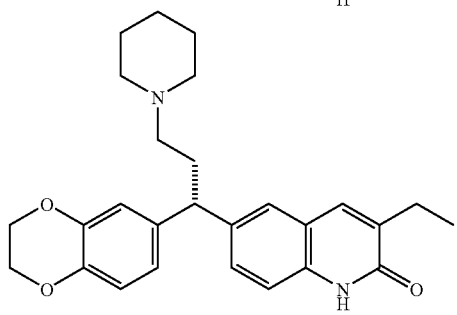

and

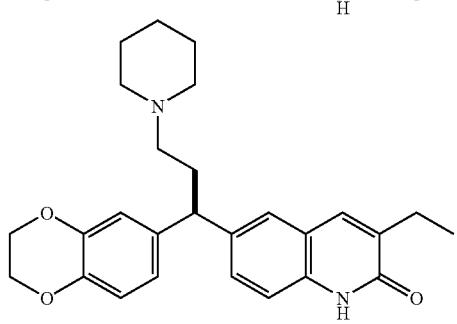

.

5. A pharmaceutical composition comprising pharmaceutically acceptable carriers and as an active ingredient a therapeutically effective amount of a compound as claimed in claim 1.

* * * * *